US007729864B2

(12) United States Patent
Schadt

(10) Patent No.: US 7,729,864 B2
(45) Date of Patent: Jun. 1, 2010

(54) COMPUTER SYSTEMS AND METHODS FOR IDENTIFYING SURROGATE MARKERS

(75) Inventor: Eric E. Schadt, Kirkland, WA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 776 days.

(21) Appl. No.: 10/558,928

(22) PCT Filed: May 28, 2004

(86) PCT No.: PCT/US2004/016917

§ 371 (c)(1),
(2), (4) Date: Feb. 8, 2007

(87) PCT Pub. No.: WO2004/109447

PCT Pub. Date: Dec. 16, 2004

(65) Prior Publication Data

US 2007/0185656 A1      Aug. 9, 2007

Related U.S. Application Data

(60) Provisional application No. 60/474,730, filed on May 30, 2003.

(51) Int. Cl.
*G06F 19/00*      (2006.01)
*G06F 15/00*      (2006.01)
*G11C 17/00*      (2006.01)
(52) U.S. Cl. ................................. 702/19; 365/94; 700/1
(58) Field of Classification Search ....................... None
See application file for complete search history.

(56) References Cited

U.S. PATENT DOCUMENTS

| | | | |
|---|---|---|---|
| 5,075,217 A | 12/1991 | Weber | |
| 5,324,631 A | 6/1994 | Helentjaris et al. | |
| 5,510,270 A | 4/1996 | Fodor et al. | |
| 5,569,588 A | 10/1996 | Ashby et al. | |
| 5,578,832 A | 11/1996 | Trulson et al. | |
| 5,965,352 A | 10/1999 | Stoughton et al. | |
| 6,132,969 A | 10/2000 | Stoughton et al. | |
| 6,132,997 A | 10/2000 | Shannon | |
| 6,165,709 A | 12/2000 | Friend et al. | |
| 6,218,122 B1 | 4/2001 | Friend et al. | |
| 6,271,002 B1 | 8/2001 | Linsley et al. | |
| 6,324,479 B1 | 11/2001 | Friend et al. | |
| 6,368,806 B1 | 4/2002 | Openshaw et al. | |
| 2003/0180761 A1 | 9/2003 | Castonguay et al. | |
| 2003/0224394 A1 | 12/2003 | Schadt et al. | |
| 2006/0111849 A1 | 5/2006 | Schadt et al. | |
| 2006/0122816 A1 | 6/2006 | Schadt et al. | |

FOREIGN PATENT DOCUMENTS

| WO | WO 9913107 | 3/1999 |
|---|---|---|
| WO | WO 03065282 | 8/2003 |
| WO | WO 03100557 | 12/2003 |
| WO | WO 2004013727 | 2/2004 |
| WO | WO 2004 061616 | 7/2004 |
| WO | WO 2004 109447 | 12/2004 |
| WO | WO 2005 017652 | 2/2005 |
| WO | WO 2005 107412 | 11/2005 |

OTHER PUBLICATIONS

Tang et al. Blood Genomic Responses Differ After Stroke, Seizures, Hypoglycemia, and Hypoxia: Blood Genomic Fingerprints of Disease Annals of Neurology vol. 50, pp. 699-707 (2001).*
U.S. Appl. No. 11/361,871, filed Feb. 23, 2006, Schadt et al.
U.S. Appl. No. 10/558,928, filed Nov. 30, 2005, Schadt et al.
U.S. Appl. No. 10/540,405, filed Dec. 24, 2003, Schadt et al.
PCT/US05/15419, May 2, 2005, International Search Report.
PCT/US04/16917, May 28, 2004, International Search Report.
PCT/US03/03100, Feb. 3, 2003, International Search Report.
PCT/US03/023976, Aug. 1, 2003, International Search Report.
PCT/US03/41613, Dec. 24, 2003, International Search Report.
PCT/US03/15768, May 20, 2003, International Search Report.
Aitman et al., 1999, "Identification of Cd36 (Fat) as an insulin-resistance gene causing defective fatty acid and glucose metabolism in hypertensive rats," Nature Genetics 21: 76-83.
Akagi et al., 1996, "Microsatellite DNA markers for rice chromosomes," Theor. Appl. Genet. 93:1071-1077.
Allison et al., 1998, "Multiple phenotype modeling in gene-mapping studies of quantitative traits: power advantages," Am. J. Hum. Genet. 63:1190-1201.
Amos et al., 1990, "A multivariate method for detecting genetic linkage, with application to a pedigree with an adverse lipoprotein phenotype," Am. J. Hum. Genet. 47:247-254.
Barbosa et al., 1976, "The genetic heterogeneity of diabetes : histocompatibility antigens (HLA) in families with maturity-onset type diabetes of the young (MODY) and juvenile, insulin-dependent diabetes (JID) [proceedings]," Diabete. Metab. 2:160.
Blanchard et al., 1996, "Sequence to array: Probing the genome's secrets," Nature Biotechnology 14:1649.

(Continued)

*Primary Examiner*—John S Brusca
(74) *Attorney, Agent, or Firm*—Christensen O'Connor Johnson Kindness PLLC

(57) ABSTRACT

Methods, computer program products and systems for identifying cellular constituents in a secondary tissue that serve as surrogate markers for a target gene expressed in a primary tissue of a species are provided. A classifier is constructed using cellular constituent abundances of cellular constituents in a first plurality of cellular constituents measured in the secondary tissue in a population. This population comprises a first and second subgroup. The classifier is based on a second plurality of cellular constituents that comprises all or a portion of the first plurality of cellular constituents. Abundance levels of each cellular constituent in the second plurality of cellular constituents varies between the first and second subgroup. All or portion of the population is classified into a plurality of subtypes using the classifier. Then, one or more cellular constituents that can discriminate members of the population between a first subtype and a second subtype in the plurality of subtypes are identified.

67 Claims, 17 Drawing Sheets

OTHER PUBLICATIONS

Blanchard et al., 1996, "High-density oligonucleotide arrays," Biosensors & Bioelectronics 11: 687-690.

Bligh et al, 1995, "A microsatellite sequence closely linked to the Waxy gene of *Oryza sativa*," Euphytica 86:83-85.

Bochner et al., 2001, "Phenotype microarrays for high-throughput phenotypic testing and assay of gene function," Genome Res. 11:1246-1255.

Börjeson, 1976, "The aetiology of obesity in children," Acta. Paediar. Scand. 65:279-287.

Bray, 1989, "1989 McCollum Award Lecture. Genetic and hypothalamic mechanisms for obesity-finding the needle in the haystack," Am. J. Clin. Nutr. 50:891-902.

Bray, 1992, "Genetic, hypothalamic and endocrine features of clinical and experimental obesity," Progress in Brain Research 93:333-341.

Brem et al., 2002, "Genetic Dissection of Transcriptional Regulation in Budding Yeast," Science 296:752-755.

Brown et al., 2000, "Knowledge-based analysis of microarray gene expression data by using support vector machines," Proc. Natl. Acad. Sci. USA 97:262-267.

Cheung et al., 2002, "The genetics of variation in gene expression," Nature Genetics Supplement 32: 522-525.

Cheung et al., 2003, "Natural variation in human gene expression assessed in lymphoblastoid cells," Nature Genetics 33: 422-425.

Chirgwin et al., 1979, "Isolation of biologically active ribonucleic acid from sources enriched in ribonuclease," Biochemistry 18:5294-5299.

Cohen et al., 2000, "A computational analysis of whole-genome expression data reveals chromosomal domains of gene expression," Nature Genetics 26:183-186.

Corder et al., 1993, "Gene dose of apolipoprotein E type 4 allele and the risk of Alzheimer's disease in late onset families," Science 261:921-923.

Cox et al., 1999, "Loci on chromosomes 2 (NIDDM1) and 15 interact to increase susceptibility to diabetes in Mexican Americans," Nature Genetics 21:213-215.

DeRisi et al., 1996, "Use of a cDNA microarray to analyse gene expression patterns in human cancer," Nature Genetics 14:457-460.

Doerge, 2002, "Mapping and analysis of quantitative trait loci in experimental populations," Nature Reviews 3:43-52.

Draghici, 2003, "Data Analysis Tools for DNA Microarrays," Chapman & Hall, p. 1-478.

Duda et al., 2001, Pattern Classification, John Wiley & Sons, New York, NY, p. 521-530.

Duda et al., 2001, Pattern Classification, John Wiley & Sons, New York, NY, p. 550-557.

Easton et al., 1993, "Inherited susceptibility to breast cancer," Cancer Surv. 18:95-113.

Eaves et al., 2002, "Combining Mouse Congenic Strains and Microarray Gene Expression Analyses to Study a Complex Trait: The NOD Model of Type 1 Diabetes," Genome Research 12: 232-243.

Egholm et al., 1993, "PNA hybridizes to complementary oligonucleotides obeying the Watson-Crick hydrogen-bonding rules," Nature 365:566-568.

Elowitz et al., 2002, "Stochastic Gene Expression in a Single Cell," Science 297:1183-1186.

Falk et al., 1987, "Haplotype relative risks: an easy reliable way to construct a proper control sample for risk calculations," Ann. Hum. Genet. 51 ( Pt 3):227-233.

Ferguson et al., 1996, "A fiber-optic DNA biosensor microarray for the analysis of gene expression," Nature Biotechnology 14:1681-1684.

Fiehn et al., 2000, "Metabolite profiling for plant functional genomics," Nature Biotech. 18:1157-1161.

Fishel et al., 1993, "The human mutator gene homolog MSH2 and its association with hereditary nonpolyposis colon cancer," Cell 75:1027-1038.

Fodor et al., 1991, "Light-directed, spatially addressable parallel chemical synthesis," Science 251:767-773.

Ford et al., 1994, "Risks of cancer in BRCA1—mutation carriers. Breast Cancer Linkage Consortium," Lancet 343:692-695.

Friedman et al., 1991, "Molecular mapping of obesity genes," Mammalian Genome 1:130-144.

Friedman et al., 1992, "Tackling a weighty problem," Cell 69:217-220.

Froehler et al., 1986, "Synthesis of DNA via deoxynucleoside H-phosphonate intermediates," Nucleic Acids Research 14:5399-5407.

Fulker et al., 1999, "Combined Linkage and Association Sib-Pair Analysis for Quantitative Traits," Am. J. Hum. Genet. 64:259-267.

Fullerton et al., 2000, "Apolipoprotein E variation at the sequence haplotype level: implications for the origin and maintenance of a major human polymorphism," Am. J. Hum. Genet. 67:881-900.

Gaasterland et al., 2000, "Making the most of microarray data," Nature Genetics 24:204-206.

Goffeau et al., 1996, "Life with 6000 genes," Science 274:546-567.

Grunau et al., 2001, "MethDB-a public database for DNA methylation data," Nucelic Acids Research, 29: 270-274.

Grundy et al., 1990, "Metabolic and health complications of obesity," Dis. Mon. 36:641-731.

Haley et al., 1992, "A simple regression method for mapping quantitative trait loci in line crosses using flanking markers," The Genetical Society of Great Britain 69:315-324.

Hayashi et al., 1994, "Detection of additive and dominance effects of QTLs in interval mapping of F2 RFLP data," Theor. Appl. Genet. 87:1021-1027.

Helentjaris et al., 1985, "Restriction fragment polymorphisms as probes for plant diversity and their development as tools for applied plant breeding," Plant Molecular Biology 5:109-118.

Helm et al., 1991, "Classification and identification of bacteria by Fourier-transform infrared spectroscopy," Journal of General Microbiology 137: 69-79.

Hu et al., 1991, "Identification of broccoli and cauliflower cultivars with RPD markers," Plant Cell Reports 10:505-511.

Hughes et al., 2000, "Functional Discovery via a Compendium of Expression Profiles," Cell 102:109-126.

International Human Genome Consortium, 2001, "Initial sequencing and analysis of the human genome," Nature 409:860-921.

James et al., 1998, "Non-alcoholic steatohepatitis (NASH): a disease of emerging identity and importance," Journal of Hepatology 29: 495-501.

Jansen, 1993, "Interval mapping of multiple quantitative trait loci," Genetics 135:205-211.

Jansen, 1994, "Controlling the type I and type II errors in mapping quantitative trait loci," Genetics 138:871-881.

Jansen et al., 2001, "Genetical genomics: the added value from segregation," Trends in Genetics 17:388-391.

Jarvis et al., 1973, "Clustering using a similarity measure based on shared near neighbors," IEEE Transactions on computers C-22:1025-1034.

Jaspers et al., 1982, "Genetic heterogeneity in ataxia-telangiectasia studied by cell fusion," Proc. Natl. Acad. 79: 2641-2644.

Jiang et al., 1995, "Multiple trait analysis of genetic mapping for quantitative trait loci," Genetics 140:1111-1127.

Jin et al., 2001, "The contributions of sex, genotype and age to transcriptional variance in *Drosophila melanogaster*," Nature Genetics 29: 389-395.

Kajiwara et al., 1994, "Digenic Retinitis Pigmentosa Due to Mutations at the Unlinked Peripherin/RDS and ROM1 Loci," Science 264: 1604-1608.

Karp et al., 2000, "Identification of complement factor 5 as a susceptibility locus for experimental allergic asthma," Nature Immunology, vol. 1, No. 3: 221-226.

Kearsey et al., 1994, "QTL analysis: a simple 'marker-regression' approach," Theor. Appl. Genet. 89:698-702.

Knapp et al., 1993, "The haplotype-relative-risk (HRR) method for analysis of association in nuclear families," Am. J. Hum. Genet. 52:1085-1093.

Knoll et al., 1993, "Cytogeneitc and Molecular Studies in the Prader-Willi and Angelman Syndromes: An Overview," Amer. Journal of Medical Genetics 46: 2-6.

Kruglyak et al., 1996, "Parametric and nonparametric linkage analysis: a unified multipoint approach," Am. J. Hum. Genet. 58:1347-1363.

Kruglyak et al., 1998, "Faster multipoint linkage analysis using Fourier transforms," J. Comput. Biol. 5:1-7.

Kruglyak et al., 2001, "Variation is the spice of life," Nature Genetics 27:234-236.

Lan et al., 2006, Combined Expression Trait Correlations and Expression Quantitative Trait Locus Mapping, Jan. 2006, Plos Genetics 2:51-61.

Lance et al., 1967, "A general theory of classificatory sorting strategies," Computer Journal 9:373-380.

Lander et al., 1989, "Mapping Mendelian factors underlying quantitative traits using RFLP linkage maps," Genetics 121:185-199.

Lander et al., 1994, "Genetic dissection of complex traits," Science 265:2037-2048.

Lander, 1996, "The new genomics: Global views of biology," Science 274:536-539.

Levsky et al., 2002, "Single-Cell gene expression profiling," Science 297:836-840.

Lockhart et al., 1996, "Expression monitoring by hybridization to high-density oligonucleotide arrays," Nature Biotechnology 14:1675-1680.

Lynch et al., 1998, "Genetics and Analysis of Quantitative Traits," Sinauer Associates, Inc.: Chapters 15 and 16 pp: 431-532.

Machleder et al., 1997, "Complex Genetic Control of HDL Levels in Mice in Response to an Atherogenic Diet," J. Clin. Invest. 99:1406-1419.

Manly et al., 1999, "Overview of QTL mapping software and introduction to Map Manager QT," Mammalian Genome 10:327-334.

Martinez et al., 1994, "Missing markets when estimating quantitative trait loci using regression mapping," The Genetical Society of Great Britain 73:198-206.

Maskos et al., 1992, "Oligonucleotide hybridisations on glass supports: a novel linker for oligonucleotide synthesis and hybridisation properties of oligonucleotides synthesised in situ," Nucleic Acids Research 20: 1679-1684.

McBride et al., 1983, "An Investigation of Several Deoxynucleoside Phosphoramidites Useful for Sythesizing Deoxyoligonucleotides," Tetrahedron Letters 24: 245-248.

Moll et al., 1991, "The Genetic and Environmental Sources of Body Mass Index Variability: Te Muscatine Ponderosity Family Study," Am. J. Hum. Genet. 49: 1243-1255.

Mount, 2001, "Genome Analysis," Bioninformatics Sequence and Genome Analysis Chapter 10, p. 479-531.

Naumann et al., 1991, "Microbiological characterizations by FT-IR spectroscopy," Nature 351: 81-82.

Nguyen et al., 1995, "Differential gene expression in the murine thymus assayed by quantitative hybridization of arrayed cDNA clones," Genomics 29:207-216.

Nishina et al., 1994, "Atherosclerosis in genetically obese mice: the mutants obese, diabetes, fat, tubby, and lethal yellow," Metabolism 43:554-558.

Olson et al., 1999, "Tutorial in biostatistics genetic mapping of complex traits," Statistics in Medicine 18:2961-2981.

Patil et al., 2001, "Blocks of limited haplotype diversity revealed by high-resolution scanning of human chromosome 21," Science 294:1719-1723.

Pericak-Vance et al., 1991, " Linkae Studies in Familial Alzheimer Disease: Evidence for Chromosome 19 Linkage," Am. J. Hum. Genet. 48: 1034-1050.

Prashar et al., 1996, "Analysis of differential gene expression by display of 3' end restriction fragments of cDNAs," Proc. Natl. Acad. Sci. USA 93:659-663.

Reeders et al., 1987, "A study of genetic linkage heterogeneity in adult polycystic kidney disease," Hum. Genet. 76:348-351.

Roberts et al., 2000, "Signaling and Circuitry of Multiple MAPK Pathways Revealed by a Matrix of Global Gene Expression Profiles," Science 287: 873-880.

Sagliocco et al., 1996, "Identification of Proteins of the Yeast Protein Map using Genetically Manipulated Strains and Peptide-Mass Fingerprinting," Yeast 12: 1519-1533.

Sandberg et al., 2000, "Regional and strain-specific gene expression mapping in the adult mouse brain," PNAS 97: 11038-11043.

Schadt et al., 2003, "Genetics of gene expression surveyed in maize, mouse and man," Nature 422:297-302.

Schadt et al., 2003, "A new paradigm for drug discovery: integrating clinical genetic, genomic and molecular phenotype data to identify drug targets," Biochemical Society 31:437-443.

Schena et al., 1996, "Parallel human genome analysis; microarray-based expression of 1000 genes," Proc. Natl. Acad. Sci. USA 93:10614-10619.

Schena et al., 1995, "Quantitative Monitoring of Gene Expression Patterns with a Complementary DNA Microarray," Science 270: 467-470.

Shalon et al., 1996, "A DNA microarray system for analyzing complex DNA samples using two-color fluorescent probe hybridization," Genome Research 6:639-645.

Spielman et al., 1989, "Genetic Analysis of IDDM: Summary of GAW5 IDDM Results," Genetic Analysis of complex Traits, Part I: 43-58.

Steinmetz et al., 2002, "Dissecting the architecture of a quantitative trait locus in yeast," Nature 416: 326-330.

St. George-Hyslop et al., 1990, "Genetic linkage studies suggest that Alzheimer's disease is not a single homogeneous disorder. FAD Collaborative Study Group," Nature 347:194-197.

Struss et al., 1998, "The use of microsatellite markers for detection of genetic diversity in barley populations," Theor. Appl. Genet. 97:308-315.

Stover, et al., 2001, "Characterization of Gene Expression Profiles in Peripheral Blood Mononuclear Cells and Bone Marrow of Normal Human Volunteers," FASEB Journal, 534.9: A696.

Stunkard et al., 1990, "The Body-Mass Index of Twins Who Have Been Reared Apart," New England Journal of Medicine 322: 1483-1487.

Tamayo et al., 1999, "Interpreting patterns of gene expression with self-organizing maps: Methods and application to hematopoietic differentiation," Proc. Natl. Acad. Sci. USA 96:2907-2912.

Terwilliger et al., 1992, "A haplotype-based 'haplotype relative risk' approach to detecting allelic associations," Hum. Hered. 42:337-346.

Twine et al., 2003, "Disease-associated Expression Profiles in Peripheral Blood Mononuclear Cells from Patients with Advanced Renal Cell Carcinoma," Cancer Research 63: 6069-6075.

Velculescu et al., 1995, "Serial Analysis of Gene Expression," Science 270: 484-487.

Venter et al., 2001, "The Sequence of the Human Genome," Science 291: 1304-1351.

de Weerd-Kasstelein et al., 1972, "Genetic Heterogeneity of Xeroderma Pigmentosum demonstrated by Somatic Cell Hybridization," Nature New Biology 238: 80-83.

Welsh et al., 1990, "Fingerprinting genomes using PCR with arbitrary primers," Nucleic Acids Research 18: 7213-7218.

Williams et al., 1999, "Joint multipoint linkage analysis of multivariate qualitative and quantitative traits," Am. J. Hum. Genet. 6:1134-1147.

Wu et al., 1993, "Abundance, polymorphism and genetic mapping of microsatellites in rice," Mol. Gen. Genet. 241:225-235.

Younossi et al., 2002, "Perspectives in Clinical Hepatology: Nonalcoholic Fatty Liver Disease: An Agenda for Clinical Research," Hepatology: 746-752.

Zeng, 1993, "Theoretical basis for separation of multiple linked gene effects in mapping quantitative trait loci," Proc. Natl. Acad. Sci. USA 90:10972-10976.

Zeng, 1994, "Precision mapping of quantitative trait loci," Genetics 136:1457-1468.

Davis et al., 2005, "Ultrafine Mapping of SNPs From Mouse Strains C57BL/6J, DBA/2J, and C57BLKS/J for Loci Contributing to Diabetes and Atherosclerosis Susceptibility," Diabetes 54:1191-1199.

Doss et al., 2005, "Cis-acting Expression Quantitative Trait Loci in Mice," Genome Research 15:681-691.

Ghazalpour et al., 2005, "Genomic analysis of metabolic pathway gene expression in mice," Genome Biology 6:R59.

Kraft et al., 2003, "A Family-Based Test for Correlation Between Gene Expression and Trait Values," The American Society of Human Genetics 72:1323-1330.

Pease et al., 1994, "Light-generated oligonucleotide arrays for rapid DNA sequence analysis," Proc. Natl. Acad. Sci. 91: 5022-5026.

Schadt et al. 2004, "A Comprehensive Transcript Index of the Human Genome Generated Using Microarrays and Computational Approaches," Genome Biology 5 R73.

Shevchenko et al., 1996, "Linking genome and proteome by mass spectrometry: Large-scale identification of yeast proteins from two dimensional gels," Proc. Natl. Acad. Sci. 93: 14440-14445.

GuhaThakurta et al., Sep. 15, 2006, "Cis-regulatory variations: A study of SNPs around genes showing cis-linkage in segregating mouse populations," BMC Genomics 7, 235.

* cited by examiner

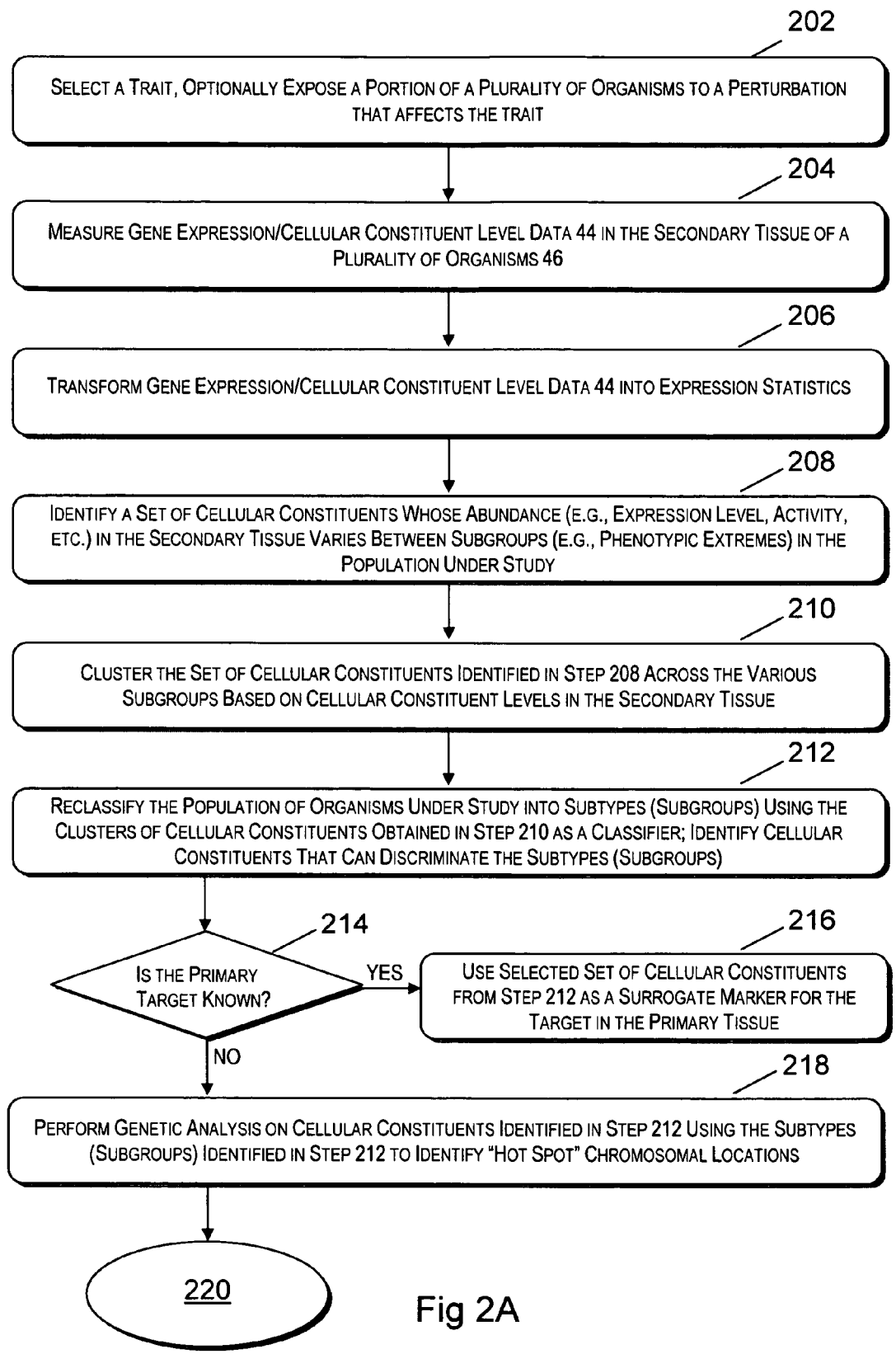

One-dimensional agglomerative hierarchical clustering of rat genes

|  | PHENOTYPE 1 | ... | PHENOTYPE M | CC 48-1 | ... | CC 48-Z |
|---|---|---|---|---|---|---|
| ORGANISM 46-1 | AMOUNT 1101-1-1 | ... | AMOUNT 1101-1-M | LEVEL 50-1-1 | ... | LEVEL 50-1-Z |
| ORGANISM 46-2 | AMOUNT 1101-2-1 | ... | AMOUNT 1101-2-M | LEVEL 50-2-1 | ... | LEVEL 50-2-Z |
| ⋮ | ⋮ | ⋮ | ⋮ | ⋮ | ⋮ | ⋮ |
| ORGANISM 46-N | AMOUNT 1101-N-1 | ... | AMOUNT 1101-N-M | LEVEL 50-N-1 | ... | LEVEL 50-N-Z |

FIG. 11

COMPUTER SYSTEMS AND METHODS FOR IDENTIFYING SURROGATE MARKERS

CROSS-REFERENCE TO RELATED APPLICATIONS

This application claims benefit, under 35 U.S.C. §119(e), of U.S. Provisional Patent Application No. 60/474,730, filed on May 30, 2003 which is hereby incorporated by reference in its entirety.

1. FIELD OF THE INVENTION

The field of this invention relates to computer systems and methods for identifying genes and biological pathways associated with traits. In particular, this invention relates to computer systems and methods for identifying a pattern of gene expression that is affected by the activity level of a target gene or quantitative trait loci.

2. BACKGROUND OF THE INVENTION

A central goal to drug discovery is the identification of a pathway associated with a trait, such as a human disease. Once a pathway has been identified, a number of approaches can be used to influence the trait, including the design of inhibitors of components (e.g., genes) of the pathway. In this way, a compound that ameliorates the effects of the trait can be developed.

The development of a compound or other entity that ameliorates the effects of a trait requires two components. First, the gene or pathway that affects a trait must be elucidated. Second, the activity of the gene or the activity of key genes in the pathway must be assayed in the presence of compounds or other entities in order to identify a compound or other entity that effectively alters the activity of the gene or affects (down regulates, up regulates) the pathway.

2.1. Use of Genetics Data to Identify Genes and Pathways Associated with Traits Genetic data has been used in the field of trait analysis in order to attempt to identify the genes that affect such traits. A key development in such pursuits has been the development of large collections of molecular/genetic markers, which can be used to construct detailed genetic maps of species, such as humans. These maps are used in Quantitative Trait Locus (QTL) mapping methodologies such as single-marker mapping, interval mapping, composite interval mapping and multiple trait mapping. For a review, see Doerge, 2002, Mapping and analysis of quantitative trait loci in experimental populations, *Nature Reviews: Genetics* 3:43-62. QTL mapping methodologies provide statistical analysis of the association between phenotypes and genotypes for the purpose of understanding and dissecting the regions of a genome that affect traits.

A quantitative trait locus (QTL) is a region of any genome that is responsible for some percentage of the variation in the quantitative trait of interest. The goal of identifying all such regions that are associated with a specific complex phenotype is typically difficult to accomplish because of the sheer number of QTL, the possible epistasis or interactions between QTL, as well as many additional sources of variation that can be difficult to model and detect. To address these problems, QTL experiments can be designed with the aim of containing the sources of variation to a limited number in order to improve the chances of dissecting a complex phenotype. In general, a large sample of individuals has to be collected to represent the total population, to provide an observable number of recombinants, and to allow a thorough assessment of the trait under investigation. Using this information, coupled with one of several methodologies to detect or locate QTL, associations between quantitative traits and genetic markers are made as steps toward understanding the genetic basis of traits.

A drawback with QTL approaches is that, even when genomic regions that have statistically significant associations with traits are identified, such regions are usually so large that subsequent experiments, used to identify specific causative genes in these regions, are time consuming and laborious. High density marker maps of the genomic regions are required. Furthermore, physical resequencing of such regions is often required. In fact, because of the size of the genomic regions identified, there is a danger that causative genes within such regions simply will not be identified. In the event of success, and the genomic region containing genes that are responsible for the trait variation are elucidated, the expense and time from the beginning to the end of this process is often too great for identifying genes and pathways associated with traits, such as complex human diseases.

In the case of humans, the use of genetics to identify genes and pathways associated with traits follows a very standard paradigm. First, a genome-wide linkage study is performed using hundreds of genetic markers in family-based data to identify broad regions linked to the trait. The result of this standard sort of linkage analysis is the identification of regions controlling for the trait, thereby restricting attention from the 30,000 plus genes to perhaps as few as 500 to 1000 genes in a particular region of the genome that is linked to the trait. However, the regions identified using linkage analysis are still far too broad to identify candidate genes associated with the trait. Therefore, such linkage studies are typically followed up by fine mapping the regions of linkage using higher density markers in the linkage region, increasing the number of families in the analysis, and identifying alternative populations for study. These efforts further restrict attention to narrower regions of the genome, on the order of 100 genes in a particular region linked to the trait. Even with the more narrowly defined linkage region, the number of genes to validate is still unreasonably large. Therefore, research at this stage focuses on identifying candidate genes based on putative function of known or predicted genes in the region and the potential relevance of that function to the trait. This approach is problematic because it is limited to what is currently known about genes. Often, such knowledge is limited and subject to interpretation. As a result, researchers are often led astray and do not identify the genes affecting the trait.

There are many reasons that standard genetic approaches have not proven very successful in the identification of genes associated with traits, such as common human diseases, or the biological pathways associated with such traits. First, common human diseases such as heart disease, obesity, cancer, osteoporosis, schizophrenia, and many others are complex in that they are polygenic. That is, they potentially involve many genes across several different biological pathways and they involve complex gene-environment interactions that obscure the genetic signature. Second, the complexity of the diseases leads to a heterogeneity in the different biological pathways that can give rise to the disease. Thus, in any given heterogeneous population, there may be defects across several different pathways that can give rise to the disease. This reduces the ability to identify the genetic signal for any given pathway. Because many populations involved in genetic studies are heterogeneous with respect to the disease, multiple defects across multiple pathways are operating within the population to give rise to the disease. Third, as outlined above, the genomic regions associated with a linkage to a complex disease are large and often contain a number of genes and possible variants that are potentially associated with the disease. Fourth, the traits and disease states themselves are often not well defined. Therefore, subphenotypes are often overlooked even though these subphenotypes implicate different sets of biological pathways. This reduces the power of detecting the associations. Fifth, even when gene expression and a trait are highly correlated, the genes may not give the same genetic signature. Sixth, in cases where gene expression and a trait are moderately correlated, or not correlated at all, the genes may give rise to the same genetic signature.

In addition to the heterogeneity problems discussed above, the identification of genes and biological pathways associated with traits, such as complex human diseases, using genetics data is confounded, when using human subjects, due to the inability to use common genetic techniques and resources in humans. For example, humans cannot be crossed in controlled experiments. Therefore, there is typically very little pedigree data available for humans. Elucidation of genes associated with complex diseases in humans is also difficult because humans are diploid organisms containing two genomes in each nucleate cell, making it very hard to determine the DNA sequence of the haploid genome. Because of these limitations, genetic approaches to discovering genes and biological pathways associated with complex human diseases is unsatisfactory.

Companies such as deCode Genetics (Reykjavik, Iceland) study populations that are isolated and so are more homogenous with respect to disease, thereby increasing the power to detect association. The disease variations themselves in such populations are greatly reduced as founder effects for many diseases are evident (i.e., specific forms of diseases in such populations most likely arose from a single or small numbers of founders of the population). Other companies, such as Sequenome (San Diego, Calif.), use twin cohorts to study complex diseases. Identical twins are a powerful tool in establishing the genetic component of a trait. The genetic component of a trait is defined as the degree to which a given trait is under genetic control. Dizygotic twins allow for age, gender and environment matching, which helps reduce many of the confounding factors that often reduce the power of genetic studies. In addition, the completion of the human and mouse genomes has made the job of identifying candidate genes in a region of linkage far easier, and it reduces dependency on considering only known genes, since genomic regions can be annotated using ab initio gene prediction software to identify novel candidate genes associated with the disease. Further, the use of demographic, epidemiological and clinical data in more sophisticated models helps explain much of the trait variation in a population. Reducing the overall variation in this way increases the power to detect genetic variation. The identification of millions of SNPs allows finer mapping in any given region of the genome and direct association testing of very large case/control populations, thereby reducing the need to study families and more directly identify the degree to which any genetic variant affects a given population. Finally, our understanding of disease and the need to subphenotype a given disease is now more fully appreciated and aids in reducing the heterogeneity of the disease under study. Technologies such as microarrays have greatly facilitated the ability to subclassify disease subtypes for a given disease. However, all of the methods still fall short when it comes to efficiently identifying genes and pathways associated with complex diseases.

2.2. Identification of a Gene or a Pathway that Affects a Trait Using Gene Expression Data A variety of approaches have been taken to identify genes and pathways that are associated with traits, such as human disease. In one approach, gene expression data is used to attempt to identify genes and pathways associated with such traits. Within the past decade, several technologies have made it possible to monitor the expression level of a large number of transcripts at any one time (see, e.g., Schena et al., 1995, Quantitative monitoring of gene expression patterns with a complementary DNA microarray, *Science* 270:467-470; Lockhart et al., 1996, Expression monitoring by hybridization to high-density oligonucleotide arrays, *Nature Biotechnology* 14:1675-1680; Blanchard et al., 1996, Sequence to array: Probing the genome's secrets, *Nature Biotechnology* 14, 1649; U.S. Pat. No. 5,569,588, issued Oct. 29, 1996 to Ashby et al. entitled "Methods for Drug Screening"). In organisms for which the complete genome is known, it is possible to analyze the transcripts of all genes within the cell. With other organisms for which there is an increasing knowledge of the genome, it is possible to simultaneously monitor large numbers of the genes within the cell.

Such monitoring technologies have been applied to the identification of genes that are up regulated or down regulated in various diseased or physiological states, the analyses of members of signaling cellular states, and the identification of targets for various drugs. See, e.g., Friend and Hartwell, U.S. Pat. No. 6,165,709; Stoughton, U.S. Pat. No. 6,132,969; Stoughton and Friend, U.S. Pat. No. 5,965,352; Friend and Stoughton, U.S. Pat. No. 6,324,479; and Friend and Stoughton, U.S. Pat. No. 6,218,122, all incorporated herein by reference for all purposes.

Levels of various constituents of a cell are known to change in response to drug treatments and other perturbations of the biological state of a cell. Measurements of a plurality of such "cellular constituents" therefore contain a wealth of information about the effect of perturbations and their effect on the biological state of a cell. Such measurements typically comprise measurements of gene expression levels of the type discussed above, but may also include levels of other cellular components such as, but by no means limited to, levels of protein abundances, protein activity levels, or protein interactions. Furthermore, the term "cellular constituents" comprises biological molecules that are secreted by a cell including, but not limited to, hormones, matrix metalloproteinases, and blood serum proteins (e.g., granulocyte colony stimulating factor, human growth hormone, etc.). The collection of such measurements is generally referred to as the "profile" of the cell's biological state. Statistical and bioinformatical analysis of profile data has been used to try to elucidate gene regulation events. Statistical and bioinformatical techniques used in this analysis comprises hierarchical cluster analysis, reference or supervised classification approaches and correlation-based analyses. See, e.g., Tamayo et al., 1999, Interpreting patterns of gene expression with self-organizing maps: methods and application of hematopoietic differentiation, *Proc. Natl. Acad. Sci. U.S.A.* 96:2907-2912; Brown et al., 2000, Knowledge-based analysis of microarray gene expression data by using support vector machines, *Proc. Natl. Acad. Sci. U.S.A.*: 97, 262-267; Gaasterland and Bekinraov, Making the most of microarray data, *Nat. Genet.*: 24, 204-206; Cohen et al., 2000, A computational analysis of whole-genome expression data reveals chromosomal domains of gene expression, *Nat. Genet.* 24: 5-6, 2000.

A problem with such approaches arise when the gene or gene pathway is only active in a tissue type that is not readily susceptible to gene expression level measurements. For example, if the gene or pathway associated with a complex disease is only active in a tissue such as brain or lung, animals must be sacrificed in order to obtain the expression data from the brain. For this and other reasons, the elucidation of genes involved in biological pathways that influence a trait, such as a disease, using gene expression approaches is expensive, problematic and generally not successful in many instances.

2.3. Monitoring the Activity of a Gene or Key Genes in a Pathway Associated with a Trait As indicated above, once a gene or a biological pathway has been identified that affects a trait of interest, it is still necessary to obtain compounds or other molecular entities that affect the activity of the gene or critical compounds in the biological pathway in order to achieve a clinically desired outcome. Affected activity, for example, can take the form of an alteration in the expression level of a gene, enzymatic activity of a gene product, phosphorylation state of a gene product, or three-dimensional conformation of a gene product. In some instances, the goal is to increase the activity of the gene or gene pathway component. One such example is the rescue of p53 activity in the cancerous state. In other instances, the goal is to decrease the activity of the gene or gene pathway component. An example where this is desirable is the inhibition of matrix metalloproteinases associated with inflammation.

Each gene that affects a complex disease can typically be purified and assayed for activity against a library of compounds or other molecular entities (e.g. other gene products, transcription factors, protein-based inhibitors, antibodies, etc.). While data from such assays is useful, in vivo assays, in which the activity of the gene is measured in an organism provides an improved indicator of the potency of compounds or other molecular entities. However, in many instances, the targeted gene is only expressed in a tissue type that is not readily obtainable. For example, if the relevant gene activity only occurs in the brain, the test organism needs to be sacrificed in order to obtain activity data for the gene. Such activity data includes, but is not limited to, expression data for the gene, enzymatic activity of the corresponding gene product, and the amount of gene product in the target tissue. Thus, a significant drawback to known drug discovery methods is the expense of obtaining in vivo gene activity data.

In addition to its utility in drug discovery applications, in vivo gene activity data has substantial diagnostic purposes. The sequencing of the human genome and other scientific advances has lead to the increasing discovery of the role that specific genes have in certain diseased states. Thus, in vivo gene activity data can be used as a diagnostic indicator of the likelihood of contracting specific diseases as well as disease progression. However, similar to the drug discovery case, the problem with known gene discovery techniques is that in vivo gene activity data is difficult to obtain in instances where the relevant activity occurs in a tissue that is either difficult to obtain.

Given the above background, what is needed in the art are improved methods for identifying genes and biological pathways that affect traits such as diseases. Further, what is needed in the art are improved methods for measuring the in vivo activity of genes and components of biological pathways.

Discussion or citation of a reference herein will not be construed as an admission that such reference is prior art to the present invention.

3. SUMMARY OF THE INVENTION

The present invention addresses the shortcomings in the known art. Computer systems and methods for identifying genes and pathways associated with traits are provided. Advantageously, the computer systems and methods of the present invention are able to identify genes that affect a trait as a result of their activity in a target tissue using the expression patterns of genes in a secondary tissue. Furthermore, once a target gene has been identified that affects a trait as a result of the activity of the gene or its gene product in a target tissue, the expression patterns of genes in a secondary tissue can be used to monitor the activity of the gene. This monitoring can be used to facilitate a drug discovery program, a clinical trial, or for diagnostic purposes.

One aspect of the present invention provides a method of identifying a plurality of cellular constituents in a predetermined secondary tissue of a species that serve as surrogate markers for the activity of a target gene in a primary tissue of the species. In this embodiment, the target gene affects a trait. Levels of a plurality of cellular constituents in the predetermined secondary tissue in a plurality of organisms of the species are measured. The plurality of organisms exhibit a genetic variance with respect to the trait under study. A set of cellular constituents in the plurality of cellular constituents that exhibits a pattern of levels that associate with the complex trait is identified. The set of cellular constituents serve as the surrogate markers for the activity of the target gene.

Another aspect of the invention provides methods for identifying a set of cellular constituents in a secondary tissue of a species that serves as a surrogate marker for an activity of a target gene expressed in a primary tissue of said species. A classifier is constructed using a cellular constituent level of each cellular constituent in a first plurality of cellular constituents measured in the secondary tissue in each member of a population of the species. The population comprises a first subgroup and a second subgroup. The classifier is based on a second plurality of cellular constituents that comprises all or a portion of the first plurality of cellular constituents. Respective abundance levels of each cellular constituent in the second plurality of cellular constituents varies between the first subgroup and the second subgroup. All or a portion of the population of the species is classified into a plurality of subtypes using the classifier. One or more cellular constituents is identified that can discriminate members of the population between a first subtype in the plurality of subtypes and a second subtype in the plurality of subtypes, thereby identifying the set of cellular constituents.

In some embodiments, trait is a clinical trait that does not exhibit classic Mendelian inheritance. In some instances, the clinical trait is an amount of the gene product of the target gene that is in the blood of the plurality of organisms. In some embodiments, the trait is a complex disease such as asthma, ataxia telangiectasia, bipolar disorder, cancer, common late-onset Alzheimer's disease, diabetes, hereditary early-onset Alzheimer's disease, maturity-onset diabetes of the young, mellitus, migraine, nonalcoholic fatty liver, obesity, polycystic kidney disease, psoriases, schizophrenia, steatohepatitis or xeroderma pigmentosum.

In some embodiments, prior to the measuring, all or a portion of the plurality of organisms of the species are exposed to a perturbation that affects the trait This perturbation can be environmental, such as exposure to a compound, exposure to an allergen, exposure to pain, exposure to a hot temperature, exposure to a cold temperature, a diet, sleep deprivation, isolation, or an exercise regimen. Alternatively, the perturbation is genetic, such as a gene knockout, exposure to an inhibitor of a gene product, N-ethyl-N-nitrosourea mutagenesis, or siRNA knockdown of a gene.

In some embodiments, the plurality of cellular constituents is mRNA, cRNA or cDNA and the measuring of levels of the plurality of cellular constituents comprises measuring the transcriptional state of all or a portion of the plurality of cellular constituents in the predetermined secondary tissue. In some embodiments, the plurality of cellular constituents is proteins and the measuring of the levels of the plurality of cellular constituents comprises measuring the translational state of all or a portion of the plurality of cellular constituents in the predetermined secondary tissue. In some embodiments, all or a portion of the plurality of cellular constituents are separated using two-dimensional gel electrophoresis or fluorescence two-dimensional difference gel electrophoresis to produce an electropherogram that is then analyzed by a mass spectrometric technique, Western blotting and immunoblot analysis using antibodies, internal microsequencing, or N-terminal microsequencing. In some embodiments, the levels of all or a portion of the plurality of cellular constituents is determined using isotope-coded affinity tagging followed by tandem mass spectrometry analysis. In still other embodiments, the measuring of the levels of the plurality of cellular constituents comprises measuring the activity or post-translational modifications of all or a portion of the plurality of cellular constituents in the predetermined secondary tissue.

In some embodiments, prior to the measuring, a first portion of the plurality of organisms are exposed to a perturbation that affects the trait and a second portion of the plurality of organisms are not exposed to the perturbation. In such embodiments, the finding of the levels of the set of cellular constituents comprises determining those cellular constituents whose levels in the predetermined secondary tissue discriminate the first portion of the plurality of organisms from the second portion of the plurality of organisms. In some embodiments, the discrimination between the first portion of the plurality of organisms and the second portion of the plurality of organisms based on the pattern of levels of the set of cellular constituents is determined by a correlation analysis, a t-test, a paired t-test, analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

In some embodiments, the plurality of organisms includes a first portion of organism that do not exhibit the trait and a second portion of organism that exhibit the trait. In such embodiments, the finding of the set of cellular constituents comprises determining those cellular constituents whose levels in said predetermined secondary tissue discriminate the first portion of the plurality of organisms from the second portion of said plurality of organisms. This discrimination between the first portion of the plurality of organisms and the second portion of the plurality of organisms can be determined by a correlation analysis, a t-test, a paired t-test, analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

In some embodiments the trait is a clinical trait that does not exhibit classic Mendelian inheritance and the plurality of organisms exhibit variance with respect to the clinical trait. In such embodiments, identification of the set of cellular constituents comprises determining those cellular constituents in the plurality of cellular constituents that discriminate the variance with respect to the clinical trait that is exhibited by the plurality of organisms. This discrimination can be determined by a correlation analysis, an analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

In some embodiments the plurality of cellular constituents comprises between fifty and five hundred cellular constituents, between three hundred and one thousand cellular constituents, between eight hundred and five thousand cellular constituents, between four thousand and fifteen thousand cellular constituents, between ten thousand and forty thousand cellular constituents, or between fifty and five hundred cellular constituents. In some embodiments, the set of cellular constituents comprises between three hundred and one thousand cellular constituents, between eight hundred and five thousand cellular constituents, between four thousand and fifteen thousand cellular constituents, or between ten thousand and forty thousand cellular constituents.

In some embodiments the finding a pattern set of cellular constituents whose levels in the secondary tissue associate with the trait further comprises clustering a plurality of cellular constituent vectors thereby creating a plurality of clusters. Each cellular constituent vector in said plurality of cellular constituent vectors represents a cellular constituent in the plurality of cellular constituents. Each cellular constituent vector in the plurality of cellular constituent vectors comprises a plurality of cellular constituents levels. Each cellular constituent level in the plurality of cellular constituent levels is a level of the cellular constituent represented by the vector in the secondary tissue of a different organism in the plurality of organisms. Then a cluster that most closely associates with the trait is identified.

In some embodiments, the clustering comprises agglomerative hierarchical clustering using Pearson correlation coefficients. In some embodiments the clustering comprises a hierarchical clustering technique, a k-means technique, a fuzzy k-means technique, a Jarvis-Patrick clustering technique, a self-organizing map, or a neural network. In some embodiments, the clustering is a nearest neighbor agglomerative algorithm, a farthest-neighbor agglomerative algorithm, an average linkage agglomerative algorithm, a centroid agglomerative algorithm, or a sum-of-squares agglomerative algorithm. In some embodiments the clustering is a polythetic divisive clustering procedure or a monthetic divisive clustering procedure. In still other embodiments, the clustering is a nonparametric clustering procedure. In some embodiments, the nonparametric clustering procedure is Spearman R clustering, Kendall Tau clustering, or Gamma coefficient clustering.

In some embodiments, prior to the measuring, a first portion of the plurality of organisms are exposed to a perturbation that affects the trait and a second portion of the plurality of organisms are not exposed to the perturbation. In such instances, the determining step comprises identifying a cluster that represents cellular constituents whose levels in the predetermined secondary tissue discriminate the first portion of the plurality of organisms from the second portion of the plurality of organisms. This discrimination can be, for example, a correlation analysis, a t-test, a paired t-test, analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

In some embodiments, the plurality of organisms includes a first portion of organism that do not exhibit the trait and a second portion of organism that exhibit the trait. In such instances, the determining the first cluster comprises identifying a cluster representing cellular constituents whose levels in the predetermined secondary tissue discriminate the first portion of the plurality of organisms from the second portion of the plurality of organisms. This discrimination can be determined, for example, by a correlation analysis, a t-test, a paired t-test, analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

In some embodiments, the trait is a clinical trait that does not exhibit classic Mendelian inheritance and the plurality of organisms exhibit variance with respect to the clinical trait. In such instances, the determining the first cluster comprises identifying a cluster representing cellular constituents that discriminate the variance with respect to the clinical trait that is exhibited by the plurality of organisms.

In one aspect of the invention, the identity of the target gene in the primary tissue of the species is not known and the method further comprises:

(i) for each cellular constituent in all or a portion of the cellular constituents in the set of cellular constituents or all or a portion of the cellular constituents in the first cluster, performing quantitative genetic analysis using an abundance statistic for the cellular constituent as a quantitative trait in the quantitative genetic analysis, the abundance statistic comprising a measurement of the level of the cellular constituent in the secondary tissue of each organism in the plurality of organisms, thereby identifying a hot spot chromosomal region of the genome of the species that links to one or more cellular constituents in the species; and (ii) identifying a plurality of genes that are in the hot spot chromosomal region;

(iii) for each gene in a plurality of genes in the hot spot region, performing quantitative genetic analysis using the gene; and (iv) ranking each gene identified in the hot spot based on the quantitative genetic analyses performed in step (iii) to form a ranked list of genes.

In some embodiments, each quantitative genetic analysis in step (i) and step (iii) uses a genetic marker map, wherein the genetic marker map is constructed from a set of genetic markers associated with the species. In some embodiments, measurement of the level of the cellular constituent in the secondary tissue of each organism in the plurality of organisms that is used in step (i) to form the abundance statistic is a measurement of the transcriptional state of the cellular constituent, the translational state of the cellular constituent, the activity or a post-translational modification of the cellular constituent.

In some embodiments, each quantitative genetic analysis performed in step (i) comprises model-free linkage analysis. In some embodiments, each quantitative genetic analysis performed in step (i) comprises mode-free linkage analysis such as, for example, identical by descent affected pedigree member analysis (IBD-APM) or identical by state affected pedigree analysis (IBS-APM). In some embodiments, each quantitative genetic analysis performed in step (i) comprises association analysis such as population-based association analysis or family-based association analysis. In some embodiments, each quantitative genetic analysis performed in step (i) comprises a haplotype relative risk test, a transmission equilibrium test, or a sibship-based test.

In some embodiments each quantitative genetic analysis performed in step (iii) comprises (A) testing for linkage or association between a position in the genome of the species and the quantitative trait, wherein the quantitative trait is a measurement of the level of the gene corresponding to the quantitative genetic analysis in each organism in the plurality of organisms;

(B) advancing to another position in the genome; and (C) repeating steps (A) and (B) until an end of the genome is reached.

In some embodiments, the measurement of the level of the gene in each organism in the plurality of organisms is a measurement of the transcriptional state of the gene, the translational state of the gene, the activity of the gene or a post-translational modification of the gene. In some embodiments the testing step (A) comprises performing model-free linkage analysis. In some embodiments the testing step (A) comprises performing model-free linkage analysis such as identical by descent affected pedigree member analysis (IBD-APM) or identical by state affected pedigree analysis (IBS-APM). In some embodiments, the testing step (A) comprises association analysis such as population-based association analysis. In some embodiments, the testing step (A) comprises family-based association analysis such as a haplotype relative risk test, a transmission equilibrium test, or a sibship-based test.

In some embodiments the method of the present invention further comprises using a plurality of genes in the ranked list of genes in a multivariate analysis to determine whether said genes are genetically interacting.

Another aspect of the present invention provides a computer program product for use in conjunction with a computer system. The computer program product comprises a computer readable storage medium and a computer program mechanism embedded therein. The computer program mechanism comprises a classification module for identifying a plurality of cellular constituents in a predetermined secondary tissue of a species that serve as surrogate markers for the activity of a target gene in a primary tissue of the species. The target gene affects a trait. The classification module comprises instructions for finding a pattern of levels of a set of cellular constituents that associate with the trait. The levels of the plurality of cellular constituents are from the predetermined secondary tissue in a plurality of organisms of the species. Furthermore, the plurality of organisms exhibit a genetic variance with respect to the trait.

Yet another aspect of the invention provides a computer system for identifying a plurality of cellular constituents in a predetermined secondary tissue of a species that serve as surrogate markers for the activity of a target gene in a primary tissue of the species. The target gene affects a trait. The computer system comprises a central processing unit and a memory coupled to the central processing unit. The memory stores a classification module. The classification module comprises instructions for finding a pattern of levels of a set of cellular constituents that associate with the trait. The levels of the plurality of cellular constituents are from the predetermined secondary tissue in a plurality of organisms of the species. The plurality of organisms exhibit a genetic variance with respect to the trait.

4. BRIEF DESCRIPTION OF THE DRAWINGS

FIGS. 2A and 2B illustrate processes for identifying patterns of expression from secondary tissues that are associated with a trait in accordance with various embodiments of the present invention.

Figure 5:
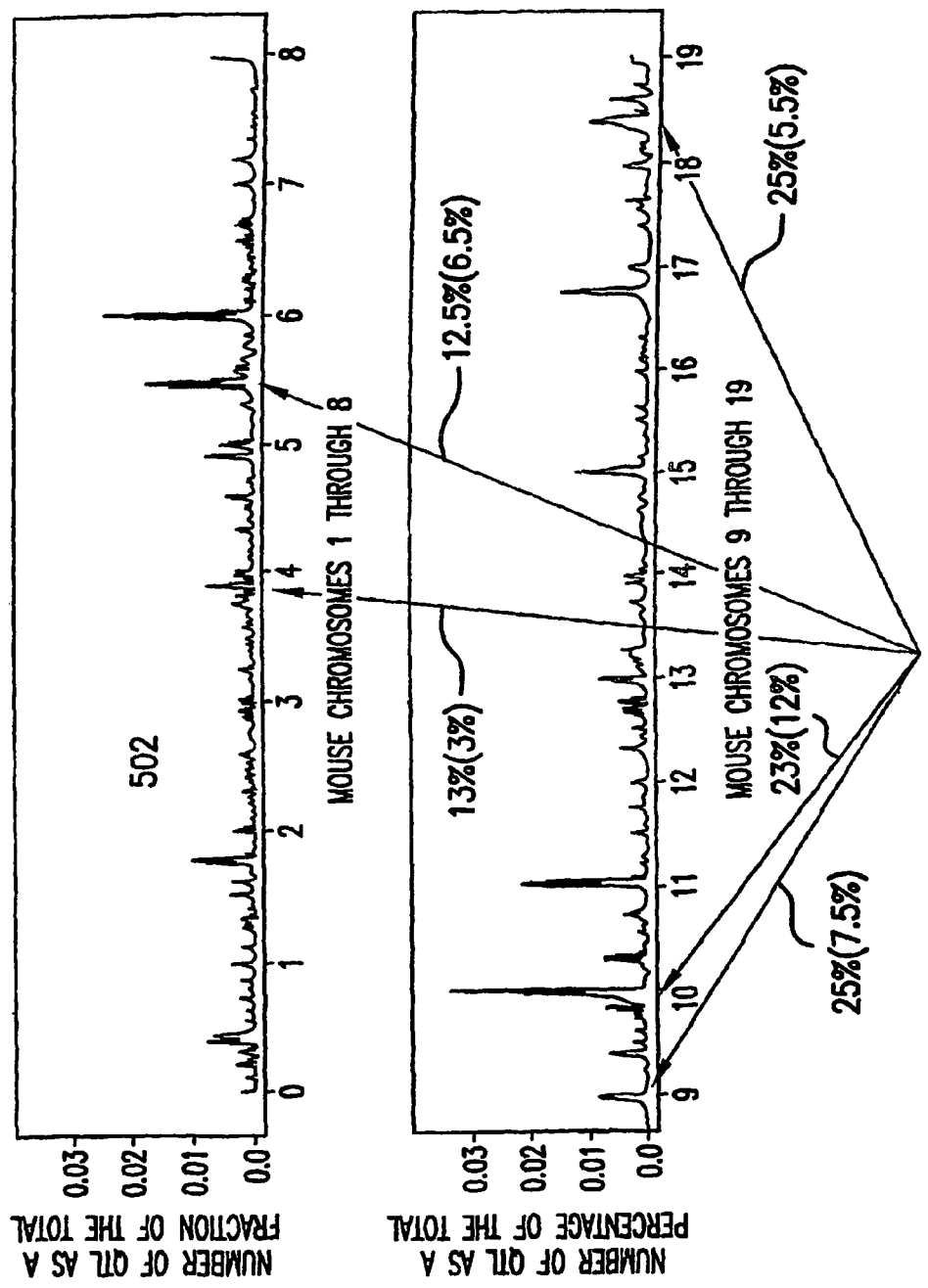

FIG. 5 plots the percentage of eQTL at different lod score thresholds across 920 evenly-spaced bins, each 2 cM wide, covering the mouse genome in a quantitative genetic analysis performed in accordance with one embodiment of the present invention.

Figure 6:
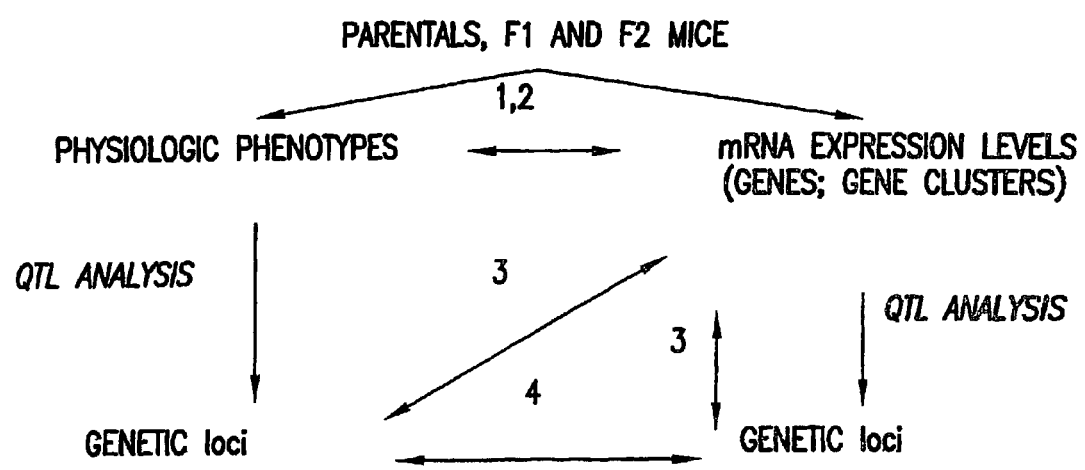

FIG. 6 illustrates genetic crosses used to derive a mouse model for a complex human disease in accordance with one embodiment of the present invention.

Figure 7:
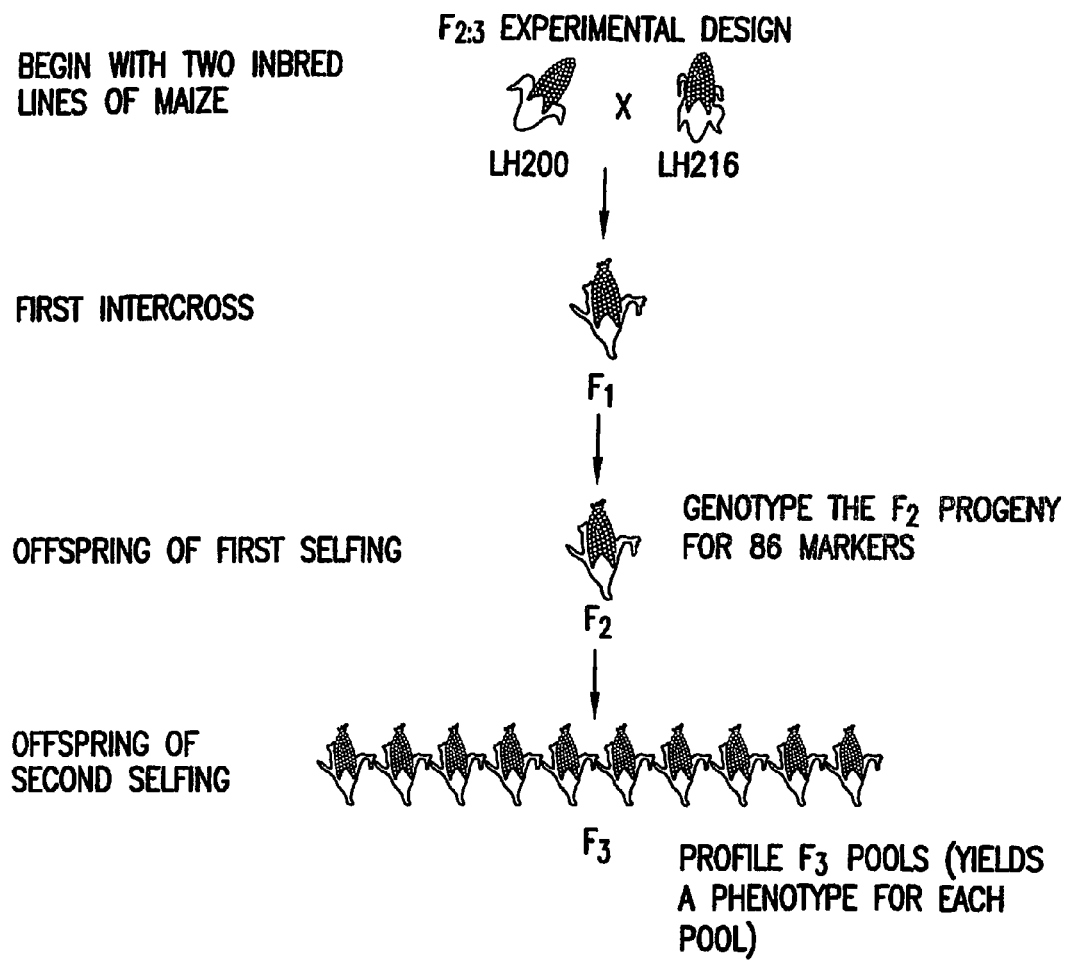

FIG. 7 illustrates data based on an experimental cross done in Zea mays in order to yield suitable genotype and pedigree data in accordance with one embodiment of the present invention.

Figure 8:
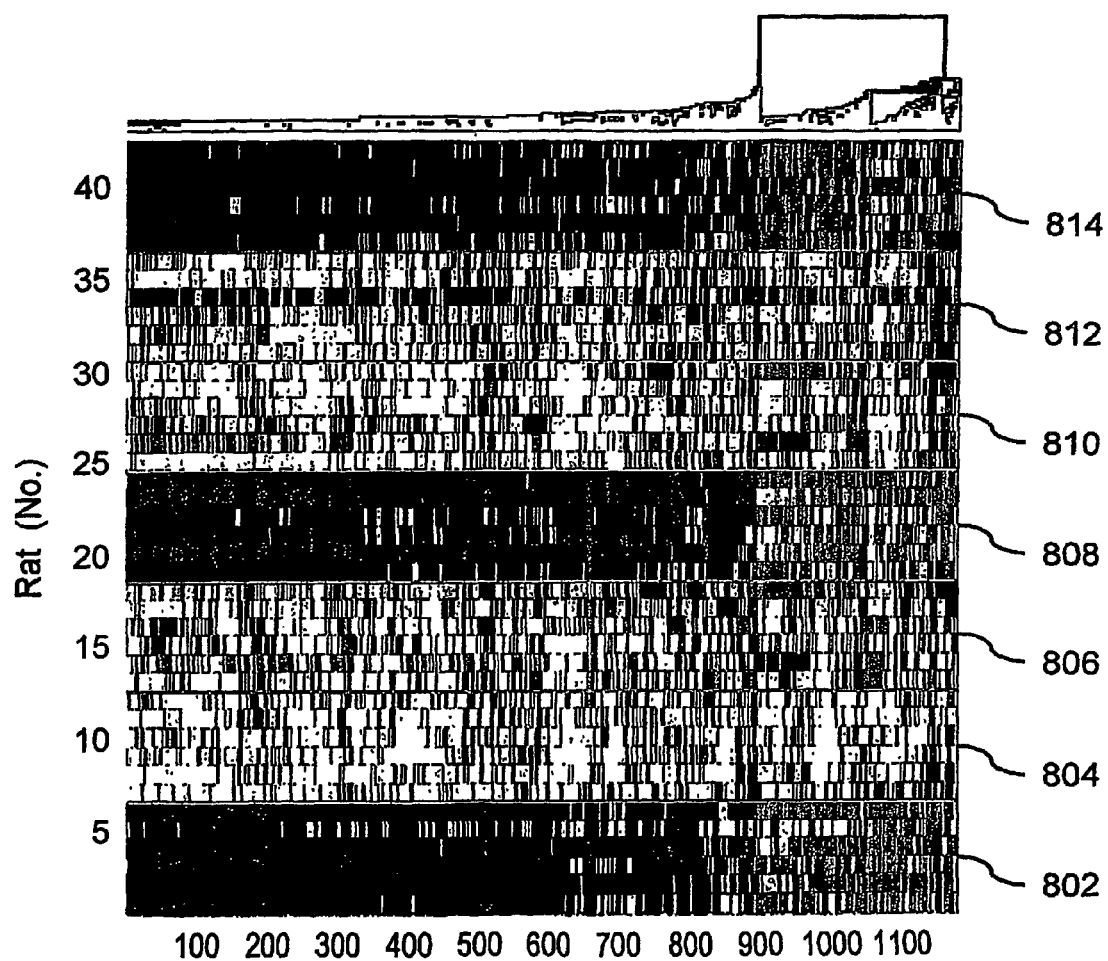

FIG. 8 illustrates microarray data from an experiment designed to determine which genes are differentially expressed when the model organism is exposed to an $MC_4$ receptor agonist, in accordance with one embodiment of the present invention.

Figure 9:
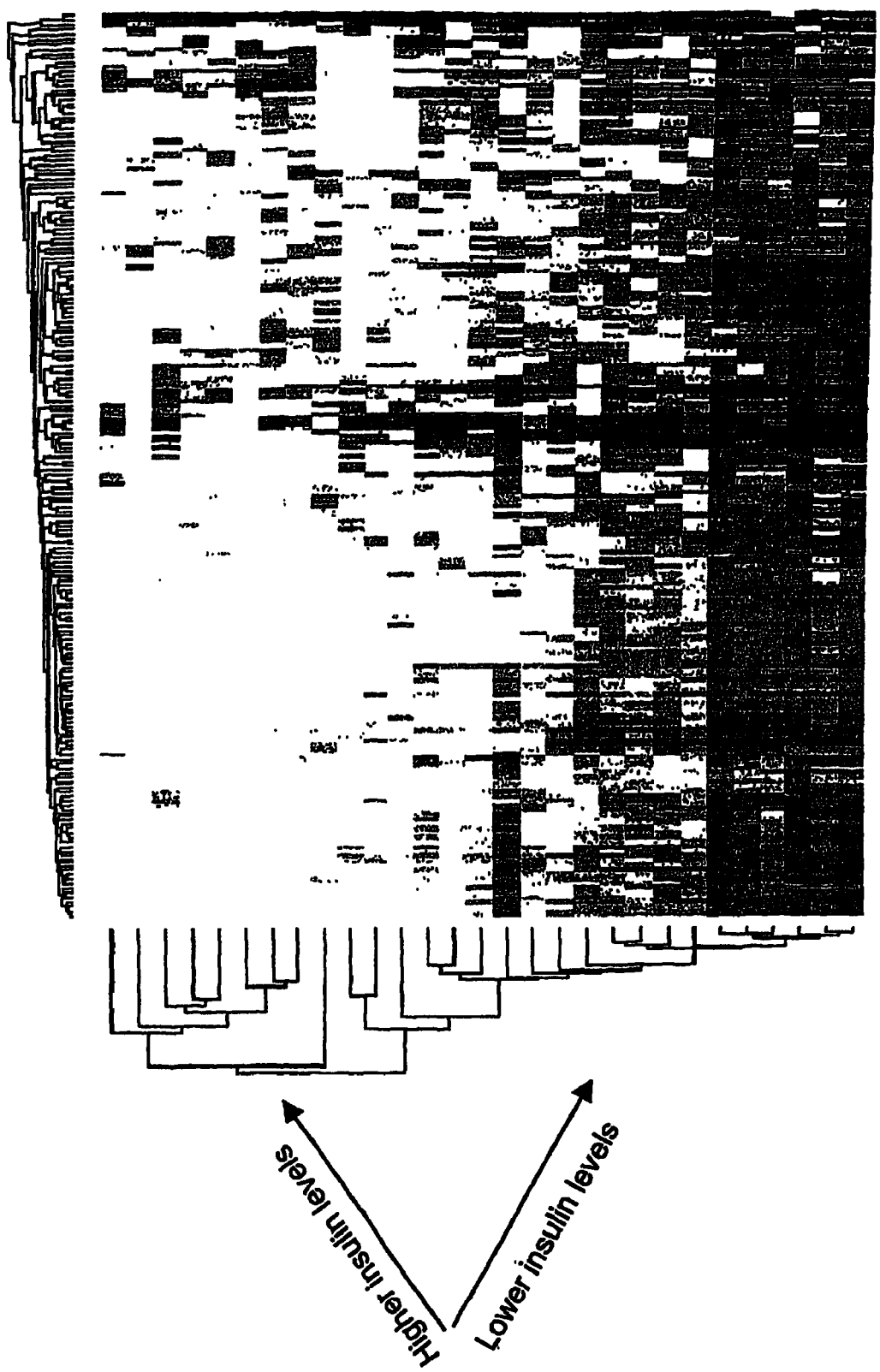

FIG. 9 illustrates microarray data from an experiment designed to determine which genes are differentially expressed in the pancreas as a function of insulin level in the liver, in accordance with one embodiment of the present invention.

Figure 10:
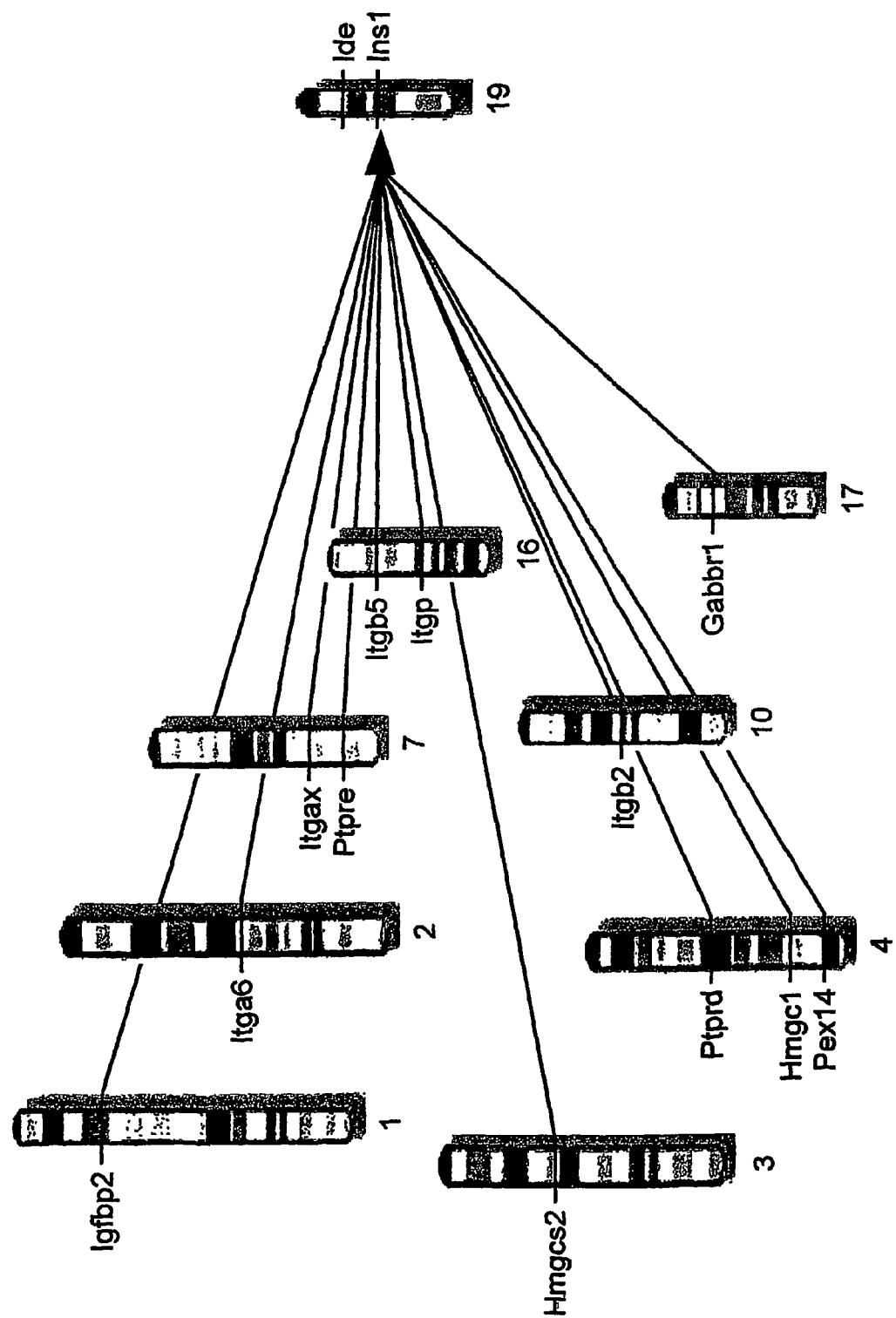

FIG. 10 illustrates the genes linking to the insulin locus that are physically located on chromosomes other than chromosome 19.

FIG. 11 illustrates a data structure that comprises that data used to identify cellular constituents that discriminate a trait under study.

Figure 12:
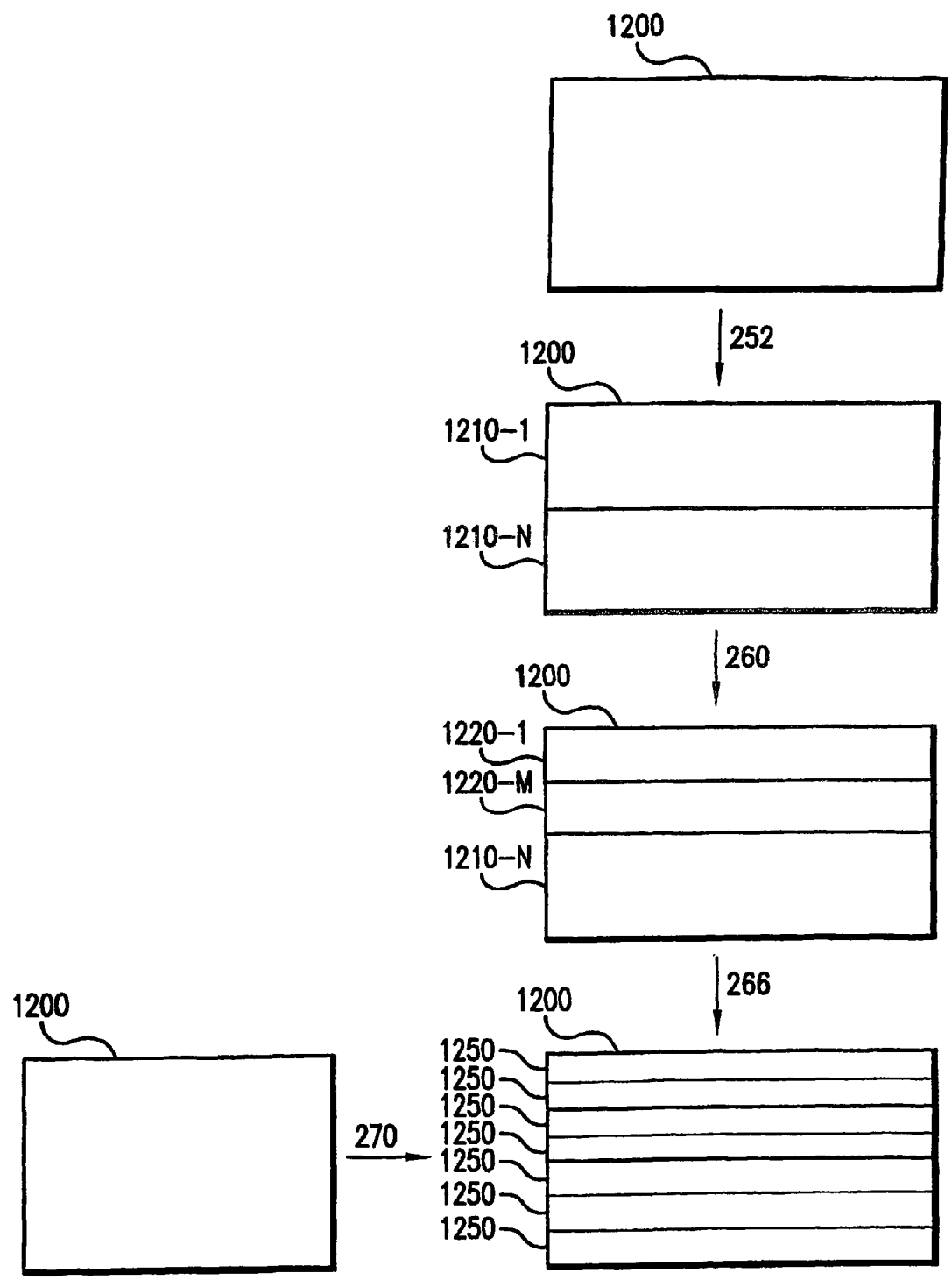

FIG. 12 illustrates the classification of a trait of interests into subtraits in accordance with one embodiment of the present invention.

Figure 13:
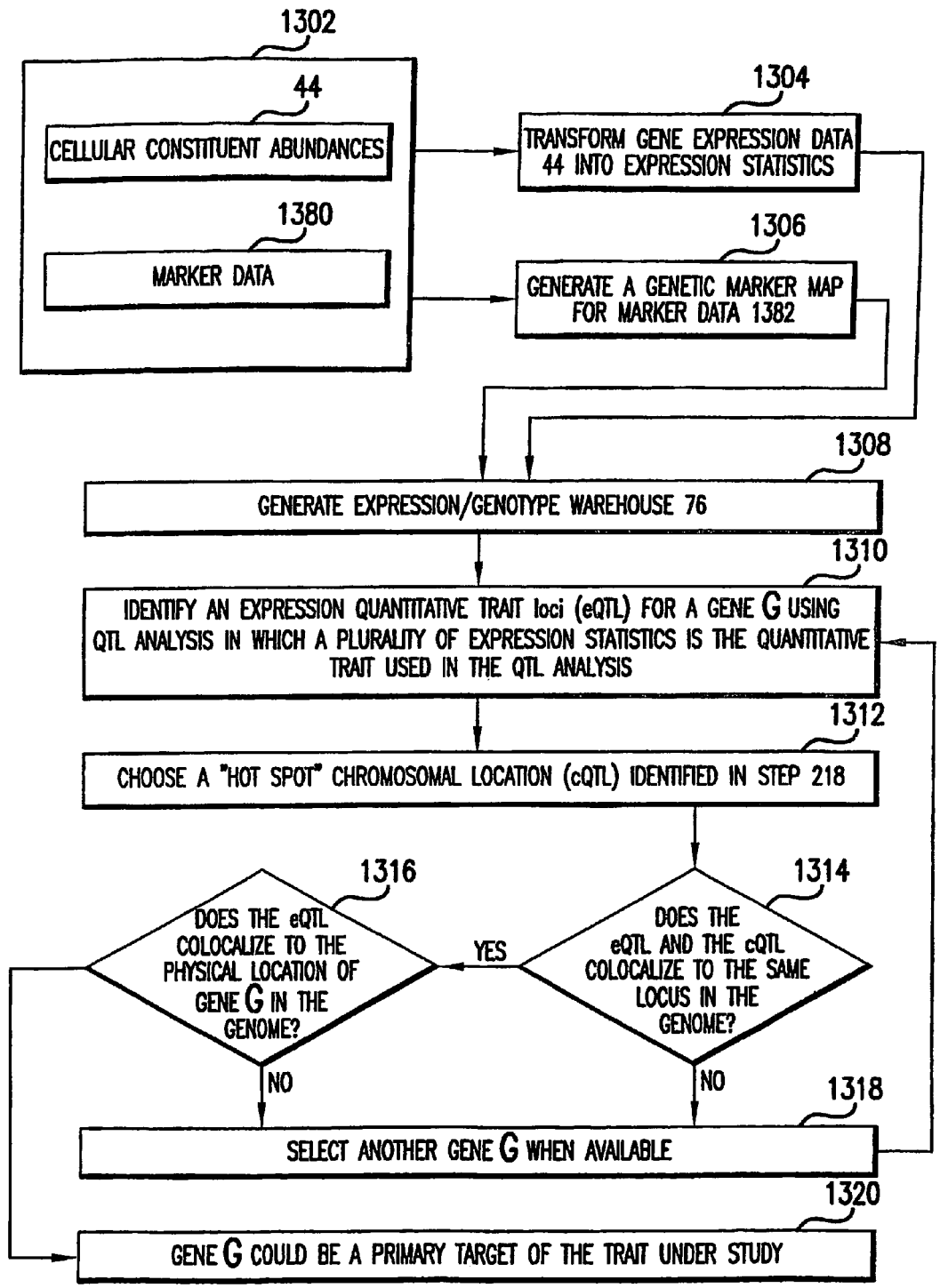

FIG. 13 illustrates processing steps in accordance with one embodiment of the present invention.

Like reference numerals refer to corresponding parts throughout the several views of the drawings.

5. DETAILED DESCRIPTION

One of the central missions of drug discovery is to identify genes and pathways associated with traits using gene expression profiles in the context of well-designed experiments aimed at elucidating the trait of interest. The types of traits of interest are broad and include, but are not limited to, complex disease status (e.g., diabetes, obesity, atherosclerosis, etc.), quantitative measures of risk traits associated with complex diseases (e.g., insulin levels, BMI, airway hyperresponsiveness, etc.), lifestyle or behavior related traits (e.g., smoking, alcohol use, drug use, depression, etc.), adverse drug response and drug efficacy, or exposure to a drug. More information on traits that are considered using the computer systems and methods of the present invention are discussed in Section 5.11, below.

Complex traits involve multiple genetic and environmental factors that can interact in complex ways. However, from the standpoint of experimental design, these traits are often treated in the same way with respect to the analysis. For instance, in seeking to associate natural genetic variation with a complex trait, it doesn't matter whether the trait is a disease trait like obesity or diabetes, or a drug response trait like adverse drug response or efficacy, the methods to establish such an association are essentially identical.

The types of experiments designed for these purposes are diverse and include looking at genetic and environmental factors associated with the trait. Experiments focused on the genetic dissection of a trait can involve associating natural genetic variation with the trait of interest See, for example, U.S. patent application Ser. No. 60/436,684, titled "COMPUTER SYSTEMS AND METHODS FOR ASSOCIATING GENES WITH TRAITS USING CROSS SPECIES DATA" inventors Schadt and Monks, filed Dec. 27, 2002, which is incorporated by reference in its entirety. Alternatively, experiments focused on the genetic dissection of a trait can involve artificial manipulations such as gene knockouts, N-Ethyl-N-nitrosourea (ENU) mutagenesis, siRNA knockdown of a gene, or targeting a gene using drug therapies. Similarly, experiments that involve associating environmental variation with variation in gene expression or other similar measurements, will involve natural environmental influences (e.g., smoking, diet, exercise, etc.) and artificial environmental influences (e.g., drug treatment, pain stimulus, etc.). Gene expression data can greatly facilitate the identification of genes and pathways associated with the traits of interest. See, for example, U.S. patent application Ser. No. 10/356,857, titled "COMPUTER SYSTEMS AND METHODS FOR IDENTIFYING GENES AND DETERMINING PATHWAYS ASSOCIATED WITH TRAITS" inventors Schadt and Monks, filed Feb. 3, 2003; U.S. patent application Ser. No. 60/382,036 filed May 20, 2002; and U.S. patent application Ser. No. 60/400,522 filed Aug. 2, 2002. However, as described in Section 2 above, the tissue or tissues (primary tissues) most relevant to the trait of interest, (e.g., the tissue or tissues from which expression array profiling will maximize chances of identifying genes and pathways associated with the trait) are not always easily accessible. For example, brain tissue is not easily accessible because it requires the sacrifice of the model organism. In such instances, the instant invention advantageously relies upon secondary tissues that are once or more removed from the primary tissues with respect to the genetic or environmental causal factors driving the expression pattern of interest. It has been unexpectedly discovered that such tissues can exhibit patterns of expression that associate with the trait of interest. In such instances, the present invention uses the patterns of expression from the secondary tissues as a surrogate for those patterns in the primary tissue that are associated with the trait of interest.

5.1. Overview of the Invention

The present invention provides systems and methods for identifying a plurality of cellular constituents in a predetermined secondary tissue of a species that serve as surrogate markers for the activity of a target gene in a primary tissue of the species. As used here, the primary and secondary tissues are tissues in the species so long as they are different. For example, the primary tissue can be brain and the secondary tissue can be the liver. In fact, the secondary tissue can be blood. The target gene affects a trait. In typical embodiments, the primary tissue is the tissue where the target gene affects this trait.

Levels of a plurality of cellular constituents in the predetermined secondary tissue in a plurality of organisms of the species are measured. The plurality of organisms is any collection of organisms of the species that exhibits a genetic variance with respect to the trait. Next, a pattern of levels of a set of cellular constituents that associate with the trait is identified. This set of cellular constituents serves as surrogate markers for the activity of the target gene. The set of cellular constituents that serve as surrogate markers is highly advantageous because the activity of the primary gene can be monitored without measuring the transcriptional, translational or activity state of the target gene in the primary tissue. In some embodiments, more than one pattern is identified. For instance, in some embodiments, there could be variation in response to a compound hitting a target.

The systems and methods of the present are particularly advantageous in the case where the target gene has not been identified. Even in the case where the target gene remains unidentified, the surrogate markers can be used to track the state (e.g., transcriptional, translational, or activity) of the target gene in the primary tissue. In fact, the systems and methods of the present invention can use the surrogate markers to identify the target gene that affects the trait in the primary tissue in cases where the target gene is unknown or the primary tissue is not readily available.

Figure 1:
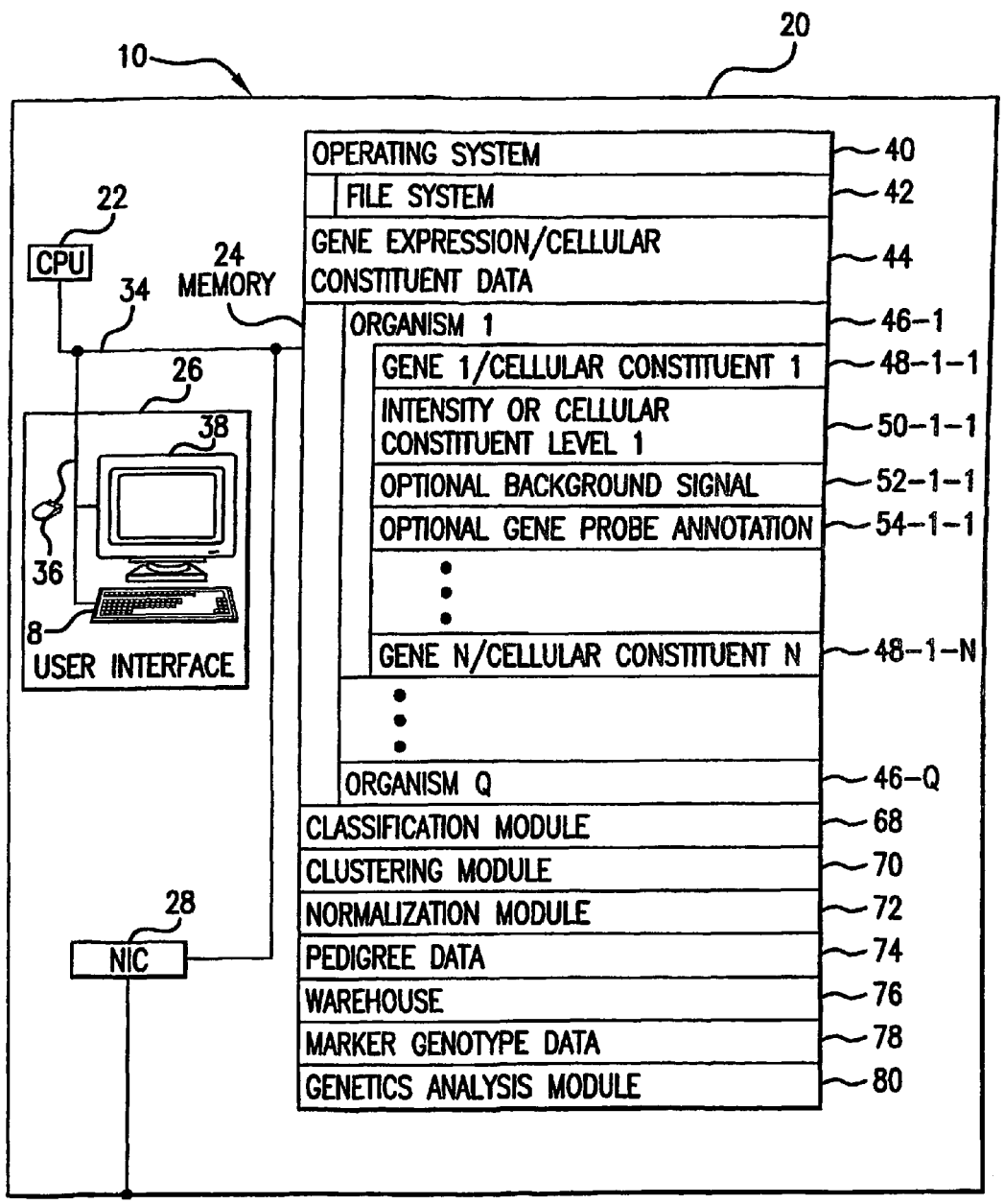
FIG. 1 illustrates a computer system for discovering and/or monitoring the activity of a gene in a target tissue using the expression patterns of a set of genes in a secondary tissue in accordance with one embodiment of the present invention.
Figure 2B:
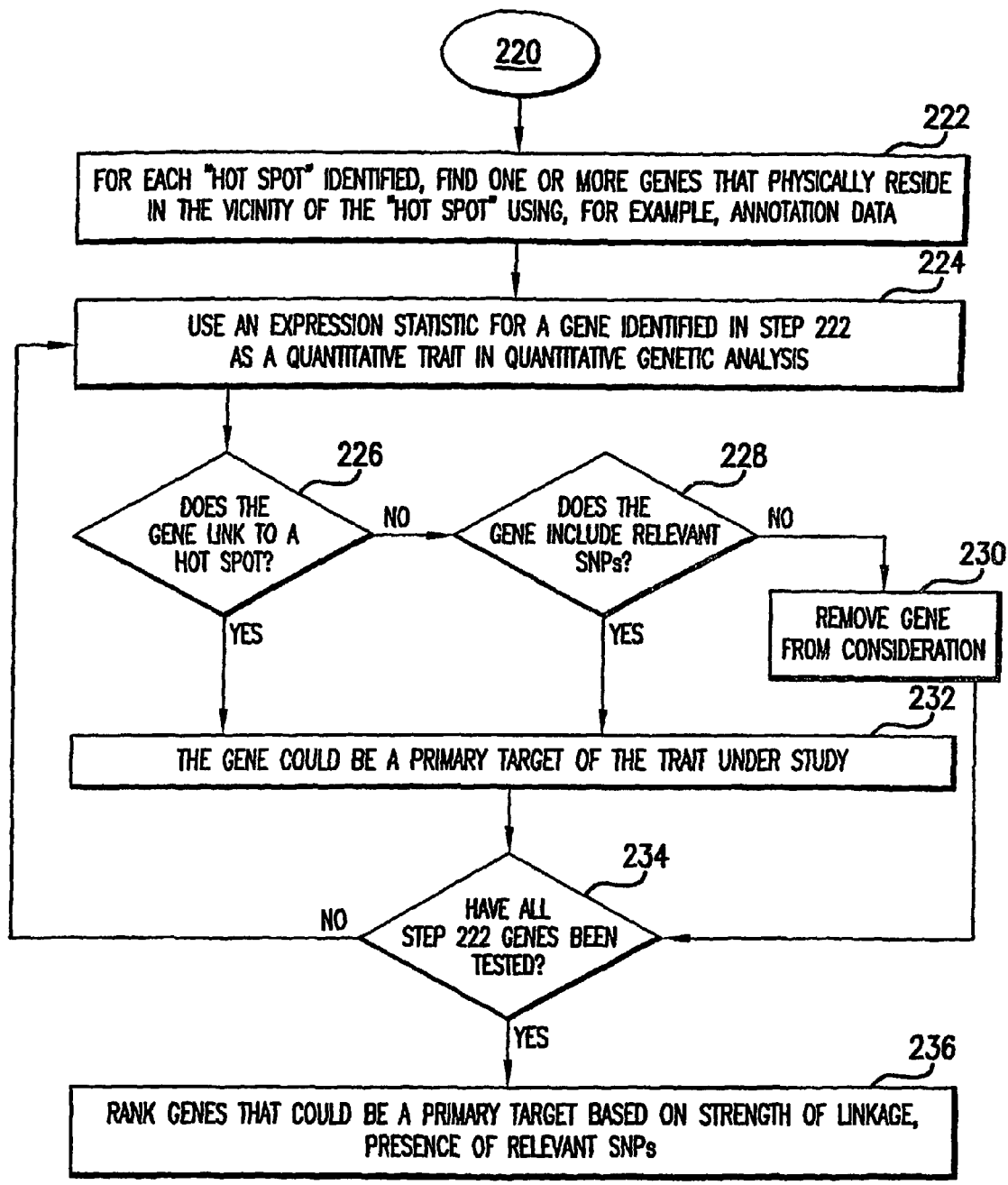
Figure 2C:
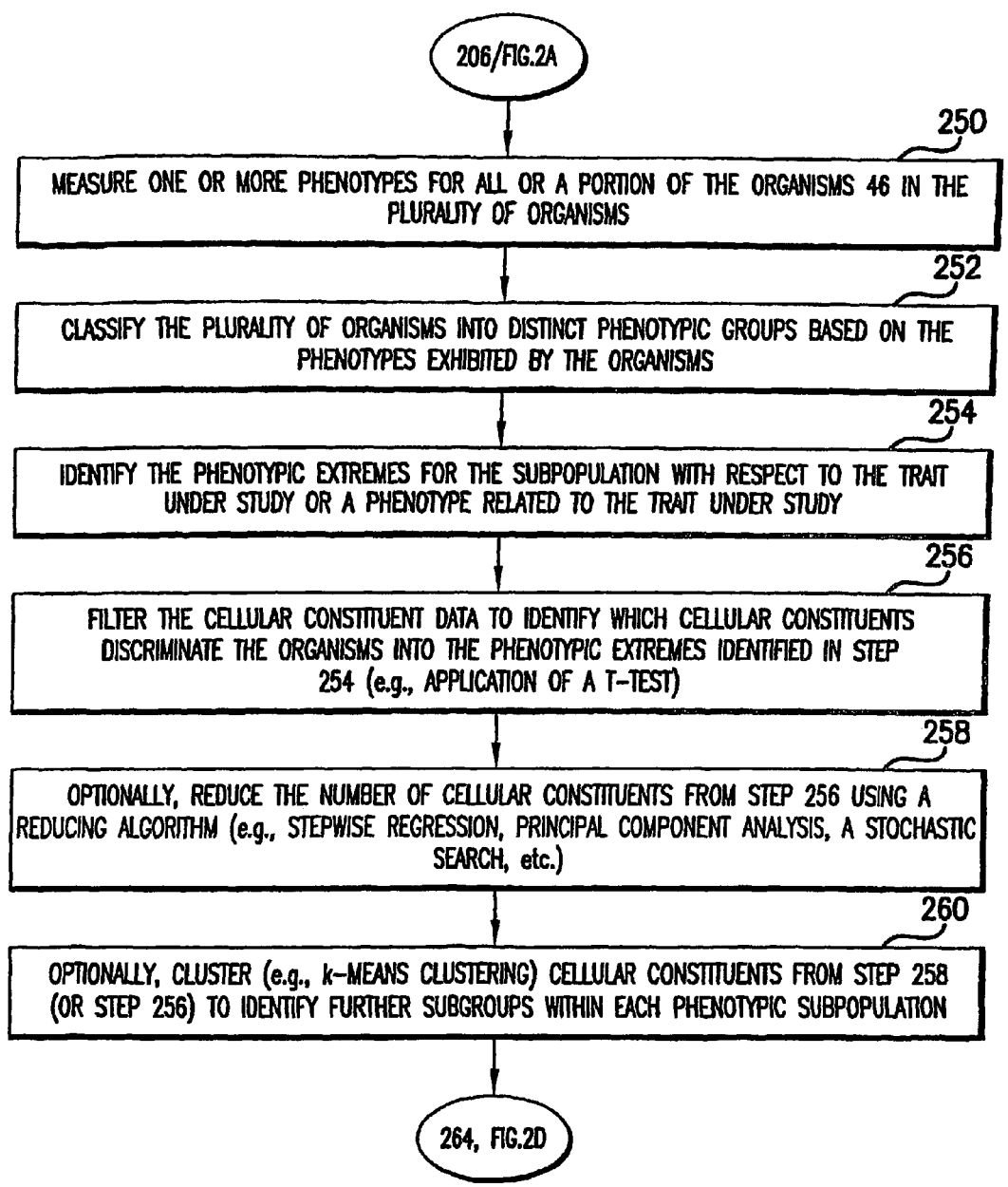
FIGS. 2C and 2D illustrate processes for identifying patterns of expression from secondary tissues that are associated with a trait in accordance with various embodiments of the present invention.
Figure 2D:
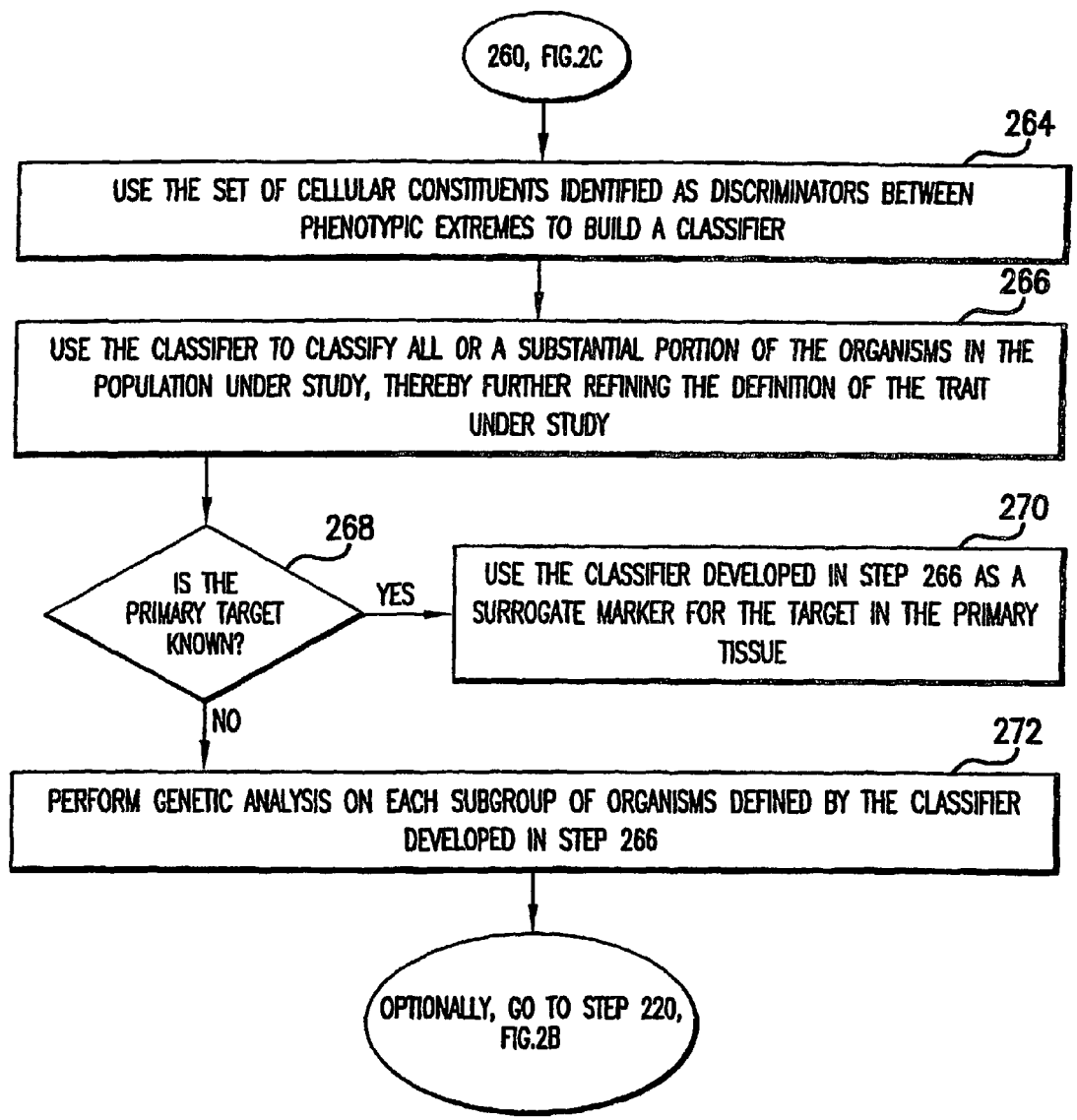

FIG. 1 illustrates a system 10 that is operated in accordance with one embodiment of the present invention. FIGS. 2A and 2B illustrate the processing steps that are performed in accordance with a specific embodiment of the present invention. FIGS. 2C and 2D illustrate alternative processing steps that are performed in accordance with a more generalized approach in accordance with the present invention. These figures will be referenced in this section in order to disclose the advantages and features of the present invention.

5.1.1 System Architecture

System 10 comprises at least one computer 20 (FIG. 1). Computer 20 comprises standard components including a central processing unit 22, memory 24 (including high speed random access memory as well as non-volatile storage, such as disk storage) for storing program modules and data structures, user input/output device 26, a network interface 28 for coupling server 20 to other computers via a communication network (not shown), and one or more busses 34 that interconnect these components. User input/output device 26 comprises one or more user input/output components such as a mouse 36, display 38, and keyboard 8.

Memory 24 comprises a number of modules and data structures that are used in accordance with the present invention. It will be appreciated that, at any one time during operation of the system, a portion of the modules and/or data structures stored in memory 24 is stored in random access memory while another portion of the modules and/or data structures is stored in non-volatile storage. In a typical embodiment, memory 24 comprises an operating system 40. Operating system 40 comprises procedures for handling various basic system services and for performing hardware dependent tasks. Memory 24 further comprises a file system 42 for file management. In some embodiments, file system 42 is a component of operating system 40.

5.1.2 Clustering Method

Step 202.

In step 202 (FIG. 2A), a trait is selected for study in a species. In some embodiments, the trait is a complex trait. The species can be a plant, animal, human, or bacteria. In some embodiments, the species is human, cat, dog, mouse, rat, monkey, pigs, *Drosophila*, or corn. The trait can be affected by levels of one or more target genes (e.g., the transcriptional state of the target gene, the translational state of the target gene product, the activity of the target gene product, etc.) in a tissue that is typically not readily accessible for measurement (for example, on an outpatient basis). This tissue is referred to herein as the primary tissue. Subsequent steps in FIG. 2A are directed to the identification of an expression pattern in a secondary tissue that can be used as a substitute for information on the state of the target gene in the primary tissue.

In some embodiments, a plurality of organisms representing the species is studied. The number of organisms in the species can be any number. In some embodiments, the plurality of organisms studied is between 5 and 100, between 50 and 200, between 100 and 500, or more than 500 organisms. In some embodiments, the plurality of organisms are an $F_2$ intercross, a $F_t$ population (formed by randomly mating $F_1$s for t−1 generations), an $F_{2:3}$ design ($F_2$ individuals are genotyped and then selfed), or a Design III ($F_2$ from two inbred lines are backcrossed to both parental lines). Thus, in some embodiments of the present invention, organisms 46 represent a population, such as an $F_2$ population, an $F_t$ population, an $F_{2:3}$ population or a Design III population.

In some embodiments, a portion of the organisms under study are subjected to a perturbation that affects the trait. The perturbation can be environmental or genetic. Examples of environmental perturbations include, but are not limited to, exposure of an organism to a test compound, an allergen, pain, and hot or cold temperatures. Additional examples of environmental perturbations include diet (e.g. a high fat diet or low fat diet), sleep deprivation, isolation, and quantifying natural environmental influences (e.g., smoking, diet, exercise). Examples of genetic perturbations include, but are not limited to, the use of gene knockouts, introduction of an inhibitor of a predetermined gene or gene product, N-Ethyl-N-nitrosourea (ENU) mutagenesis, siRNA knockdown of a gene, or quantifying a trait exhibited by a plurality of organisms of a species. Various siRNA knock-out techniques (also referred to as RNA interference or post-transcriptional gene silencing) are disclosed, for example, in Xia, et al, 2002, Nature Biotechnology 20, p. 1006; Hannon, 2002, Nature 418, p. 244; Carthew, 2001, Current Opinion in Cell Biology 13, p. 244; Paddison, 2002, Genes & Development 16, p. 948; Paddison & Hannon, 2002, Cancer Cell 2, p. 17; Jang et al., 2002, Proceedings National Academy of Science 99, p. 1984; and Martinez et al, 2002, Proceedings National Academy of Science 99, p. 14849.

In general, the perturbation that is optionally used in step 202 is designed to help discover one or more gene targets in a primary tissue that affects the trait under study. As such, the perturbation optionally used in step 202 is selected because of some relationship between the perturbation and the trait. For example, the perturbation could be the siRNA knockdown of a gene that is thought to influence the trait under study. Examples of traits that can be studied in the systems and methods of the present invention are disclosed in Section 5.11, below. It will be appreciated that the one or more target genes can interact differently in different genetic backgrounds within the same species. For example, one strain of mouse will have one type of a response to a given compound, while another strain of mouse will have a different response.

In some embodiments, particularly in those cases where the genes that affect the trait under study are not known, it may not be known in advance which tissues are primary tissues and which tissues are secondary tissues. As defined herein, primary tissues are those tissues in which the expression of genes that affect or cause the trait of interest have their primary effect on the trait of interest. Secondary tissues are those tissues in which the expression of genes that affect or cause the trait of interest, do not significantly or directly affect the trait of interest. In fact, it is possible that genes that affect or cause the trait of interest may not even be expressed in the secondary tissues. In such embodiments, the following steps are performed without knowledge of which tissue is a secondary tissue and which tissue is a primary tissue. Then, genetic methods outlined in steps 218-236 below are used to identify the target genes underlying the trait (or perturbation) of interest. Once the target genes have been identified, a simple examination of the expression of the target over the different tissues profiled would allow for the identification of the primary tissue.

Step 204.

In step 204 (FIG. 2A), the levels of cellular constituents in secondary tissue are measured from the plurality of organisms 46 in order to derive gene expression/cellular constituent data 44. The identity of the primary and secondary tissue will be dependent on what is known about the trait under study. In some embodiments, the trait under study is known to affect a primary tissue, such as the brain. Further, in some embodiments, hypotheses are formed about what secondary tissues may be affected by the trait under study. Thus, primary and secondary tissue selection in the present invention is done on a case by case basis using known information about the trait under study. In some embodiments, several different secondary tissues are tested using the techniques described herein until a suitable secondary tissue is found. A suitable secondary tissue is one that can serve as a surrogate for the primary tissue under the methods of the present invention.

Generally, the plurality of organisms 46 exhibit a genetic variance with respect to the trait. In some embodiments, the trait is quantifiable. For example, in instances where the trait is a disease, the trait can be quantified in a binary form (e.g., "1" if the organism has contracted the disease and "0" if the organism has not contracted the disease). In some embodiments, the trait can be quantified as a spectrum of values and the plurality of organisms 46 will represent several different values in such a spectrum. In some embodiments, the plurality of organisms 46 comprise an untreated (e.g., unexposed, wild type, etc.) population and a treated population (e.g., exposed, genetically altered, etc.). In some embodiments, for example, the untreated population is not subjected to a perturbation whereas the treated population is subjected to a perturbation. In some embodiments, the secondary tissue that is measured in step 204 is blood, white adipose tissue, or some other tissue that is easily obtained from organisms 46.

In varying embodiments, the levels of between 5 cellular constituents and 100 cellular constituents, between 50 cellular constituents and 100 cellular constituents, between 300 and 1000 cellular constituents, between 800 and 5000 cellular constituents, between 4000 and 15,000 cellular constituents, between 10,000 and 40,000 cellular constituents, or more than 40,000 cellular constituents are measured.

In one embodiment, gene expression/cellular constituent data 44 comprises the processed microarray images for each individual (organism) 46 in a population under study. In some embodiments, such data comprises, for each individual 46, intensity information 50 for each gene/cellular constituent 48 represented on the microarray, optional background signal information 52, and associated annotation information 54 describing the gene probe (FIG. 1). In some embodiments, cellular constituent data 44 is, in fact, protein expression levels for various proteins in a particular secondary tissue in organisms 46 under study.

In one aspect of the present invention, cellular constituent levels are determined in step 204 by measuring an amount of the cellular constituent in a predetermined secondary tissue of the organism. As used herein, the term "cellular constituent" comprises individual genes, proteins, mRNA expressing genes, metabolites and/or any other cellular components that can affect the trait under study. The level of a cellular constituent can be measured in a wide variety of methods. Cellular constituent levels, for example, can be amounts or concentrations in the secondary tissue, their activities, their states of modification (e.g., phosphorylation), or other measurements relevant to the trait under study.

In one embodiment, step 204 comprises measuring the transcriptional state of cellular constituents 48 in the secondary tissue of organisms 46. The transcriptional state includes the identities and abundances of the constituent RNA species, especially mRNAs, in the secondary tissue. In this case, the cellular constituents are RNA, cRNA, cDNA, or the like. The transcriptional state of the cellular constituents can be measured by techniques of hybridization to arrays of nucleic acid or nucleic acid mimic probes, or by other gene expression technologies. Transcript arrays are discussed in Section 5.8, below.

In another embodiment, step 204 comprises measuring the translational state of cellular constituents 48 in secondary tissue. In this case, the cellular constituents are proteins. The translational state includes the identities and abundances of the proteins in the secondary tissue. In one embodiment, whole genome monitoring of protein (e.g., the "proteome," Goffeau et al., 1996, Science 274, p. 546) can be carried out by constructing a microarray in which binding sites comprise immobilized, preferably monoclonal, antibodies specific to a plurality of protein species encoded by the secondary tissue. Preferably, antibodies are present for a substantial fraction of the encoded proteins. Methods for making monoclonal antibodies are well known. See, for example, Harlow and Lane, 1998, Antibodies: A Laboratory Manual, Cold Spring Harbor, N.Y. In one embodiment, monoclonal antibodies are raised against synthetic peptide fragments designed based on genomic sequences of the secondary tissue. With such an antibody array, proteins from the secondary tissue are contacted with the array and their binding is assayed with assays known in the art. In some embodiments, antibody arrays for high-throughput screening of antibody-antigen interactions are used. See, for example, Wildt et al., Nature Biotechnology 18, p. 989.

Alternatively, large scale quantitative protein expression analysis can be performed using radioactive (e.g., Gygi et al., 1999, Mol. Cell. Biol 19, p. 1720) and/or stable iostope ($^{15}$N)

metabolic labeling (e.g., Oda et al. Proc. Natl. Acad. Sci. USA 96, p. 6591) followed by two-dimensional (2D) gel separation and quantitative analysis of separated proteins by scintillation counting or mass spectrometry. Two-dimensional gel electrophoresis is well-known in the art and typically involves focusing along a first dimension followed by SDS-PAGE electrophoresis along a second dimension. See, e.g., Hames et al, 1990, *Gel Electrophoresis of Proteins: A Practical Approach*, IRL Press, New York; Shevchenko et al, 1996, Proc Nat'l Acad. Sci. USA 93, p. 1440; Sagliocco et al., 1996, Yeast 12, p. 1519; Lander 1996, Science 274, p. 536; and Naaby-Haansen et al., 2001, TRENDS in Pharmacological Science 22, p. 376. Electropherograms can be analyzed by numerous techniques, including mass spectrometric techniques, western blotting and immunoblot analysis using polyclonal and monoclonal antibodies, and internal and N-terminal microsequencing. See, for example, Gygi, et al., 1999, Nature Biotechnology 17, p. 994. In some embodiments, fluorescence two-dimensional difference gel electrophoresis (DIGE) is used. See, for example, Beaumont et al., Life Science News 7, 2001. In some embodiments, quantities of proteins in the secondary tissue of organisms 46 are determined using isotope-coded affinity tags (ICATs) followed by tandem mass spectrometry. See, for example, Gygi et al., 1999, Nature Biotech 17, p. 994. Using such techniques, it is possible to identify a substantial fraction of the proteins expressed in a predetermined secondary tissue in organisms 46.

In other embodiments, step 204 comprises measuring the activity or post-translational modifications of the cellular constituents in the predetermined secondary tissues of the plurality of organisms 46. See for example, Zhu and Snyder, Curr. Opin. Chem. Biol 5, p. 40; Martzen et al., 1999, Science 286, p. 1153; Zhu et al., 2000, Nature Genet. 26, p. 283; and Caveman, 2000, J. Cell. Sci. 113, p. 3543. In some embodiments, measurement of the activity of the cellular constituents is facilitated using techniques such as protein microarrays. See, for example, MacBeath and Schreiber, 2000, Science 289, p. 1760; and Zhu et al., 2001, Science 293, p. 2101. In some embodiments, post-translational modifications or other aspects of the state of cellular constituents are analyzed using mass spectrometry. See, for example, Aebersold and Goodlett, 2001, Chem Rev 101, p. 269; Petricoin III, 2002, The Lancet 359, p. 572.

In some embodiments, the proteome of the secondary tissue is analyzed in step 204. The analysis of the proteome of cells in the secondary tissue (e.g., the quantification of all proteins and the determination of their post-translational modifications) typically involves the use of high-throughput protein analysis methods such as microarray technology. See, for example, Templin et al., 2002, TRENDS in Biotechnology 20, p. 160; Albala and Humphrey-Smith, 1999, Curr. Opin. Mol. Ther. 1, p. 680; Cahill, 2000, *Proteomics: A Trends Guide*, p. 47-51; Emili and Cagney, 2000, Nat. Biotechnol., 18, p. 393; and Mitchell, Nature Biotechnology 20, p. 225.

In still other embodiments, "mixed" aspects of the amounts cellular constituents are measured in step 204. In one example, the amounts or concentrations of one set of cellular constituents in the secondary tissue are combined with measurements of the activities of certain other cellular constituents in the secondary tissue in step 204.

In some embodiments, different allelic forms of a cellular constituent in a given organism are detected and measured in step 204. For example, in a diploid organism, there are two copies of any given gene, one descending from the "father" and the other from the "mother." In some instances, it is possible that each copy of the given gene is expressed at different levels. This is of significant interest since this type of allelic differential expression could associate with the trait under study, particularly in instances where the trait under study is complex.

Step 206.

Once gene expression/cellular constituent data 44 has been obtained, the data is transformed (FIG. 2A, step 206) into expression statistics. In some embodiments, cellular constituent data 44 (FIG. 1) comprises transcriptional data, translational data, activity data, and/or metabolite abundances for a plurality of cellular constituents. In one embodiment, the plurality of cellular constituents comprises at least five cellular constituents. In another embodiment, the plurality of cellular constituents comprises at least one hundred cellular constituents, at least one thousand cellular constituents, at least twenty thousand cellular constituents, or more than thirty thousand cellular constituents.

The expression statistics commonly used as quantitative traits in the analyses in one embodiment of the present invention include, but are not limited to, the mean log ratio, log intensity, and background-corrected intensity derived from transcriptional data. In other embodiments, other types of expression statistics are used as quantitative traits.

In one embodiment, this transformation (FIG. 2A, step 206) is performed using normalization module 72 (FIG. 1). In such embodiments, the expression level of each of a plurality of genes in each organism under study is normalized. Any normalization routine can be used by normalization module 72. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be run. Exemplary normalization routines in accordance with the present invention are disclosed in more detail in Section 5.3, below. The expression statistics formed from the transformation are optionally stored in warehouse 76.

Step 208.

In step 208, patterns of cellular constituent levels (e.g., gene expression levels, protein abundance levels, etc.) are identified that associate with the trait under study and/or the perturbation that is optionally applied in step 202. There are several ways that step 208 can be carried out, and all such ways are included within the scope of the present invention. Typically, step 208 is performed by classification module 68. One such method first identifies those cellular constituents 48 that discriminate the trait.

In one example, a perturbation is applied in step 202. The perturbation can be, for example, exposure of the organism to a compound. Exposure of the organism to a compound can be effected by a variety of means, including but not limited to, administration, injection, etc. In this example, the population of organisms 46 is divided into two classes. Those organisms 46 that have been exposed to the compound and those organisms 46 that have not been exposed to the compound. In the example, those cellular constituents (e.g. genes, proteins, metabolites, etc.) whose levels (e.g., transcriptional state, translational state, activity state, post-translational modification state, etc.) in the secondary tissues of the organisms 46 discriminate the treatment group (the group exposed to the organism) from the control group are identified using a statistical technique such as a paired t-test, an unpaired t-test, a Wilcoxon rank test, a signed rank test, or by computation of the correlation between the trait and gene expression values. In some instances, the perturbation optionally applied in step 202 comprises multiple treatments. In such instances, generalizations to the t-test and ranks tests, such as Anova or Kruskal-Wallis, are used in this step.

In another embodiment, a perturbation is not applied in step 202. In one case, the population under study is divided into those organisms 46 that exhibit the trait and those organisms that do not exhibit the trait. Those cellular constituents (e.g. genes, proteins, metabolites, etc.) whose abundances (e.g., transcriptional state, translational state, activity state, post-translational modification state, etc.) in the secondary tissues of the organisms 46 discriminate the affected group from the unaffected group are identified using a statistical technique.

In still other embodiments, the population under study is divided into groups based on a function of the phenotype for the trait under study. Those cellular constituents whose levels in the secondary tissues of the organisms 46 discriminate between the various groups are identified using a statistical technique. For more details on the statistical techniques that can be used in step 208, see Section 5.15, below.

In another example, the population under study exhibits a broad spectrum of phenotypes for the trait. Those cellular constituents whose levels in the secondary tissues of the organism 46 that can differentiate at least some of these phenotypes are then identified using statistical techniques. Generally speaking, in this step, the population is divided into phenotypically distinct groups and cellular constituents that distinguish between these phenotypically distinct groups are identified using statistical tests such as a t-tests (for two groups) or ANOVA (for greater than two groups).

In various embodiments, the set of cellular constituents 48 identified in step 208 comprises between 5 and 100 cellular constituents, between 50 and 500 cellular constituents, between 400 and 1000 cellular constituents, between 800 and 4000 cellular constituents, between 3000 and 8000 cellular constituents, 8000 to 15000 cellular constituents, more 15000 cellular constituents, or less than 30000 cellular constituents.

In some embodiments, the phenotypic extremes within the population are identified. For example, in one case, the trait of interest is obesity. In such an example, very obese and very skinny organisms 46 are selected as the phenotypic extremes in this step. In one embodiment of the present invention, a phenotypic extreme is defined as the top or lowest $40^{th}$, $30^{th}$, $20^{th}$, or $10^{th}$ percentile of the population with respect to a given phenotype exhibited by the population. In some embodiments, cellular constituent levels 50 (measured in phenotypically extreme organisms) for a given cellular constituent 46 are subjected to a t-test or some other test such as a multivariate test to determine whether the given cellular constituent 46 can discriminate between phenotypic groups identified (e.g., treated versus untreated) for the population under study. A cellular constituent 46 will discriminate between phenotypic groups when the cellular constituent is found at characteristically different levels in each of the phenotypic groups. For example, in the case where there are two phenotypic groups, a cellular constituent will discriminate between the two groups when levels 50 of the cellular constituent (measured in phenotypically extreme organisms) are found at a first level in the first phenotypic group and are found at a second level in the second phenotypic group, where the first and second level are distinctly different.

Step 210.

Once the set of cellular constituents 48 that discriminate the trait or, optionally, the perturbation, have been identified (e.g., using organisms in the population that represent phenotypic extremes), they can be clustered using clustering module 70. In one embodiment of the present invention, each cellular constituent 48 in the set of cellular constituents that discriminates the trait (or the perturbation applied in step 202) between two or more classes (e.g., afflicted versus nonafflicted, perturbed versus nonperturbed) is treated as a cellular constituent vector. For example, the $n^{th}$ cellular constituent 48 in the set of cellular constituents that discriminates the perturbation (e.g., complex trait) between two or more classes is represented as:

$$C_n = (A_1^n, A_2^n, \ldots, A_m^n)$$

where each A is the level (e.g., transcriptional state, translational state, activity, etc.) of cellular constituent n in the secondary tissue of an organism 46 in the plurality of organisms under study, and m is the number of organisms considered. Cellular constituent vectors $C_n$ can be clustered based on similarities in the values of corresponding levels A in each cellular constituent vector. Cellular constituent vector $C_n$, will cluster into the same group (cellular constituent vector cluster) if the corresponding levels in such cellular constituent vectors are correlated. To illustrate, consider hypothetical cellular constituent vectors $C_n$, that are obtained by measuring three different cellular constituents in five different organisms 46. Each cellular constituent vector will therefore have five values. Each of the five values will be a level (e.g., activity, transcriptional state, translational state, etc.) of the corresponding cellular constituent n in the secondary tissue of one of the five organisms 46:

Exemplary cellular constituent vector $C_1$: {0, 5, 5.5, 0, 0}
Exemplary cellular constituent vector $C_2$: {0, 4.9, 5.4, 0, 0}
Exemplary cellular constituent vector $C_3$: {6, 0, 3, 3, 5}

Thus, for vector $C_1$, there is a level of cellular constituent "$C_1$" of 0 arbitrary units in the first organism, 5 arbitrary units in the second organism, 5.5 arbitrary units in the third organism, and 0 arbitrary units in the fourth and fifth organisms. Clustering of exemplary cellular constituent vectors $C_1$, $C_2$, and $C_3$ will result in two clusters (cellular constituent vector clusters). The first cluster will include cellular constituent vectors $C_1$ and $C_2$ because there is a correlation in the levels within each vector (0 versus 0 in organism 46-1, 5 versus 4.9 in organism 46-2, 5.5 versus 5.4 in organism 46-3, 0 versus 0 in organism 46-4, and 0 versus 0 in organism 46-5). The second cluster will consists of exemplary cellular constituent vector $C_3$ because the pattern of levels in vector $C_3$ is not similar to the pattern of levels in $C_1$, and $C_2$. This illustration serves to describe certain aspects of clustering using hypothetical cellular constituent level data. However, in some embodiments of the present invention, the cellular constituents used in this step are selected because they discriminate trait extremes. Thus, unlike the hypothetical data shown above, the cellular constituent levels should reflect that they were selected over phenotypic extremes in some embodiments of the present invention. When this is the case, the clustering in this step will help to identify subgroups of cellular constituents within the group of cellular constituents that discriminate trait extremes.

In one embodiment of the present invention, agglomerative hierarchical clustering is applied to the cellular constituent vectors in step 210. In such clustering, similarity is determined using Pearson correlation coefficients between the cellular constituent vector pairs. In other embodiments, the clustering of the cellular constituent vectors comprises application of a hierarchical clustering technique, application of a k-means technique, application of a fuzzy k-means technique, application of a Jarvis-Patrick clustering technique, application of a self-organizing map or application of a neural network. In some embodiments, the hierarchical clustering technique is an agglomerative clustering procedure. In other embodiments, the agglomerative clustering procedure is a nearest-neighbor algorithm, a farthest-neighbor algorithm, an average linkage algorithm, a centroid algorithm, or a sum-of-squares algorithm. In still other embodiments, the hierarchical clustering technique is a divisive clustering procedure. Illustrative clustering techniques that can be used to cluster gene analysis vectors are described in Section 5.5, below. In preferred embodiments, nonparamatric clustering algorithms are applied to the cellular constituent vectors. In some embodiments, Spearman R, Kendall Tau, or Gamma coefficients are used to cluster the cellular constituent vectors.

Step 212.

In step 212, the population is reclassified into subtypes using the clustering information from step 210. The goal of step 212 is to construct a classifier that comprises those cellular constituents that can distinguish between these subtypes. In one embodiment, a respective phenotypic vector is constructed for each organism in the population. Each phenotypic vector comprises the cellular constituent levels for all or a portion of the set of cellular constituents that were used in step 210. In some embodiments, the order of the elements in the phenotypic vectors is determined by the clustering patterns achieved in step 210.

The phenotypic vectors are clustered using any of the techniques described in Section 5.5. In embodiments where the order of the elements in each phenotypic vector is determined based on the clustering in step 210, the clustering in step 212 produces a two-dimensional cluster. In one dimension, cellular constituents are clustered based on similarities in their abundance across the population of organisms. For example, two cellular constituents would cluster together if they are expressed at similar levels throughout the population. On the other dimension, organisms are clustered based on similarity in cellular constituent expression across the set of cellular constituents. For example, two organisms will cluster together in the second dimension if the cellular constituents in each organism express at comparable levels.

The present invention provides many alternative pattern classification techniques that can be used instead of the clustering techniques that are described in steps 210 and 212. These alternative pattern classification techniques can be used to build classifiers from discriminating cellular constituents. Such classifiers can then be used to differentiate the general population into distinct subgroups. Such alternative techniques are described in Section 5.1.3.

In essence, the clustering in steps 210 and 212 order the population into new subgroups (e.g., phenotypic clusters). Each subgroup (phenotypic cluster) is characterized by a distinctive cellular constituent expression (or level) pattern. To illustrate, consider the case in which the clustering performed in step 210 produces three groups of cellular constituents, namely groups A, B and C. Next, in step 212, a phenotypic vector is constructed for each organism in the population under study. The elements in the phenotypic vectors are the measured cellular constituent levels for the respective organisms arranged in the order specified by the cellular constituent clustering results of step 210. For illustration, suppose there are ten cellular constituents, (1, 2, 3, 4, 5, 6, 7, 8, 9, and 10), where constituents 8-10 fall into group A, constituents 4-7 fall into group B, and constituents 1-3 fall into group C. In this instance, a phenotypic vector $V_M$ for an organism M in the population could have the form:

$$V_M = \{8, 9, 10, 4, 5, 6, 7, 1, 2, 3\}$$

where each respective cellular constituent in the vector is represented by the level of the cellular constituent in the organism represented by the vector. Each vector $V_M$ is clustered based on these levels. Consider the hypothetical vectors for four such organisms, where cellular constituent levels are merely represented as "+" for high level and "−" for low level:

$$V_1 = \{+, -, +, +, +, -, -, -, -, -\}$$

$$V_2 = \{-, -, -, -, -, +, +, +, +, +\}$$

$$V_3 = \{+, +, +, +, +, -, -, -, -, -\}$$

$$V_4 = \{-, -, -, -, -, +, +, +, -, +\}$$

Clustering $V_1$ through $V_4$ will result in two groups (I and II):

$$V_1 = \{+, -, +, +, +, -, -, -, -, -\}$$

$$V_3 = \{+, +, +, +, +, -, -, -, -, -\} \quad \text{Group I}$$

$$V_2 = \{-, -, -, -, -, +, +, +, +, +\}$$

$$V_4 = \{-, -, -, -, -, +, +, +, -, +\} \quad \text{Group II}$$

It is apparent that each organism in group I has a similar cellular constituent expression (or level) pattern. Further, this similar pattern distinguishes group I from group II. Likewise, each organism in group II has a similar cellular constituent (or level) pattern and this pattern distinguishes group II from group I. In this example, the ordered set of cellular constituents from step 210 serves as a classifier that reclassifies the organisms into subtypes. This form of clustering is illustrated in Example 5.8.2 in conjunction with FIG. 9.

In some embodiments the clustering of step 210 is not performed and only phenotypic vectors are clustered in order to identify such phenotypic clusters. However, it will be appreciated from the example above that the identification of cellular constituents that can discriminate the phenotypic clusters will be more easily identifiable in cases where the clustering of step 210 is performed because the clustering of step 210 will tend to group discriminating cellular constituents within each phenotypic vector.

It is noted that each of the subtypes (subgroups) obtained in this step are not obtained using classical phenotypic observations. Rather, each of the subtypes are identified using an ordered set of cellular constituents levels that discriminate between phenotypically distinguishable groups. As such, each of the subtypes identified in step 212 may well represent distinct biochemical forms of the trait under study. For example, in the case where perturbations are applied in the preceding steps, each of the subtypes identified in this step could represent a different biochemical response associated with the trait.

In step 212, the cellular constituents that can discriminate between the newly identified subgroups (subtypes) are determined. For example, consider the example above in which the following clusters were obtained:

$$V_1 = \{+, -, +, +, +, -, -, -, -, -\}$$

$$V_3 = \{+, +, +, +, +, -, -, -, -, -\} \quad \text{Group I}$$

$$V_2 = \{-, -, -, -, -, +, +, +, +, +\}$$

$$V_4 = \{-, -, -, -, -, +, +, +, -, +\} \quad \text{Group II}$$

where the order of the elements in each vector is $$V_M = \{8, 9, 10, 4, 5, 6, 7, 1, 2, 3\}$$

It can be seen that cellular constituents 8, 10, 4, 5, 6, 7, 1, and 3 discriminate between groups I and II whereas cellular constituents 9 and 2 do not discriminate. For example, cellular constituent 9 has the values (−/+) in group I and (−/−) in group II and cellular constituent 2 has the values (−/−) in group I and (+/−) in group II.

The set of cellular constituents that discriminate between subtypes (subgroups) identified in step 212 serve as a classifier for the population under study. This classifier is capable of differentiating the general population into subtypes. While select organisms (e.g., phenotypically extreme organisms) were used in previous steps in order to identify and order the discriminating set of cellular constituents (the classifier), the cellular constituents identified in step 212 are capable of classifying all the organisms in the general population into subgroups.

Steps 214 and 216.

The cellular constituents identified in step 212 represent the surrogate markers for the one or more primary targets acting in the primary tissue of interest. If the target genes that affect the complex trait are already known (214—Yes), then the process ends and the set of cellular constituents identified in step 212 can be used to monitor activity of the primary target in the primary tissue of interest (216). If the one or more target genes in the primary tissue are not known a priori (214—No), then additional processing steps can be performed to either identify (i) a locus (e.g., QTL, haplotype, or allele) in the genome of the species under study that is associated with the trait or (ii) the gene that is genetically linked to such a locus.

In some embodiments, the identification of the one or more target genes in the primary tissue is not known but there is no immediate need to identify such target genes. In such instances, process control can stop and the set of cellular constituents from step 212 can be used as a surrogate marker for the target gene or genes in the primary tissue even though the identity of the target gene or genes in the primary tissue remains unknown. This feature of the invention has significant application because it provides a way to monitor for absence or presence of a phenotypic feature, such as the absence or presence of a disease, using cellular constituent abundance values from readily accessible tissues. This is particularly advantageous in a variety of situations. For example, it is advantageous in situations where (i) the identity of the primary tissue is not known, (ii) the identity of the primary tissue is known but the identities of the cellular constituents that drive the phenotypic feature under study (e.g., complex disease) are not known, (iii) the identity of the primary tissue is known and the identities of the cellular constituents that drive the phenotypic feature under study are known but it is not easy or is impossible to measure cellular constituent abundance levels in the primary tissue. For example, in some instances the primary tissue could be bone, heart, or brain. Such tissues and organs represent relatively difficult tissues from which to obtain a biopsy in order to conduct microarray based cellular constituent profiling. Thus, in each of these instances, the method defined by steps 202 through 216 represent a highly advantageous and novel method. Cellular constituent abundance values from tissues that are relatively easy to biopsy or otherwise obtain are measured (step 202). From this data, the population is classified into subgroups and cellular constituents are identified that can discriminate the subgroups (step 208). The population is clustered based on similarity in expression of the genes identified in step 208 (step 212) and cellular constituents that can discriminate these final clusters serve as the surrogate markers (step 216). These surrogate markers have application in diagnostic detection of a disease, drug therapy discovery, as well as disease prognosis.

Step 218.

In step 218, each cellular constituent 48 in the set of cellular constituents identified in step 212 is used in a quantitative genetic analysis. Each quantitative genetic analysis is performed using the levels of a given cellular constituent 48 (e.g., activity, transcriptional state, translational state, etc.) in the secondary tissue of organisms 46. In preferred embodiments, a separate genetic analysis is performed using pairs of the subgroups identified in step 212. For example, consider the case in which three subgroups (A, B, and C) are identified in step 212 where group A is associated with lean animals and groups B and C are associated with obese animals. In this example, it would be desirable to carry out genetic analysis on the combination of groups A and B (i.e., the cellular constituents from groups A and B) and then again on groups B and C (i.e., the cellular constituents from groups B and C). The exact way in which the identified subgroups will be used in the quantitative genetic analysis will be context dependent. However, generally speaking, genetic analysis requires variation in the group being tested in order to get meaningful results. In one embodiment, each quantitative genetic analysis is performed by genetic analysis module 80 (FIG. 1).

To perform the quantitative genetic studies, marker genotype data 78 (including a high density genetic marker map and allele data for each of the organisms 46 under study) and possibly pedigree data 74 is used. Together, marker genotype data 78 and pedigree data 74 (FIG. 1) provide the actual alleles for each genetic marker typed in each organism 46 under study, in addition to the relationships between these organisms 46. The extent of the relationships between the organisms 46 under study documented in the pedigree data can be as simple as an $F_2$ population or as complicated as extended human family pedigrees. Exemplary sources of pedigree data 74 are described in Section 5.16, below. In some embodiments of the present invention, pedigree data 74 is optional (e.g., when an association analysis is performed).

Marker genotype data 78 at regular intervals across the genome under study or in gene regions of interest is used to monitor segregation or detect associations in a population of organisms 46. Marker genotype data 78 comprise those markers that will be used in the population under study to assess genotypes. In one embodiment, marker genotype data 78 comprises the names of the markers, the type of markers (e.g., SNP, microsatellite, etc.), as well as the physical and genetic locations of the markers in the genomic sequence. Exemplary types of markers include, but are not limited to, restriction fragment length polymorphisms "RFLPs", random amplified polymorphic DNA "RAPDs", amplified fragment length polymorphisms "AFLPs", simple sequence repeats "SSRs", single nucleotide polymorphisms "SNPs", and microsatellites, etc. Further, in some embodiments, marker genotype data 78 comprises the different alleles associated with each marker. For example, a particular microsatellite marker consisting of 'CA' repeats may have represented ten different alleles in the population under study, with each of the ten different alleles in turn consisting of some number of repeats. Representative marker genotype data 78 in accordance with one embodiment of the present invention is found in Section 5.2, below. In one embodiment of the present invention, the genetic markers used comprise single nucleotide polymorphisms (SNPs), microsatellite markers, restriction fragment length polymorphisms, short tandem repeats, DNA methylation markers, and/or sequence length polymorphisms.

In one embodiment, each quantitative genetic analysis performed in step 218 is a whole-genome study. In such studies, loci at locations throughout the genome of the species under study are tested for genetic linkage and/or genetic association to the cellular constituent 48 under consideration. In such embodiments, each step or location along the length of the chromosome can be at regularly defined intervals or somewhat regularly defined intervals. In some embodiments, these regularly defined intervals are defined in Morgans or, more typically, centiMorgans (cM). A Morgan is a unit that expresses the genetic distance between markers on a chromosome. A Morgan is defined as the distance on a chromosome in which one recombinational event is expected to occur per gamete per generation. In some embodiments, each regularly defined interval is less than 100 cM. In other embodiments, each regularly defined interval is less than 10 cM, less than 5 cM, or less than 2.5 cM. In some embodiments, the loci that are tested are not at regularly defined intervals. Rather, any loci for which allelic or haplotypic information is available is tested for genetic linkage and/or association to the perturbation (e.g., complex trait).

Figure 3A:
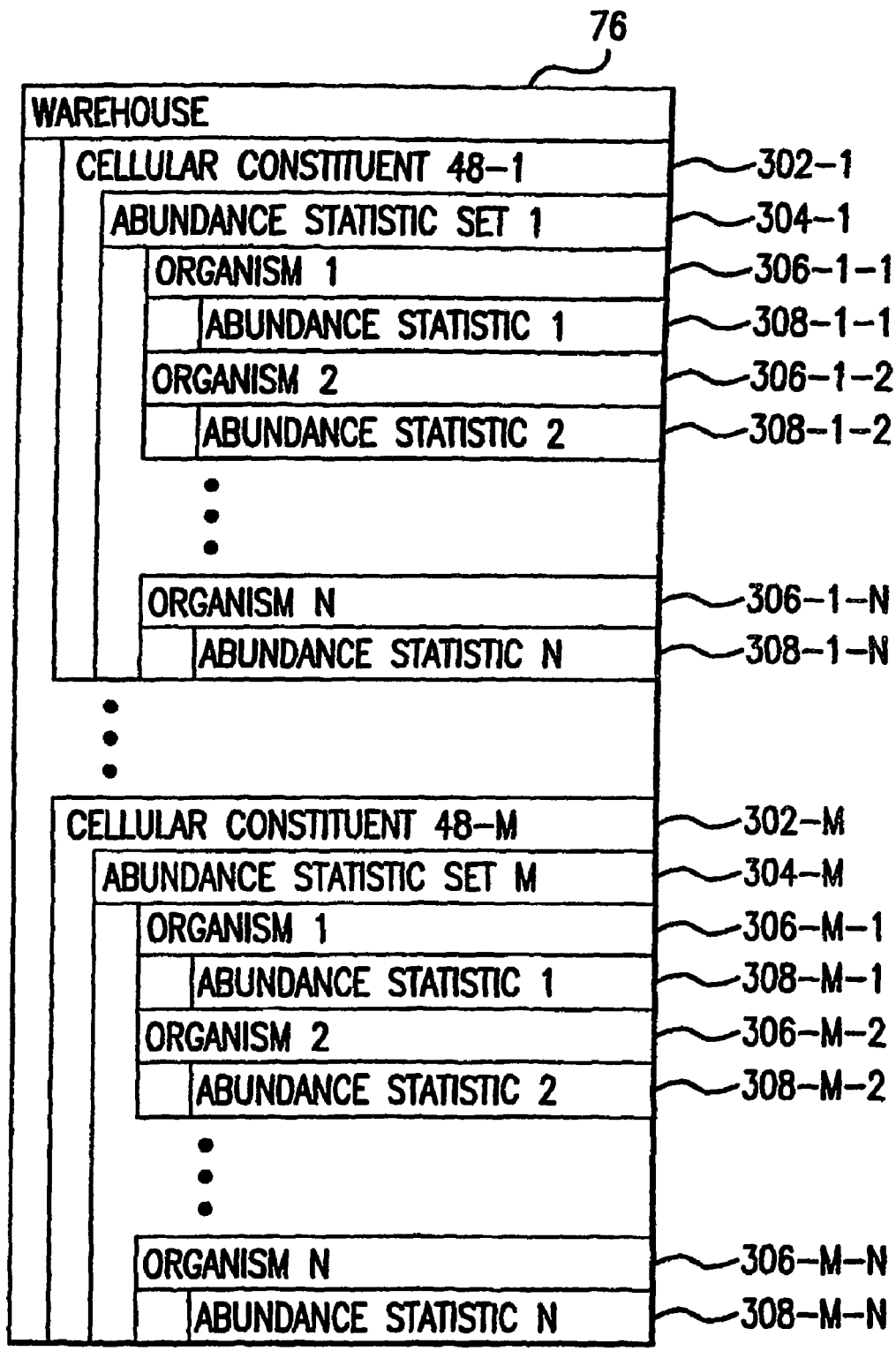
FIG. 3A illustrates an expression/genotype warehouse in accordance with one embodiment of the present invention.

In each quantitative genetic analysis, data corresponding to the level (e.g., activity, transcriptional state, translational state, etc.) of the cellular constituent in the secondary tissue of a plurality of organisms 46 under study is used as the quantitative trait. More specifically, for any given cellular constituent 48, the quantitative trait used in the QTL analysis is an abundance statistic set, such as set 304 (FIG. 3A). Abundance statistic set 304 comprises the corresponding abundance statistic 308 for the cellular constituent 302 (48; FIG. 1) from a subgroup of organisms 306 (46; FIG. 1) identified in step 212.

The nature of the underlying data for abundance statistic 308 will depend upon the nature of the corresponding cellular constituent 48. In some instances, the cellular constituent 48 is a gene and each abundance statistic 308 is a transcriptional state. In some instances, the cellular constituent 48 is a protein and each abundance statistic 308 is a translational state or a protein activity level. Other examples of cellular constituent types and cellular constituent levels have been provided above.

Figure 3B:
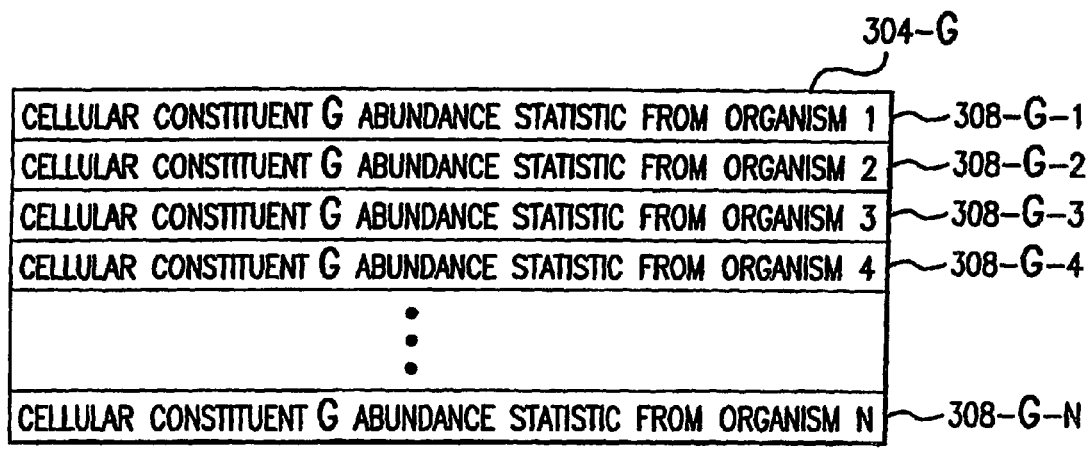
FIG. 3B illustrates a gene expression statistic found in an expression/genotype warehouse in accordance with one embodiment of the present invention.

FIG. 3B illustrates an exemplary abundance statistic set 304 in accordance with one embodiment of the present invention. Exemplary abundance statistic set 304 includes the abundance statistic 308 (e.g., activity, translational state, transcriptional state) of a cellular constituent G from each organism 46 in a subtype (subgroup) identified in step 212.

For example, consider the case where there are ten organisms in a subgroup identified in step 212, and each of the ten organisms expresses a gene. In this case, abundance statistic set 304 includes ten entries, each entry corresponding to a different one of the ten organisms in the plurality of organisms. Further, each entry 308 represents the transcriptional state of the gene (or some aspect related to abundance or level) in the organism represented by the entry. So, entry "1" (308-G-1) corresponds to the transcriptional state of the gene in organism 1, entry "2" (308-G-2) corresponds to the transcriptional state of the gene in organism 2, and so forth.

In one embodiment of the present invention, each quantitative genetic analysis (FIG. 2A, step 218) comprises: (i) testing for genetic linkage and/or association between a loci (e.g., an allele at the loci) in the genome of the species under study and the quantitative trait (e.g., abundance values for a particular cellular constituent in each organism in a plurality of organisms) used in the quantitative genetic analysis, (ii) advancing the position in the genome to another loci in the genome, and (iii) repeating steps (i) and (ii) until all or a portion of the entire genome has been tested. In typical embodiments, the quantitative trait is an abundance statistic set 304, such as the set illustrated in FIG. 3B.

In some embodiments, testing for genetic linkage and/or association between a given position in the genome and the abundance statistic set 304 comprises correlating differences in the abundance levels (e.g., transcriptional state, translational state, activity, phosphorylation state, etc.) found in the abundance level statistic 304 with differences in the genotype (e.g. difference in alleles or haplotypes) at the given loci using a single marker test. Examples of single marker tests include, but are not limited to, t-tests, analysis of variance, or simple linear regression statistics. See, e.g., *Statistical Methods*, Snedecor and Cochran, 1985, Iowa State University Press, Ames, Iowa. However, there are many other methods for testing for linkage and/or association between abundance statistic set 304 and a given position in the genome. In particular, if abundance statistic set 304 is treated as the phenotype (in this case, a quantitative phenotype), then methods such as those disclosed in Doerge, 2002, Mapping and analysis of quantitative trait loci in experimental populations, *Nature Reviews: Genetics* 3:43-62, can be used. Concerning steps (i) through (iii) above, if the genetic length of the genome is N cM and each loci tested is on average 1 cM away from the closets loci tested in another instance of step (i), then N different tests for linkage and/or association are performed. In some embodiments, genetic linkage and/or association is tested at each position in which appropriate genotypic information is available to perform the analysis.

In some embodiments, the genetic data produced from each respective quantitative genetic analysis comprises a logarithmic of the odds score (lod) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to the quantitative trait corresponding to a given gene. Lod scores are further defined in Section 5.4, below. Generally, a lod score of three or more suggests that two loci are genetically linked, a lod score of four or more is strong evidence that two loci are genetically linked, and a lod score of five or more is very strong evidence that two loci are genetically linked. However, the significance of any given lod score actually varies from species to species depending on the model used.

The generation of lod scores requires pedigree data. Accordingly, in embodiments in which a lod score is generated, processing step 218 is a linkage analysis, as described in Section 5.13, below. In some embodiments, the genetic data produced from each respective quantitative genetic test is a p-value, a $\chi^2$ value or some other statistical measure.

In situations where pedigree data 74 is not available, marker genotype data 78 from each of the organisms 46 (FIG. 1) can be used to make a genetic marker map that, in turn, can be compared to each quantitative trait (expression statistic set 304) using association analysis, as described in Section 5.14, below, in order to identify loci that include alleles that associate with expression statistic 304. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected samples compared with control samples. Statistical tests such as a chi-square test are used to determine whether there are differences in allele or genotype distributions. In one example, the affected population are those organisms that have been exposed to a perturbation (e.g., exposed to a drug) versus those organisms that have not been exposed to a perturbation.

Figure 4:
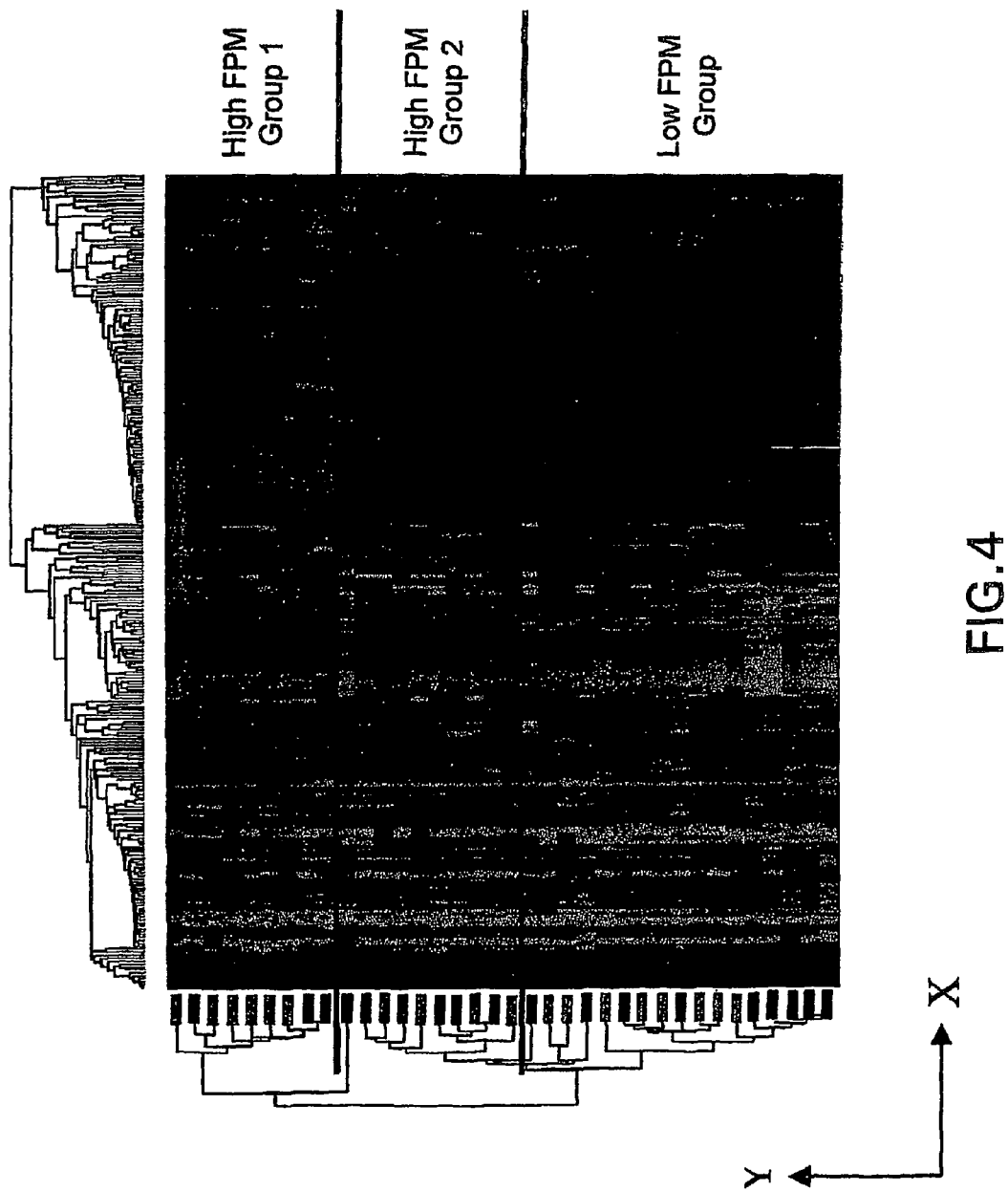
FIG. 4 is a depiction of a two-dimensional cluster of the most differentially expressed set of genes in mice comprising the upper and lower $25^{th}$ percentiles of the subcutaneous fat pad mass (FPM) trait in a segregating population, in accordance with one embodiment of the present invention.

The goal of step 218 is to identify regions of the genome (e.g., QTL, in the case of linkage analysis) that associate with many of the cellular constituents identified in step 212. FIGS. 4 and 5 illustrate this process. For FIG. 4, the upper and lower $25^{th}$ percentiles of a segregating $F_2$ population of mice with respect to fat pad mass were examined. The $F_2$ intercross was constructed from C57BL/6J and DBA/2J strains of mice. Details on this cross are found in Section 5.17, below. FIG. 4 depicts a two-dimensional cluster of the most differentially expressed set of genes in mice comprising the upper and lower $25^{th}$ percentiles of the subcutaneous fat pad mass (FPM) trait in the segregating $F_2$ population. In FIG. 4, the x-axis represents the 280 genes in mice that are most differentially expressed in extreme subpopulations of the mouse population and the y-axis represents the mouse population itself. Thus, the 280 genes depicted in FIG. 4 are associated with the trait obesity.

Each of the 280 genes depicted in FIG. 4 was subjected to quantitative genetic analysis in accordance with the methods described for step 218 of FIG. 2A. From this analysis, it was seen that 55% of the 280 genes link to only five regions in the mouse genome (FIG. 5). In addition, a position on chromosome 2 (FIG. 5; 502) is a hot spot. As used herein, a QTL hot spot "hot spot" is a location in the genome where many more genes link than would be expected by chance. For example, in one embodiment, a hot spot is any 4 cM in which more than one percent of the total number of eQTL identified genome wide colocalize. FIG. 5 plots the percentage of expression QTL (eQTL) at two different lod scores thresholds (3.0 and 4.3) across 920 evenly-spaced bins, each 2 cM wide, covering the mouse genome. The number of eQTL in each bin was divided by the total number of eQTL plotted. eQTL hot spots are apparent on chromosomes 2, 6, 7, 10, 11 and 17. Taking into account the eQTL distribution for all the genes considered in the cross, each of the hot-spot regions are very significantly enriched for eQTL for the genes in the FPM set. The highly non-uniform nature of this eQTL distribution over the chromosomes is not likely to have happened by chance. In fact, with 460 4 cM windows over the 19 autosomal chromosomes, the probability that greater than one percent of the eQTL would localize to one such window is less than $1.2 \times 10^{-16}$. At a lod score of 4.3, over eighty percent of the genes have only a single eQTL, with only ten percent of the genes having more than two detected eQTL. The view at a lower lod score threshold (3.0) represents a slightly more complex picture, given the appearance of many more genes under the control of multiple loci, with greater than 40% of the genes having more than one eQTL and close to four percent of the genes having more than 3 detected eQTL. The hotspots apparent on chromosomes 2, 6, 7, 10, 11, and 17 can be considered the key drivers underlying FPM expression patterns.

Step 222.

Step 218 is used to identify hot spots in the chromosome that are genetically linked to cellular constituents that discriminate the trait under study. For any locus (hot spot) identified in step 218, steps 222 through 236 are directed to identifying the genes underlying the locus.

In step 222, those genes that physically reside in the vicinity of a locus (hot spot) are identified. Identifying those genes that physically reside in the vicinity of the locus can be done using annotation data (e.g., the map of the human genome in the case where the organism 46 is human). For example, in the case where the species under study is mouse, genes can be reliably mapped to a unique autosomal chromosome location using the Celera Mouse Genome database. A hot spot identified in step 218 and a gene are considered coincident when the physical location of the gene maps to within a given threshold distance of a hot spot. In various embodiments, this distance is less than less than 25 cM, less than 20 cM, less than 15 cM, less than 10 cM, less than 5 cM, less than 1 cM, less than 50,000 bases, less than 25,000 bases, less than 10,000 bases or less than 1000 bases.

Step 224.

In step 224, levels of a gene identified in step 222 in a plurality of organisms of the species is used as a quantitative trait in quantitative genetic analysis (e.g., linkage analysis or association analysis). In some embodiments of step 224, the quantitative trait for the gene that is used in the quantitative genetic analysis is an abundance statistic set, such as set 304 (FIG. 3A). Abundance statistic set 304 comprises the corresponding abundance statistic 308 for the genes from organisms 306 (FIG. 46) in the population under study that fall into a subtype identified in step 212. In such embodiments, the transcriptional state of the gene, the translational state of the gene product, the activity of the gene product, or some other measure of the gene can be used as the quantitative phenotype in the genetic analysis.

In some embodiments, genotype data from each of the organisms 46 (FIG. 1) for each marker in genetic marker map 70 is compared to the quantitative trait using population-based or family-based association analysis, as described in Section 5.14, below, in order to identify alleles and/or haplotypes in the genome of the species under study that associate with the quantitative trait (e.g., abundance statistic 304). In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected organisms as compared to control organisms. Statistical tests such as a chi-square test are used to determine whether there are differences in allele or haplotype distributions. Thus, in some embodiments of step 224, members of an affected population and an unaffected population are haplotyped. Then, association analysis is used to determine whether any of the haplotypes strongly associate with an affected or unaffected population.

Step 226.

In step 224 a gene is tested by genetic analysis using expression values (or other forms of measurements) as a quantitative trait. This analysis produces eQTL at specific positions in the genome of the organism under study. In step 226, a determination is made as to whether the gene tested in step 224 is under the control of a cis-acting eQTL that has significant interaction with the hot spot. In practice, the requirement for a cis-acting eQTL removes from consideration all genes except those genes that have a eQTL that co-localizes with the hot spot. Further, the requirement for cis-acting eQTL limits the study to those genes whose physical location colocalizes with the eQTL generated from their expression values. In various embodiments, an eQTL is coincident with the physical location of the gene if the center of the eQTL and the center of the gene are within 10 cM of each other, within 5 cM of each other, within 3 cM of each other, or within 1 cM of each other.

The requirement that there be significant interaction between the cis-acting eQTL and the hot spot is used to add another layer of confidence to the selection of genes using the methods disclosed in FIG. 2B. According to the hypothesis of one embodiment of the present invention, if the eQTL and hot spot are controlled by the same locus, not only will they be colocalized, but they will be correlated in the genetic sense. In other words, the variation of the gene expression and variation in the genotype in the vicinity of the hot spot will be correlated. Genetic interaction between an eQTL and a loci can be tested using techniques that simultaneously analyze multiple QTLs. Such techniques include marker-difference regression (also known as marker regression or joint mapping). See, for example, Kearsey and Hyne, 1994, Theor. Appl. Genet. 89, p. 698; Wu and Li, 1994, Theor. Appl. Genet. 89, p. 535. Such techniques further include interval mapping with marker cofactors. See, for example, Jansen, 1992, Theor. Appl. Genet. 85, p. 252; Jansen, 1993, Genetics 135, p. 205; Zeng, 1993, Proc. Natl. Acad. Sci. USA 90, p. 10972; Zeng, 1994, Genetics 136; p. 1457; Stam, 1991, Proceedings of the Eight Meeting of the Eucarpia Section Biometrics on Plant Breeding, Brno, Czechoslovakia, pp. 24-32; Jansen, 1995, Theor. Appl. Genet. 91, p. 33; van Ooijen, 1994, in van Ooijen and Jansen (eds.), Biometrics in plant breeding: applications of molecular markers, pp. 205-212, CPRO-DLO, Netherlands; and Utz and Melchinger, 1994, in van Ooijen and Jansen (eds.), Biometrics in plant breeding: applications of molecular markers, pp. 195-204, CPRO-DLO, Netherlands. Such techniques further include multiple-trait extensions to composite interval mapping given by Jiang and Zeng.

If the gene does link to a hot spot (226—Yes), then the gene is a possible primary target of the trait under study (232). Even in the case where the gene tested in step 224 does not link to a hot spot (226—No), it is possible that the gene can be associated with or linked to the perturbation (e.g., complex trait) of step 202. To make such a determination, step 228 is performed.

Step 228.

Step 228 is performed in order to determine whether a gene is associated or linked with the trait under study. Typically, step 228 is performed in instances where the gene failed to link to or associate with a hot spot in step 226. However, in some embodiments, step 228 is performed instead of step 226. And, in some embodiments, step 228 is used to validate a gene that does link to or associate with a hot spot. In step 228, a determination is made as to whether any genetic markers within the gene could lead to a functional change that can explain the hot spot in which the gene resides. Such genetic markers can be, for example, SNPs, RFLPs, methylation, or any of a number of different types of markers. If these markers indicate that some alleles code for a functionally altered protein (228—Yes), the gene is not discarded (step 232). If the gene does not link to the hot spot that it resides in (226—No) and does not include markers that indicate functional alteration of the corresponding gene product in some alleles (228—No), then the gene is removed from consideration (step 230).

Step 234.

A determination is made as to whether all genes identified in step 222 have been tested. If not (234—No), process control returns to step 224 where the expression data of another gene identified in step 222 is used in quantitative genetic analysis. If so (234—Yes), control passes to step 236.

Step 236.

The method disclosed in FIG. 2B potentially identifies several genes that could be the primary target of the perturbation optionally applied in step 202. Furthermore, the method disclosed in FIG. 2B potentially identifies one or more genes that affect the trait under study. Step 236 encompasses a wide variety of methods that are used to determine which genes are most likely the primary target of the perturbation optionally applied in step 202 or most likely affect the trait under study. That is, step 236 ranks the genes identified by the method. Factors that affect gene candidacy (gene rank) in step 236 can be selected from the group consisting of (i) how closely a hot spot and the gene overlap (step 226), (ii) the strength of the genetic linkage or association between a gene and the hot spot the gene resides in (e.g., the lod score of the eQTL that overlaps the hot spot, the p-value for the allele that overlaps the hot spot), (iii) the extent and nature of any genetic polymorphisms (e.g., SNPs) within the gene, and (iv) association of alternative splicing events in the gene with the trait under study. Any combination of these factors can be used to rank genes that were not removed from consideration at prior steps of the method.

In some embodiments, the genes that could affect the trait (232) are subjected to multivariate analysis. Multivariate statistical models have the capability of simultaneously considering multiple quantitative traits, modeling epistatic interactions between the genes and testing other interesting variations that determine whether genes in a candidate pathway group belong to the same or related biological pathway. Specific tests can be done to determine if the traits under consideration are actually controlled by the same QTL (pleiotropic effects) or if they are independent. Exemplary multivariate statistical models that can be used in accordance with the present invention are found in Section 5.6, below.

In some embodiments, highly ranked gene targets are further validated by techniques such as gene knock-out/knock-in mice, transgenic mice, or small interfering RNA (siRNA) methods. Various siRNA knock-out techniques (also referred to as RNA interference or post-transcriptional gene silencing) are disclosed, for example, in Xia, et al., 2002, Nature Biotechnology 20, p. 1006; Hannon, 2002, Nature 418, p. 244; Carthew, 2001, Current Opinion in Cell Biology 13, p. 244; Paddison, 2002, Genes & Development 16, p. 948; Paddison & Hannon, 2002, Cancer Cell 2, p. 17; Jang et al., 2002, Proceedings National Academy of Science 99, p. 1984; Martinez et al., 2002, Proceedings National Academy of Science 99, p. 14849.

Alternative to Steps 222 Through 230.

In some embodiments, the hot spots identified in step 218 are used to identify candidate primary target genes using an alternative approach that is described, in part, in U.S. Provisional patent application 60/400,522, filed Aug. 2, 2002, U.S. Provisional patent application 60/460,303, PCT publication number WO 2004/013727, each of which is hereby incorporated by reference in its entirety.

Reference is made to FIG. 13 to illustrate how this alternative approach is accomplished.

Step 1302.

Referring to FIG. 13, starting data is assembled in step 1302. The starting data includes the cellular constituent expression data 44 and marker data 1380. The cellular constituent expression data 44 is preferably from the primary tissue where it is believed gene expression drives the trait under study. In one embodiment, marker data 1382 comprises the names of the markers, the type of markers the physical and genetic location of the markers in the genomic sequence. Exemplary types of markers include, but are not limited to, restriction fragment length polymorphisms "RFLPs", random amplified polymorphic DNA "RAPDs", amplified fragment length polymorphisms "AFLPs", simple sequence repeats "SSRs", single nucleotide polymorphisms "SNPs", microsatellites, etc.). Further, marker data 1382 comprises the different alleles associated with each marker. For example, a particular microsatellite marker consisting of 'CA' repeats may have represented ten different alleles in the population under study, with each of the ten different alleles in turn consisting of some number of repeats. In one embodiment of the present invention, the genetic markers used comprise single nucleotide polymorphisms (SNPs), microsatellite markers, restriction fragment length polymorphisms, short tandem repeats, DNA methylation markers, and/or sequence length polymorphisms. More information on suitable markers is disclosed in Section 5.2.

Step 1304.

Once starting data are assembled, cellular constituent abundance data 44 is transformed into a plurality of expression statistics for gene G. Exemplary expression statistics include, but are not limited to, the mean log ratio, log intensity, or background-corrected intensity for gene G. Each expression statistic represents an expression value for a gene G. In one embodiment, each expression value is a normalized expression level measurement for gene G in an organism in a plurality of organisms under study. In one embodiment, a normalization routine is used to normalize the expression level measurement for gene G. In some embodiments, each expression level measurement is determined by measuring an amount of a cellular constituent encoded by the gene G in one or more cells from an organism in the plurality of organisms. In one embodiment, the amount of the cellular constituent comprises an abundance of an RNA present in one or more cells of the organism. In one embodiment, the abundance of RNA is measured by a method comprising contacting a gene transcript array with the RNA from one or more cells of the organism, or with a nucleic acid derived from the RNA. The gene transcript array comprises a positionally addressable surface with attached nucleic acids or nucleic acid mimics. The nucleic acid mimics are capable of hybridizing with the RNA species or with nucleic acid derived from the RNA species.

In embodiments where the expression level measurement is normalized, any normalization routine may be used. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines may be run. More information on such normalization techniques is found in Section 5.3.

Step 1306.

In addition to the generation of expression statistics from cellular constituent abundance data 44, a genetic map 1382 is generated from marker data 1380 (FIG. 13, step 1306). Typically, genetic map 1382 is built from the marker data using genotype probability distributions for the organisms under study. Genotype probability distributions take into account information such as marker information of parents, known genetic distances between markers, and estimated genetic distances between the markers. Marker data 1380 can comprise single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, simple sequence repeats, or any combination thereof. Genotype data comprises knowledge of which alleles, for each marker considered in marker data 1380, is present in each organism in the plurality of organisms under study. Pedigree data shows one or more relationships between organisms in the plurality of organisms under study.

Step 1308.

Once the expression data has been transformed into corresponding expression statistics and genetic map 1382 has been constructed, the data is transformed into a structure that associates all marker, genotype and expression data for input into QTL analysis software.

Step 1310.

A quantitative trait locus (QTL) analysis is performed using data corresponding to a gene G as a quantitative trait (FIG. 13, step 1310). In one example, the QTL analysis steps through a genetic map 1382 that represents the genome of the species under study. Linkages to gene G are tested at each step or location along the genetic map. In such embodiments, each step or location along the length of the genetic map can be at regularly defined intervals. In some embodiments, these regularly defined intervals are defined in Morgans or, more typically, centiMorgans (cM). In some embodiments, each regularly defined interval is less than 100 cM. In other embodiments, each regularly defined interval is less than 10 cM, less than 5 cM, or less than 2.5 cM.

In the QTL analysis of step 1310, data corresponding to gene G is used as a quantitative trait. More specifically, the quantitative trait used in the QTL analysis is an expression statistic set that corresponds to gene G. That is, the expression statistic set comprises the expression statistic for gene G from each organism 46 in the population under study. An expression statistic set can include the expression level of gene G from a specific tissue in each organism in a plurality of organisms. For example, consider the case where there are ten organisms in the plurality of organisms, and each of the ten organisms expresses gene G in a specific tissue (e.g., secondary tissue). In this case, the expression statistic set includes ten entries, each entry corresponding to a different one of the ten organisms in the plurality of organisms.

In one embodiment of the present invention, the QTL analysis (FIG. 13, step 1310) comprises: (i) testing for linkage between (a) the genotype of the plurality of organisms at a position in the genome of the single species and (b) the plurality of expression statistics for gene G, (ii) advancing the position in the genome by an amount, and (iii) repeating steps (i) and (ii) until all or a portion of the genome has been tested. In some embodiments, the amount advanced in each instance of (ii) is less than 100 centiMorgans, less than 10 centiMorgans, less than 5 centiMorgans, or less than 2.5 centiMorgans. In some embodiments, the testing comprises performing linkage analysis (Section 5.13) or association analysis (Section 5.14) that generates a statistical score for the position in the genome of the single species. As detailed below, in some embodiments, the testing is linkage analysis and the statistical score is a logarithm of the odds (lod) score. Thus, in some embodiments, an eQTL identified in processing step 1310 is represented by a lod score that is greater than 2.0, greater than 3.0, greater than 4.0, or greater than 5.0.

In situations where pedigree data is not available, genotype data from each of the organisms 46 (FIG. 1) for each marker in marker data 1380 can be compared to each quantitative trait using allelic association analysis, as described in Section 5.14, supra, in order to identify QTL that are linked to each expression statistic set. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected compared with control samples.

Statistical tests such as a chi-square test can be used to determine whether there are differences in allele or genotype distributions.

In some embodiments, testing for linkage between a given position in the chromosome and the expression statistic set comprises correlating differences in the expression levels found in the expression level statistic with differences in the genotype at the given position using single marker tests (for example using t-tests, analysis of variance, or simple linear regression statistics). See, e.g., *Statistical Methods*, Snedecor and Cochran, Iowa State University Press, Ames, Iowa (1985). However, there are many other methods for testing for linkage between expression statistic set and a given position in the chromosome. In particular, if expression statistic set is treated as the phenotype (in this case, a quantitative phenotype), then methods such as those disclosed in Doerge, 2002, Nature Reviews Genetics 3, 43-62, may be used. Concerning steps (i) through (iii) above, if the genetic length of the genome is N cM and 1 cM steps are used, then N different tests for linkage are performed on the given chromosome. Furthermore, multiple QTLs can be considered simultaneously in step 1310. For example, marker-difference regression techniques or composite interval mapping can be used. See, for example, Chapters 15 and 16 of Lynch & Walsh, 1998, *Genetics and Analysis of Quantitative Traits*, Sinauer Associates, Inc., Sunderland, Mass.

In some embodiments, the QTL data produced from QTL analysis 1310 comprises a logarithm of the odds score (lod) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to the quantitative trait corresponding to a given gene. Lod scores are further described in Section 5.4. A lod score of three or more is generally taken to indicate that two loci are genetically linked. The generation of lod scores requires pedigree data. Accordingly, in embodiments in which a lod score is generated, processing step 1310 is essentially a linkage analysis, as described in Section 5.13, with the exception that the quantitative trait under study is derived from data, such as cellular constituent expression statistics, rather than classical phenotypes such as eye color. In situations where pedigree data is not available, genotype data from each of the organisms 46 for each marker in genetic map 1382 can be compared to each quantitative trait using association analysis, as described in Section 5.14, supra, in order to identify eQTL that are linked to the gene under study.

In some embodiments, processing step 1310 yields a data structure that includes all positions in the genome of the organisms 46 that were tested for linkage to the expression statistic set in step 1310. For each position, genotype data for the population provides the genotype at the position for each organism in the plurality of organisms under study. For each such position analyzed by QTL analysis 1310, a statistical measure (e.g., statistical score), such as the maximum lod score between the position and the expression statistic set, is provided by processing step 1310. Thus, processing step 1310 yields all the positions in the genome of the organism of interest that are linked to the expression statistic set tested in step 1310. Such positions are referred to as the eQTL for the linked gene G tested in step 1310.

Step 1312.

In processing step 1312, a hot spot chromosomal location (cQTL) identified in step 218 is selected.

Step 1314.

Processing step 1310 identifies any number of expression quantitative trait loci (eQTL) for a gene G whereas processing step 1312 selects one of the any number of hot spots identified in processing step 218. In processing step 1314, a determination is made as to whether an eQTL from processing step 1310 colocalizes with a cQTL from processing step 218 (do an eQTL and cQTL fall onto the same point in the genome of the species). In some embodiments, an eQTL and a cQTL are deemed to be colocalized if they fall within 50 centiMorgans (cM) of each other within the genome of the species under study. In some embodiments, an eQTL and cQTL are deemed to be colocalized if they fall within 40 cM, 30 cM, 20 cM, 15 cM or 10 cM of each other within the genome of the species under study. In some embodiments, an eQTL and cQTL are deemed to be colocalized if they fall within 8 cM, 6 cM, 4 cM, or 2 cM of each other within the genome of the species under study.

In some embodiments of step 1314, an eQTL/cQTL pair is not considered to be colocalized no matter how close the eQTL and cQTL are unless the QTL (the position of the eQTL/cQTL overlap) is truly common to the clinical and expression trait (pleiotropic effect) rather than simply representing two closely linked QTL (linkage disequilibrium). Thus, in some embodiments of step 1314, in order to achieve the result 1314—Yes, the subject eQTL and cQTL must pass a pleiotropy test described in Section 5.19.

In some embodiments, negative loglikelihoods to the null hypothesis and the alternative hypothesis described in Section 5.19 are minimized with respect to the model parameters ($\mu_i$, $\beta_j$, and $\sigma_k$) using maximum likelihood analysis. The likelihood ratio test statistic can be formed from these likelihoods to assess whether the alternative hypothesis (no pleiotropy) is preferred over the null hypothesis (1314—No). If the null hypothesis is preferred (1314—Yes), then test 1316 is considered.

Steps 1316-1320.

In some embodiments of the present invention, when an eQTL for gene G colocalizes with a cQTL, gene G is considered to be a primary target of the trait under study (step 1320). If this condition is not satisfied (1314—No), then another gene G in the genome of the species under study is selected and process control returns to step 1310 (FIG. 13). In other embodiments, the condition is imposed that the eQTL for gene G colocalizes to the physical location of gene G in the genome (1316—Yes) before gene G is considered to be primary target of the trait under study (step 1320) (the eQTL must be a cis-acting QLT). In other words, the eQTL must correspond to the physical location of gene G in the genome of the single species in order for the gene to be considered a primary target for the trait under study. In some embodiments, an eQTL corresponds to the physical location of gene G if the eQTL and G colocalize within 5 cM, 4 cM, 3 cM, 2 cM, 1 cM, or less in the genome of said single species. In embodiments where condition 1316 is imposed, when the condition is not satisfied (1316—No), another gene G in the genome of the species under study is selected and process control returns to step 1310. These steps are repeated for each of the hot spots identified in step 218. Alternatively, these steps are performed by considering each of the hot spots simultaneously.

5.1.3 Generalized Approach

This section describes a more generalized approach to identifying cellular constituents that serve as surrogate markers in a secondary tissue to a target gene whose expression is linked to a trait of interest. Further, the generalized approach has additional utility, as will be described in further detail below. The initial steps, steps 202-206, taken in this more generalized approach are the same as those described in Section 5.1.2, above. Namely, a trait is identified, cellular constituent level data is measured in as many different tissues as possible or as feasible, and the cellular constituent level data is transformed into expression statistics.

Step 250.

In step 250 (FIG. 2C), one or more phenotypes are measured for each organism 46 in the population under study. FIG. 11 summarizes the data that is measured as a result of steps 202-206 and 250. For each organism 46 in the population under study there are at least two classes of data collected. The first class of data collected is phenotypic information 1101. Phenotypic information 1101 can be anything related to the trait under study. For example, phenotypic information 1101 can be a binary event, such as whether or not a particular organism exhibits the phenotype (+/−). The phenotypic information can be some quantity, such as the results of an obesity measurement for the respective organism 46. As illustrated in FIG. 11, there can be more than one phenotypic measurement made per organism 46.

The second class of data collected for each organism 46 in the population under study is cellular constituent levels 50 (e.g., amounts, abundances) for a plurality of cellular constituents (steps 204-206, FIG. 2A). Although not illustrated in FIG. 11, there can be several sets of cellular constituent measurements for each organism. Each of these sets could represent cellular constituent measurements measured in the respective organism 46 after the organism has been subjected to a perturbation that affects the trait under study. Representative perturbations include, but are not limited to, exposing the organism 46 to an amount of a compound. Further, each set of cellular constituents for a respective organism 46 could represent measurements taken from a different tissue in the organisms. For example, one set of cellular constituent measurements could be from a blood sample taken from the respective organism while another set of cellular constituent measurements could be from fat tissue from the respective organism.

Step 252.

In step 252 (FIG. 2C), the phenotypic data 1101 (FIG. 11) collected in step 250 is used to divide the population into phenotypic groups 1210 (FIG. 12). The method by which step 252 is accomplished is dependent upon the type of phenotypic data measured in step 250. For example, in the case where the only phenotypic data is whether or not the organism 46 exhibits a particular trait, step 252 is straightforward. Those organisms 46 that exhibit the trait are placed in a first group and those organisms 46 that do not exhibit the trait are placed in a second group. A slightly more complex example is where amounts 1101 represent gradations of a quantified trait exhibited by each organism 46. For example, in the case where the trait is obesity, each amount 1101 can correspond to an obesity index (e.g., body mass index, etc.) for the respective organism 46. In this second example, organisms 46 can be binned into phenotypic groups 1210 as a function of the obesity index.

In yet another example in accordance with the invention, several phenotypic measurements can be collected for a given organism 46. In such embodiments, each phenotypic measurement 1101 for a respective organism 46 can be treated as elements of a phenotypic vector corresponding to the respective organism 46. These phenotypic vectors can then be clustered using, for example, any of the clustering techniques disclosed in Section 5.5 in order to derive phenotypic groups 1210. To illustrate, in one example, the organisms 46 are human and measurements 1101 are derived from a standard 12-lead electrocardiogram graph (ECG). The standard 12-lead ECG is a representation of the heart's electrical activity recorded from electrodes on the body surface. The ECG provides a wealth of phenotypic data including, but not limited to, heart rate, heart rhythm, conduction, wave form description, and ECG interpretation (typically a binary event, e.g., normal, abnormal). Each of these different phenotypes (heart rate, heart rhythm) can be quantified as elements in a phenotypic vector. Further, some elements of the phenotypic vector (e.g., ECG interpretation) can be given more weight during clustering. For instance, the ECG measurements can be augmented by additional phenotypes such as blood cholesterol level, blood triglyceride level, sex, or age in order to derive a phenotypic vector for each respective organism 46. Once suitable phenotypic vectors are constructed, they can be clustered using any of the clustering algorithms in Section 5.5 in order to identify phenotypic groups 1210.

In some embodiments, step 252 is an iterative process in which various phenotypic vectors are constructed and clustered until a form of phenotypic vector that produces clear, distinct groups is identified. Of particular interest are those phenotypic vectors that are capable of producing phenotypic groups 1210 that are uniquely characterized by certain phenotypes (e.g., an abnormal ECG/high cholesterol subgroup, a normal ECG/low cholesterol subgroup).

Using the example presented above, phenotypic vectors that can be iteratively tested include a vector that has ECG data only, one that has blood measurements only, one that is a combination of the ECG data and blood measurements, one that has only select ECG data, one that has weighted ECG data, and so forth. Furthermore, optimal phenotypic vectors can be identified using search techniques such as stochastic search techniques (e.g., simulated annealing, genetic algorithm). See, for example, Duda et al., 2001, *Pattern Recognition*, second edition, John Wiley & Sons, New York.

Step 254.

In step 254, the phenotypic extremes within the population are identified. For example, in one case, the trait of interest is obesity. In such an example, very obese and very skinny organisms 46 can be selected as the phenotypic extremes in this step. In one embodiment of the present invention, a phenotypic extreme is defined as the top or lowest $40^{th}$, $30^{th}$, $20^{th}$, or $10^{th}$ percentile of the population with respect to a given phenotype exhibited by the population.

Step 256.

In step 256, a plurality of cellular constituents (levels 50, FIG. 11) for the species represented by organisms 46 are filtered. Only levels 50 measured for phenotypically extreme organisms 46 selected in step 254 are used in this filtering. To illustrate using FIG. 11, consider the case in which organism 46-1 and organism 46-N represent phenotypic extremes with respect to some phenotype whereas organism 46-2 does not. Then, in this instance, levels 50 measured for organism 46-6 and 46-N will be considered in the filtering whereas levels 50 measured for organism 46-2 will not be considered in the filtering.

In some embodiments, cellular constituent levels 50 (measured in phenotypically extreme organisms) for a given cellular constituent 46 are subjected to a t-test or some other test such as a multivariate test to determine whether the given cellular constituent 46 can discriminate between the phenotypic groups 1210 (FIG. 12) that were identified in step 252, above. A cellular constituent 46 will discriminate between phenotypic groups when the cellular constituent is found at characteristically different levels in each of the phenotypic groups 1210. For example, in the case where there are two phenotypic groups 1210, a cellular constituent will discriminate between the two groups 1210 when levels 50 of the cellular constituent (measured in phenotypically extreme organisms) are found at a first level in the first phenotypic group and are found at a second level in the second phenotypic group, where the first and second level are distinctly different.

In preferred embodiments, each cellular constituent is subjected to a t-test without consideration of the other cellular constituents in the organism. However, in other embodiments, groups of cellular constituents are compared in a multivariate analysis in step 256 in order to identify those cellular constituents that discriminate between phenotypic groups 1210.

Step 258.

Typically, there will be a large number of cellular constituents expressed in phenotypically extreme organisms that appear to differentiate between the phenotypic groups identified in step 252. In some instances, this number of cellular constituents 48 can exceed the number of organisms 46 available for study. For instance, in some embodiments, 25,000 genes or more are considered in previous steps. Thus, there may be hundreds if not thousands of genes that discriminate the phenotypically extreme groups. In some instances, these discriminating cellular constituents are analyzed in subsequent steps with statistical models that involve many statistical parameters that cannot accommodate more cellular constituents than organisms as this leads to an over-determined system. In such instances, it is desirable to reduce the number of cellular constituents using a reducing algorithm. However, in other instances, other forms of statistical analysis are used that do not require reduction in the number of cellular constituents under consideration.

The reducing algorithms that are optionally used in step 258 use the p-value or other form of metric computed for each cellular constituent in step 256 as a basis for reducing the dimensionality of the cellular constituent set identified in step 256. A few exemplary reducing algorithms will be discussed. However, those of skill in the art will appreciate that many reducing algorithms are known in the art and all such algorithms can be used in step 258.

One reducing algorithm is stepwise regression. The basic procedure in stepwise regression involves (1) identifying an initial model (e.g., an initial set of cellular constituents), (2) iteratively "stepping," that is, repeatedly altering the model at the previous step by adding or removing a predictor variable (cellular constituent) in accordance with the "stepping criteria," and (3) terminating the search when stepping is no longer possible given the stepping criteria, or when a specified maximum number of steps has been reached. Forward stepwise regression starts with no model terms (e.g. no cellular constituents). At each step the regression adds the most statistically significant term until there are none left. Backward stepwise regression starts with all the terms in the model and removes the least significant cellular constituents until all the remaining cellular constituents are statistically significant. It is also possible to start with a subset of all the cellular constituents and then add significant cellular constituents or remove insignificant cellular constituents until a desired dimensionality reduction is achieved.

Another reducing algorithm that can be used in step 258 is all-possible-subset regression. In fact, all-possible-subset regression can be used in conjunction with stepwise regression. The stepwise regression search approach presumes there is a single "best" subset of cellular constituents and seeks to identify it. In the all-possible-subset regression approach, the range of subset sizes that could be considered to be useful is made. Only the "best" of all possible subsets within this range of subset sizes are then considered. Several different criteria can be used for ordering subsets in terms of "goodness", such as multiple R-square, adjusted R-square, and Mallow's Cp statistics. When all-possible-subset regression is used in conjunction with stepwise methods, the subset multiple R-square statistic allows direct comparisons of the "best" subsets identified using each approach.

Another approach to reducing higher dimensional space into lower dimensional space in accordance with step 258 (FIG. 2C) of the present invention is the use of linear combinations of cellular constituents. In effect, linear methods project high-dimensional data onto a lower dimensional space. Two approaches for accomplishing this projection include Principal Component Analysis (PCA) and Multiple-Discriminant Analysis (MDA). PCA seeks a projection that best represents the data in a least-squares sense whereas MDA seeks a projection that bests separates the data in a least-squares sense. See, for example, Duda et al., 2001, *Pattern Classification*, John-Wiley, New York, Chapters 3 and 10. See, also, Hasti et al., 2001, *The Elements of Statistical Learning*, Springer, N.Y.

The ultimate goal of step 258 is to identify a classifier derived from the set of cellular constituents identified in step 256 or a subset of the cellular constituents identified in step 256 that satisfactorily classifies organisms 46 into the phenotypic groups 1210 identified in step 252. In some embodiments of the present invention, stochastic search methods such as simulated annealing can be used to identify such a classifier or subset. In the simulated annealing approach, for example, each cellular constituent under consideration can be assigned a weight in a function that assesses the aggregate ability of the set of cellular constituents identified in step 256 to discriminate the organisms 46 into the phenotypic classes identified in step 252. During the simulated annealing algorithm these weights can be adjusted. In fact, some cellular constituents can be assigned a zero weight and, therefore, be effectively eliminated during the anneal thereby effectively reducing the number of cellular constituents used in subsequent steps. Other stochastic methods that can be used in step 258 include, but are not limited to, genetic algorithms. See, for example, the stochastic methods in Chapter 7 of Duda et al, 2001, *Pattern Classification*, second edition, John Wiley & Sons, New York.

Step 260.

In some embodiments, the cellular constituents identified in steps 256 and/or 258 are clustered in order to further identify subgroups within each phenotypic subpopulation. To perform such clustering, an expression vector is created for each cellular constituent under consideration. To create an expression vector for a respective cellular constituent, the levels 1101 measured for the respective cellular constituent in each of the phenotypically extreme organisms is used as an element in the vector. For example, consider the case in which an expression vector for cellular constituent 48-1 is to be constructed from organisms 46-1, 46-2, and 46-3. Levels 50-1-1, 50-2-1, and 50-3-1 would serve as the three elements of the expression vector that represents cellular constituent 48-1. Each of the expression vectors are then clustered using, for example, any of the clustering techniques described in Section 5.5. In one embodiment, k-means clustering (Section 5.5.2) is used. That is, a decision is made before clustering as to how many subgroups should be constructed (e.g., 2). Such a decision can be made by visual inspection of the cellular constituent data prior to clustering.

A benefit of step 260 is that the clustering performed in the step refines the trait under study into groups 1220 (FIG. 12)

that are not distinguishable using gross observable phenotypic data (other than cellular constituent levels) such as amounts 1101 (FIG. 11). As such, optional step 260 provides a way to refine the definition of the clinical trait under study by focusing on those cellular constituents that actually give rise to the clinical trait or well reflect the varied biochemical response to that trait. However, the refinement provided in step 260 can be considered incomplete because it is based on only a select portion of the general population under study, those organisms that represent phenotypic extremes. For this reason, pattern classification techniques are used in subsequent steps of the instant method to build a robust classifier that is capable of classifying the general population into subgroups in a manner that does not rely upon phenotypic levels 1101 (FIG. 11).

Step 264.

In step 264, the set of cellular constituents identified as discriminators between phenotypic extremes identified in previous steps (or principal components derived from such cellular constituents) are used to build a classifier. This set of cellular constituents actually refines the definition of the clinical phenotype under study. A number of pattern classification techniques can be used to accomplish this task, including, but not limited to, Bayesian decision theory, maximum-likelihood estimation, linear discriminant functions, multilayer neural networks, as well as supervised and unsupervised learning.

In one embodiment in accordance with step 264, the set of cellular constituents that discriminate the phenotypically extreme organisms into phenotypic groups is used to train a neural network using, for example, a back-propagation algorithm. In this embodiment, the neural network serves as a classifier. First, the neural network is trained with a probability distribution derived from the set of cellular constituents that discriminate the phenotypically extreme organisms into phenotypic groups. For example, in some embodiments, the probability distribution comprises each cellular constituent t-value or other statistic computed in step 256. Once the neural network has been trained, it is used to classify the general population into phenotypic groups. In some embodiments, the neural network that is trained is a multilayer neural network. In other embodiments, a projection pursuit regression, a generalized additive model, or a multivariate adaptive regression spline is used. See for, example, any of the techniques disclosed in Chapter 6 of Duda et al., 2001, *Pattern Classification*, second edition, John Wiley & Sons, Inc., New York.

In another embodiment in accordance with step 264, Bayesian decision theory can be used to build a classifier. Bayesian decision theory plays a role when there is some a priori information pertaining to the organisms to be classified. Here, a probability distribution derived from the set of cellular constituents that discriminate the phenotypically extreme organisms into phenotypic groups serves as the a priori information. For example, in some embodiments, this probability distribution comprises each cellular constituent t-value or other statistic computed in step 256. For more information on Bayesian decision theory, see for, example, any of the techniques disclosed in Chapters 2 and 3 of Duda et al., 2001, *Pattern Classification*, second edition, John Wiley & Sons, Inc., New York.

In still another embodiment in accordance with step 264, linear discriminate analysis (functions), linear programming algorithms, or support vector machines are used to create a classifier that is capable of classifying the general population of organisms 46 into phenotypic groups 1210. This classification is based on the cellular constituent data 50 for the cellular constituents 48 that refined the definition of the clinical phenotype (i.e. the cellular constituents selected in steps 256, 258, and/or 260). For more information on this class of pattern classification functions, see for, example, any of the techniques disclosed in Chapter 5 of Duda et al, 2001, *Pattern Classification*, second edition, John Wiley & Sons, Inc., New York.

In many embodiments, the classifier constructed in this step does not take the form of a simple subset of cellular constituents identified in steps 256 through 260. Rather, the form of the classifier will depend on the type of pattern recognition technique used in this step. In some embodiments, however, the classifier formed in this step can be a simple subset of cellular constituents in the case where the classification scheme is a simple decision tree (e.g., if level for constituent 5 is greater than 50 than place in phenotypic class B).

Step 266.

In step 266, the classifier derived in step 264 is used to classify all or a substantial portion (e.g., more than 30%, more than 50%, more than 75%) of the population under study. Essentially, the classifier bins the remaining population (the portions of the population that do not include the phenotypic extremes) without taking their phenotype (e.g., phenotype amounts 1101, FIG. 11) into consideration. The process of using the classifier to classify the general population produces phenotypic classifications 1250 (FIG. 12). Phenotypic subgroups 1250 can be considered a refinement of the trait under study and subsequently used in analysis of the underlying biochemical processes that differentiate the trait under study into groups 1250 using the techniques disclosed below.

Step 268.

The steps leading to and including step 260 identify cellular constituents from phenotypically extreme organisms that are differentially expressed. In step 264, this set of cellular constituents is used to construct a classifier. As illustrated in FIG. 12, in step 266, the classifier constructed in step 264 classifies the trait under study into subgroups 1250 without consideration of phenotypic data (e.g., without consideration of levels 1101, FIG. 11). It is expected that subgroups 1250 define subgroups of the trait under study and that each of the subgroups define some form of homogenous biochemical form of the trait under study. The biochemical homogeneity in each group 1250 can be exploited using quantitative genetic methods in order to identify genes and biochemical pathways that affect the trait under study, as detailed below.

In step 268, a determination is made as to whether the gene (or genes) that affect the trait under study are known. If so, (step 268—Yes), step 270 is performed. If not, (step 268—No), step 272 is performed. In some embodiments, both steps 270 and 272 are performed and step 268 is skipped. In some embodiments, as in the case in step 214 of FIG. 2, all remaining steps are skipped and the classifier developed in steps 264 and 266 is used as a surrogate marker for the target in the primary tissue even in those instances where the primary target is not known.

Step 270.

Step 270 is illustrated in FIG. 12. In step 270, the classifier derived in step 264 is used to classify a general population of the organisms under study into specific subgroups 1250. In this way, the classifier allows for the determination of which subgroup 1250 a given organism 46 (FIG. 1) belongs. This form of classification is useful in tracking organisms in response to perturbations, over the lifespan of the organism, or as a certain disease progresses in the organism. Step 270 is highly advantageous because it provides, among other things, a reliable method for diagnosing the condition of an organism with respect to a highly refined definition of the trait under study. This utility can be illustrated by the following example in which the secondary tissue is a blood sample taken from a patient. Cellular constituent measurements are made using the blood sample. In turn, the cellular constituent measurements are used by the preconstructed classifier (step 270) to differentiate the organism into a subgroup 1250. In this example, each subgroup 1250 can represent a stage of a complex disease. Accordingly, the example illustrates a novel technique for diagnosing disease progression.

The classification of a population into subgroups 1250 can also be used to develop a set of surrogate markers. For example, the cellular constituents that can discriminate between groups 1250 can be determined. Then, these cellular constituents can be used as a set of surrogate markers.

Step 272.

Step 272 illustrates another advantageous use for the methods disclosed in this section. The classifier formed in step 264 serves to refine the definition of a trait of interest. Each group 1250 in FIG. 12 defined by the classifier potentially represents a homogenous population with respect to the trait of interest. Accordingly, cellular constituent measurements from organisms in respective groups 1250 can be used as quantitative traits in quantitative genetic studies such as linkage analysis (Section 5.13) or association analysis (5.14). It is expected that linkage analysis and/or association analysis using data from individual groups 1250 rather than the general population will provide improved results, particularly in situations where the trait under study is complex and/or is driven by many different genes. In such instances, the individual groups 1250 could represent a more homogenous population or state. Consequently, the genes that drive or link to the QTL (or loci) patterns in such populations 1250 could be easier to identify than in the case where cellular constituent data form the entire population is used as quantitative traits in such studies. An example where quantitative genetic analysis on subgroups identified genes associated with a trait of interest whereas comparable analysis using the population as a whole failed to identify such genes is found in Schadt et al., 2003, Nature 422, p. 297.

5.2. Sources of Marker Genotype Data

Several forms of genetic markers that are used as marker genotype data 78 (a marker map) are known in the art. A common genetic marker is single nucleotide polymorphisms (SNPs). SNPs occur approximately once every 600 base pairs in the genome. See, for example, Kruglyak and Nickerson, 2001, Nature Genetics 27, 235. The present invention contemplates the use of genotypic databases such as SNP databases as a source of marker genotype data 78. Alleles making up blocks of such SNPs in close physical proximity are often correlated, resulting in reduced genetic variability and defining a limited number of "SNP haplotypes" each of which reflects descent from a single ancient ancestral chromosome. See Fullerton et al., 2000, Am. J. Hum. Genet. 67, 881. Such haplotype structure is useful in selecting appropriate genetic variants for analysis. Patil et al. found that a very dense set of SNPs is required to capture all the common haplotype information. Once common haplotype information is available, it can be used to identify much smaller subsets of SNPs useful for comprehensive whole-genome studies. See Patil et al., 2001, Science 294, 1719-1723.

Other suitable sources of genetic markers include databases that have various types of gene expression data from platform types such as spotted microarray (microarray), high-density oligonucleotide array (UDA), hybridization filter (filter) and serial analysis of gene expression (SAGE) data. Another example of a genetic database that can be used is a DNA methylation database. For details on a representative DNA methylation database, see Grunau et al., in press, MethDB- a public database for DNA methylation data, Nucleic Acids Research; or the URL: genome.imb-jena.de/public.html.

In one embodiment of the present invention, a set of genetic markers (marker genotype data 78) is derived from any type of genetic database that tracks variations in the genome of an organism of interest. Information that is typically represented in such databases is a collection of loci within the genome of the organism of interest. For each locus, strains for which genetic variation information is available are represented. For each represented strain, variation information is provided. Variation information is any type of genetic variation information. Representative genetic variation information includes, but is not limited to, single nucleotide polymorphisms, restriction fragment length polymorphisms, microsatellite markers, restriction fragment length polymorphisms, and short tandem repeats. Therefore, suitable genotypic databases include, but are not limited to those disclosed in Table 1.

TABLE 1

Exemplary suitable genotypic databases

| Genetic variation type | Uniform resource location |
|---|---|
| SNP | bioinfo.pal.roche.com/usuka_bioinformatics/cgi-bin/msnp/msnp.pl |
| SNP | snp.cshl.org/ |
| SNP | ibc.wustl.edu/SNP/ |
| SNP | www-genome.wi.mit.edu/SNP/mouse/ |
| SNP | ncbi.nlm.nih.gov/SNP/ |
| Microsatellite markers | informatics.jax.org/searches/polymorphism_form.shtml |
| Restriction fragment length polymorphisms | informatics.jax.org/searches/polymorphism_form.shtml |
| Short tandem repeats | cidr.jhmi.edu/mouse/mmset.html |
| Sequence length polymorphisms | mcbio.med.buffalo.edu/mit.html |

TABLE 1-continued

Exemplary suitable genotypic databases

| Genetic variation type | Uniform resource location |
|---|---|
| DNA methylation database | genome.imb-jena.de/public.html |
| Short tandem-repeat polymorphisms | Broman et al., 1998, Comprehensive human genetic maps: Individual and sex-specific variation in recombination, American Journal of Human Genetics 63, 861-869 |
| Microsatellite markers | Kong et al., 2002, A high-resolution recombination map of the human genome, Nat Genet 31, 241-247 |

Each of the URLs, references, and databases listed in Table 1 are specifically incorporated by reference in their entireties.

In addition, the genetic variations used by the methods of the present invention may involve differences in the expression levels of genes rather than actual identified variations in the composition of the genome of the organism of interest. Therefore, genotypic databases within the scope of the present invention include a wide array of expression profile databases such as the one found at the URL: ncbi.nlm.nih.gov/geo/.

Another form of genetic marker that may be used as marker genotype data 78 (e.g., as a marker map) is restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et al., 1985, Plant Mol. Bio. 5:109-118, and U.S. Pat. No. 5,324,631). Another form of genetic marker that may be used as marker genotype data 78 (e.g., as a marker map) is random amplified polymorphic DNA (RAPD). The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213-7218; Hu and Quiros, 1991, Plant Cell Rep. 10:505-511). Yet another form of genetic marker map that may be used as marker genotype data 78 is amplified fragment length polymorphisms (AFLP). AFLP technology refers to a process that is designed to generate large numbers of randomly distributed molecular markers (see, for example, European Patent Application No. 0534858 A1). Still another form of marker genotype data 78 that can be used to construct a marker map is "simple sequence repeats" or "SSRs". SSRs are di-, tri- or tetra-nucleotide tandem repeats within a genome. The repeat region may vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, Theor. Appl. Genet. 93, 1071-1077; Bligh et al., 1995, Euphytica 86:83-85; Struss et al., 1998, Theor. Appl. Genet. 97, 308-315; Wu et al., 1993, Mol. Gen. Genet. 241, 225-235; and U.S. Pat. No. 5,075,217). SSRs are also known as satellites or microsatellites.

As described above, many genetic markers suitable for use with the present invention are publicly available. Those skilled in the art can also readily prepare suitable markers. For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., 7-21.

5.3. Exemplary Normalization Routines

A number of different normalization protocols may be used by normalization module 72 to normalize gene expression/cellular constituent data 44. Representative normalization protocols are described in this section. Typically, the normalization comprises normalizing the expression level measurement of each gene in a plurality of genes that is expressed by an organism in a population of interest. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publically available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij}=(I_{ij}-mnI_i)/sdI_i,$$

and $$Zdiff_j(x,y)=Z\text{-score}_{xj}-Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (medianI$_i$) for all of the spots in that sample. Thus, upon normalization by the median intensity normalization method, the raw intensity I$_{ij}$ for probe i and spot j, has the value Im$_{ij}$ where, $Im_{ij} = (I_{ij}/\text{median}I_i)$.

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (medianI$_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity I$_{ij}$ for probe i and spot j, has the value Im$_{ij}$ where, $Im_{ij} = \log(1.0 + (I_{ij}/\text{median}I_i))$.

Yet another normalization protocol is the Z-score standard deviation log of intensity protocol. In this protocol, raw expression intensities are normalized by the mean log intensity (mnLI$_i$) and standard deviation log intensity (sdLI$_i$). For microarray data, the mean log intensity and the standard deviation log intensity is computed for the log of raw intensity of control genes. Then, the Z-score intensity ZlogS$_{ij}$ for probe i and spot j is:

$Z \log S_{ij} = (\log(I_{ij}) - mnL_i)/sdLI_i$.

Still another normalization protocol is the Z-score mean absolute deviation of log intensity protocol. In this protocol, raw expression intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnLI$_i$ and the mean absolute deviation log intensity madLI$_i$ are computed for the log of raw intensity of control genes. Then, the Z-score intensity ZlogA$_{ij}$ for probe i and spot j is:

$Z \log A_{ij} = (\log(I_{ij}) - mnLI_i)/madLI_i$.

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. (see Section 5.8.1.5.). In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.4. Logarithmic of the Odds Scores

Denoting the joint probability of inheriting all genotypes P(g), and the joint probability of all observed data x (trait and marker species) conditional on genotypes P(x|g), the likelihood L for a set of data is $L = \Sigma P(g) P(x|g)$ where the summation is over all the possible joint genotypes g (trait and marker) for all pedigree members. What is unknown in this likelihood is the recombination fraction θ, on which P(g) depends.

The recombination fraction θ is the probability that two loci will recombine (segregate independently) during meioses. The recombination fraction θ is correlated with the distance between two loci. By definition, the genetic distance is defined to be infinity between the loci on different chromosomes (nonsyntenic loci), and for such unlinked loci, θ=0.5. For linked loci on the same chromosome (syntenic loci), θ<0.5, and the genetic distance is a monotonic function of θ. See, e.g., Ott, 1985, *Analysis of Human Genetic Linkage*, first edition, Baltimore, Md., John Hopkins University Press. The essence of linkage analysis described in Section 5.13, is to estimate the recombination fraction θ and to test whether θ=0.5. When the position of one locus in the genome is known, genetic linkage can be exploited to obtain an estimate of the chromosomal position of a second locus relative to the first locus. In linkage analysis described in Section 5.13, linkage analysis is used to map the unknown location of genes predisposing to various quantitative phenotypes relative to a large number of marker loci in a genetic map. In the ideal situation, where recombinant and nonrecombinant meioses can be counted unambiguously, θ is estimated by the frequency of recombinant meioses in a large sample of meioses. If two loci are linked, then the number of nonrecombinant meioses N is expected to be larger than the number of recombinant meioses R. The recombination fraction between the new locus and each marker can be estimated as:

$$\hat{\theta} = \frac{R}{N+R}$$

The likelihood of interest is:

$L = \Sigma P(g|\theta) P(x|g)$ and inferences are based about a test recombination fraction θ on the likelihood ratio $\Lambda = L(\theta)/L(1/2)$ or, equivalently, its logarithm.

Thus, in a typical clinical genetics study, the likelihood of the trait and a single marker is computed over one or more relevant pedigrees. This likelihood function L(θ) is a function of the recombination fraction θ between the trait (e.g., classical trait or quantitative trait) and the marker locus. The standardized loglikelihood $Z(\theta) = \log_{10}[L(\theta)/L(1/2)]$ is referred to as a lod score. Here, "lod" is an abbreviation for "logarithm of the odds." A lod score permits visualization of linkage evidence. As a rule of thumb, in human studies, geneticists provisionally accept linkage if $Z(\hat{\theta}) \geq 3$ at its maximum θ on the interval [0, 1/2], where $\hat{\theta}$ represents the maximum θ on the interval. Further, linkage is provisionally rejected at a particular θ if $Z(\hat{\theta}) \leq -2$.

Acceptance and rejection are treated asymmetrically because, with 22 pairs of human autosomes, it is unlikely that a random marker even falls on the same chromosome as a trait locus. See Lange, 1997, *Mathematical and Statistical Methods for Genetic Analysis*, Springer-Verlag, New York; Olson, 1999, Tutorial in Biostatistics: Genetic Mapping of Complex Traits, *Statistics in Medicine* 18, 2961-2981.

When the value of L is large, the null hypothesis of no linkage, L(1/2), to a marker locus of known location can be rejected, and the relative location of the locus corresponding to the quantitative trait can be estimated by $\hat{\theta}$. Therefore, lod scores provide a method to calculate linkage distances as well as to estimate the probability that two genes (and/or QTLs) are linked.

In some embodiments of the lod score method, a series of lod scores are calculated from a number of proposed linkage distances. First, a linkage distance is estimated, and given that estimate, the probability of a given birth sequence is calculated. That value is then divided by the probability of a given birth sequence assuming that the genes (and/or QTLs) are unlinked (L(1/2)). The log of this value is calculated, and that value is the lod score for this linkage distance estimate. The same process is repeated with another linkage distance estimate. A series of these lod scores are obtained using different linkage distances, and the linkage distance giving the highest lod score is considered the estimate of the linkage distance.

Those of skill in the art will appreciate that lod score computation is species dependent. For example, methods for computing the lod score in mouse different from that described in this section. However, methods for computing lod scores are known in the art and the method described in this section is only by way of illustration and not by limitation.

5.5. Clustering Techniques

The subsections below describe exemplary methods for clustering gene analysis vectors. In these techniques, gene analysis vectors are clustered based on the strength of interaction between the gene analysis vectors. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; Backer, 1995, *Computer-Assisted Reasoning in Cluster Analysis*, Prentice Hall, Upper Saddle River, N.J.; and Duda et al., 2001, *Pattern Classification*, John Wiley & Sons, New York, N.Y.

5.5.1. Hierarchical Clustering Techniques

Hierarchical cluster analysis is a statistical method for finding relatively homogenous clusters of elements based on measured characteristics. Consider a sequence of partitions of n samples into c clusters. The first of these is a partition into n clusters, each cluster containing exactly one sample. The next is a partition into n−1 clusters, the next is a partition into n−2, and so on until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, then the sequence is said to be a hierarchical clustering. Duda et al., 2001, *Pattern Classification*, John Wiley & Sons, New York, 2001, p. 551.

5.5.1.1. Agglomerative Clustering

In some embodiments, the hierarchical clustering technique used to cluster gene analysis vectors is an agglomerative clustering procedure. Agglomerative (bottom-up clustering) procedures start with n singleton clusters and form a sequence of partitions by successively merging clusters. The major steps in agglomerative clustering are contained in the following procedure, where c is the desired number of final clusters, $D_i$ and $D_j$ are clusters, $x_i$ is a gene analysis vector, and there are n such vectors:

```
1    begin initialize c, ĉ ←n, D_i ←{x_i}, i = 1, ..., n
2        do ĉ ←ĉ −1
3            find nearest clusters, say, D_i and D_j
4            merge D_i and D_j
5        until c = ĉ
6        return c clusters
7    end
```

In this algorithm, the terminology a←b assigns to variable a the new value b. As described, the procedure terminates when the specified number of clusters has been obtained and returns the clusters as a set of points. A key point in this algorithm is how to measure the distance between two clusters $D_i$ and $D_j$. The method used to define the distance between clusters $D_i$ and $D_j$ defines the type of agglomerative clustering technique used. Representative techniques include the nearest-neighbor algorithm, farthest-neighbor algorithm, the average linkage algorithm, the centroid algorithm, and the sum-of-squares algorithm.

Nearest-neighbor algorithm. The nearest-neighbor algorithm uses the following equation to measure the distances between clusters:

$$d\min(Di, Dj) = \min_{\substack{x \in Di \\ x' \in Dj}} \|x - x'\|.$$

This algorithm is also known as the minimum algorithm. Furthermore, if the algorithm is terminated when the distance between nearest clusters exceeds an arbitrary threshold, it is called the single-linkage algorithm. Consider the case in which the data points are nodes of a graph, with edges forming a path between the nodes in the same subset $D_i$. When dmin( ) is used to measure the distance between subsets, the nearest neighbor nodes determine the nearest subsets. The merging of $D_i$ and $D_j$ corresponds to adding an edge between the nearest pair of nodes in $D_i$ and $D_j$. Because edges linking clusters always go between distinct clusters, the resulting graph never has any closed loops or circuits; in the terminology of graph theory, this procedure generates a tree. If it is allowed to continue until all of the subsets are linked, the result is a spanning tree. A spanning tree is a tree with a path from any node to any other node. Moreover, it can be shown that the sum of the edge lengths of the resulting tree will not exceed the sum of the edge lengths for any other spanning tree for that set of samples. Thus, with the use of dmin( ) as the distance measure, the agglomerative clustering procedure becomes an algorithm for generating a minimal spanning tree. See Duda et al., id, pp. 553-554.

Farthest-neighbor algorithm. The farthest-neighbor algorithm uses the following equation to measure the distances between clusters:

$$d\max(Di, Dj) = \max_{\substack{x \in Di \\ x' \in Dj}} \|x - x'\|.$$

This algorithm is also known as the maximum algorithm. If the clustering is terminated when the distance between the nearest clusters exceeds an arbitrary threshold, it is called the complete-linkage algorithm. The farthest-neighbor algorithm discourages the growth of elongated clusters. Application of this procedure can be thought of as producing a graph in which the edges connect all of the nodes in a cluster. In the terminology of graph theory, every cluster contains a complete subgraph. The distance between two clusters is terminated by the most distant nodes in the two clusters. When the nearest clusters are merged, the graph is changed by adding edges between every pair of nodes in the two clusters.

Average linkage algorithm. Another agglomerative clustering technique is the average linkage algorithm. The average linkage algorithm uses the following equation to measure the distances between clusters:

$$d_{avg}(Di, Dj) = \frac{1}{n_i n_j} \sum_{x \in Di} \sum_{x' \in Dj} \|x - x'\|.$$

Hierarchical cluster analysis begins by making a pair-wise comparison of all gene analysis vectors in a set of such vectors. After evaluating similarities from all pairs of elements in the set, a distance matrix is constructed. In the distance matrix, a pair of vectors with the shortest distance (i.e. most similar values) is selected. Then, when the average linkage algorithm is used, a "node" ("cluster") is constructed by averaging the two vectors. The similarity matrix is updated with the new "node" ("cluster") replacing the two joined elements, and the process is repeated n−1 times until only a single element remains. Consider six elements, A-F having the values:

A{4.9}, B{8.2}, C{3.0}, D{5.2}, E{8.3}, F{2.3}.

In the first partition, using the average linkage algorithm, one matrix (sol. 1) that could be computed is:

A {4.9}, B-E{8.25}, C{3.0}, D{5.2}, F{2.3}. (sol. 1)

Alternatively, the first partition using the average linkage algorithm could yield the matrix:

A {4.9}, C{3.0}, D{5.2}, E-B{8.25}, F{2.3}. (sol. 2)

Assuming that solution 1 was identified in the first partition, the second partition using the average linkage algorithm will yield:

A-D{5.05}, B-E{8.25}, C{3.0}, F{2.3} (sol. 1-1)

or

B-E{8.25}, C{3.0}, D-A{5.05}, F{2.3}. (sol. 1-2)

Assuming that solution 2 was identified in the first partition, the second partition of the average linkage algorithm will yield:

A-D{5.05}, C{3.0}, E-B{8.25}, F{2.3} (sol. 2-1)

or

C{3.0}, D-A{5.05}, E-B{8.25}, F{2.3}. (sol. 2-2)

Thus, after just two partitions in the average linkage algorithm, there are already four matrices. See Duda et al., Pattern Classification, John Wiley & Sons, New York, 2001, p. 551.

Centroid algorithm. In the centroid method, the distances or similarities are calculated between the centroids of the clusters D.

Sum-of-squares algorithm. The sum of squares method is also known as the "Wards' method." In the Wards' method, cluster membership is assessed by calculating the total sum of squared deviations from the mean of a cluster. See Lance and Williams, 1967, A general theory of classificatory sorting strategies, *Computer Journal* 9: 373-380.

5.5.1.2. Clustering with Pearson Correlation Coefficients

In one embodiment of the present invention, gene analysis vectors are clustered using agglomerative hierarchical clustering with Pearson correlation coefficients. In this form of clustering, similarity is determined using Pearson correlation coefficients between the gene analysis vector pairs or gene expression vector pairs. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics may be computed using SAS (Statistics Analysis Systems Institute, Cary, N.C.) or S-Plus (Statistical Sciences, Inc., Seattle, Wash.).

5.5.1.3. Divisive Clustering

In some embodiments, the hierarchical clustering technique used to cluster gene analysis vectors is a divisive clustering procedure. Divisive (top-down clustering) procedures start with all of the samples in one cluster and form the sequence by successively splitting clusters. Divisive clustering techniques are classified as either a polythetic or a monthetic method. A polythetic approach divides clusters into arbitrary subsets.

5.5.2. K-Means Clustering

In k-means clustering, sets of gene analysis vectors are randomly assigned to K user specified clusters. The centroid of each cluster is computed by averaging the value of the vectors in each cluster. Then, for each i=1, . . . , N, the distance between vector $x_i$ and each of the cluster centroids is computed. Each vector $x_i$ is then reassigned to the cluster with the closest centroid. Next, the centroid of each affected cluster is recalculated. The process iterates until no more reassignments are made. See Duda et al., id., pp. 526-528. A related approach is the fuzzy k-means clustering algorithm, which is also known as the fuzzy c-means algorithm. In the fuzzy k-means clustering algorithm, the assumption that every gene analysis vector is in exactly one cluster at any given time is relaxed so that every vector has some graded or "fuzzy" membership in a cluster. See Duda et al., id., pp. 528-530.

5.5.3. Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput.*, C-22: 1025-1034, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_{min}$ of their K nearest-neighbors in common, where K and $k_{min}$ are user-defined parameters. The method has been widely applied to clustering chemical structures on the basis of fragment descriptors and has the advantage of being much less computationally demanding than hierarchical methods, and thus more suitable for large databases. Jarvis-Patrick clustering may be performed using the Jarvis-Patrick Clustering Package 3.0 (Barnard Chemical Information, Ltd., Sheffield, United Kingdom).

5.5.4. Neural Networks

A neural network has a layered structure that includes a layer of input units (and the bias) connected by a layer of weights to a layer of output units. In multilayer neural networks, there are input units, hidden units, and output units. In fact, any function from input to output can be implemented as a three-layer network. In such networks, the weights are set based on training patterns and the desired output. One method for supervised training of multilayer neural networks is back-propagation. Back-propagation allows for the calculation of an effective error for each hidden unit, and thus derivation of a learning rule for the input-to-hidden weights of the neural network.

The basic approach to the use of neural networks is to start with an untrained network, present a training pattern to the input layer, and pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

5.5.5. Self-Organizing Maps

A self-organizing map is a neural-network that is based on a divisive clustering approach. The aim is to assign genes to a series of partitions on the basis of the similarity of their expression vectors to reference vectors that are defined for each partition. Consider the case in which there are two microarrays from two different experiments. It is possible to build up a two-dimensional construct where every spot corresponds to the expression levels of any given gene in the two experiments. A two-dimensional grid is built, resulting in several partitions of the two-dimensional construct. Next, a gene is randomly picked and the identify of the reference vector (node) closest to the gene picked is determined based on a distance matrix. The reference vector is then adjusted so that it is more similar to the vector of the assigned gene. That means the reference vector is moved one distance unit on the x axis and y-axis and becomes closer to the assigned gene. The other nodes are all adjusted to the assigned gene, but only are moved one half or one-fourth distance unit. This cycle is repeated hundreds of thousands times to converge the reference vector to fixed value and where the grid is stable. At that time, every reference vector is the center of a group of genes. Finally, the genes are mapped to the relevant partitions depending on the reference vector to which they are most similar.

5.6. Multivariate Statistical Models

Once a set of genes have been identified that potentially are the target of a trait, multivariate statistical models can be applied to determine whether each of the genes in the set affect the trait, such as a complex disease trait. The form of multivariate statistical analysis used in some embodiments of the present invention is dependent upon on the type of marker genotype data 78 or pedigree data 74 (FIG. 1) that is available. Typically, more pedigree data is available in cases where the population to be studied is plants or animals. In such instances, the multivariate statistical models used are in accordance with those of Jiang and Zeng, 1995, Multiple trait analysis of genetic mapping for quantitative trait loci, Nature Genetics 140:1111-1127 as well as the techniques implemented in QTL Cartographer (Basten and Zeng, 1994, Zmap-a QTL cartographer, *Proceedings of the 5th World Congress on Genetics Applied to Livestock Production: Computing Strategies and Software*, Smith et al. eds., 22:65-66, The Organizing Committee, 5th World Congress on Genetics Applied to Livestock Production, Guelph, Ontario, Canada; Basten et al., 2001, *QTL Cartographer, Version* 1.15, Department of Statistics, North Carolina State University, Raleigh, N.C. For human marker genotype data 78 and/or pedigree data 74 (FIG. 1), methods described in Allison, 1998, Multiple Phenotype Modeling in Gene-Mapping Studies of Quantitative Traits: Power Advantages, *Am J. Hum. Genetics* 63:1190-1201 are used, including, but not limited to, those of Amos et al., 1990, A Multivariate Method for Detecting Genetic Linkage, with Application to a Pedigree with an Adverse Lipoprotein Protein, *Am J. Hum. Genetics* 47:247-254.

5.7. Analytic Kit Implementation

In a preferred embodiment, the methods of this invention can be implemented by use of kits for determining the responses or state of a biological sample. Such kits contain microarrays, such as those described in Subsections below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In one embodiment, a kit of the invention also contains one or more databases described above and in FIG. 1, encoded on computer readable medium, and/or an access authorization to use the databases described above from a remote networked computer.

In another embodiment, a kit of the invention further contains software capable of being loaded into the memory of a computer system such as the one described supra, and illustrated in FIG. 1. The software contained in the kit of this invention, is essentially identical to the software described above in conjunction with FIG. 1. Alternative kits for implementing the analytic methods of this invention will be apparent to one of skill in the art and are intended to be comprehended within the accompanying claims. In some embodiments, the software contained in the kit implements the methods illustrated in FIG. 2A or FIG. 2B.

5.8. Transcriptional State Measurements

The section provides some exemplary methods for measuring the expression level of genes, which are one type of cellular constituent. One of skill in the art will appreciate that this invention is not limited to the following specific methods for measuring the expression level of cellular constituents (e.g., genes) in each organism 46 in a plurality of organisms 46.

5.8.1. Transcript Assay Using Microarrays

The techniques described in this section are particularly useful for the determination of the expression state or the transcriptional state of a cell or cell type or any other cell sample by monitoring expression profiles. These techniques include the provision of polynucleotide probe arrays for simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance rations. Preferably, measurement of the expression profile is made by hybridization to transcript arrays, which are described in this subsection. In one embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to a drug of interest or to perturbations to a biological pathway of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 $cm^2$ and 25 $cm^2$, preferably about 1 to 3 $cm^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. In some embodiments, such polynucleotides are of the length of 15 to 200 bases. In other embodiments, such polynucleotides are of length 20 to 100 bases. In still other embodiments, such polynucleotides are of length 40 to 60 bases. However, the size of such polynucleotides is highly application dependent Accordingly, other sizes are possible. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon. However, if desired, the profiling arrays may contain at least 2, 5, 10, 100, 1000, or more probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such embodiments, an exon is represented by a single binding site on the profiling arrays. In some preferred embodiments of the invention, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15-600 bases, preferably between about 20-200 bases, more preferably between about 30-100 bases, and most preferably between about 40-80 bases. The average length of an exon is about 50 bases (See The Genome Sequencing Consortium, 2001, Initial sequencing and analysis of the human genome, Nature 409, 860-921). A probe of length of about 40-80 allows more specific binding of the exon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occur in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546-567). In contrast, the human genome is estimated to contain approximately 30,000 to 40,000 genes (see Venter et al., 2001, The Sequence of the Human Genome, *Science* 291:1304-1351). In some embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exon expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, *Science* 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.8.1.1. Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g. using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.8.1.2. Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., Biosensors & Bioelectronics 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.8.1.3. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. Pat. No. 6,271,002, and PCT Publication No. WO 02/44399 dated Jun. 6, 2002). Both oligo-dT primers (U.S. Pat. Nos. 5,545,522 and 6,132,997) or random primers (PCT WO 02/44399 dated Jun. 6, 2002) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefnic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'-carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluoescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.8.1.4. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.8.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled DNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of differences of an order of about 1.5 fold to about 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.8.2. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. USA* 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

5.9. Translational State Measurements

In various embodiments of the present invention, aspects of the biological state other than the transcriptional state, such as the translational state, the activity state, or mixed aspects can be measured. Thus, in such embodiments, cellular constituent data 44 (FIG. 1) may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in the this and following sections.

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274:536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.10. Measuring Other Aspects of the Biological State

The methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from the organism 46 (FIG. 1) of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes may be recorded as often as several times each hour. During one incubation, more than 5,000 phenotypes can be tested. See, for example, Bochner et al., 2001, Genome Research 11, 1246-55.

In some embodiments of the present invention, the cellular constituents that are measured (gene expression data 44) are metabolites. Metabolites include, but are not limited to, amino acids, metals, soluble sugars, sugar phosphates, and complex carbohydrates. Such metabolites may be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, J. Gen. Microbiol. 137, 69-79; Naumann et al., 1991, Nature 351, 81-82; Naumann et al., 1991, *In: Modern techniques for rapid microbiological analysis*, 43-96, Nelson, W. H., ed., VCH Publishers, New York), Raman spectrometry, gas chromatagraphy-mass spectroscopy (GC-MS) (Fiehn et al., 2000, Nature Biotechnology 18, 1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods may be combined with established chemometric methods that make use of artificial neural networks and genetic programming in order to discriminate between closely related samples.

5.11. Traits

In some embodiments of the present invention, the term "trait" refers clinical traits that exhibit classic Mendelian inheritance. In some embodiments, the term "trait" refers to clinical traits that are complex. That is, the term "trait" encompasses clinical traits that do not exhibit classic Mendelian inheritance.

In some embodiments, the term "trait" refers to a trait that is affected by two or more gene loci. In some embodiments, the term "trait" refers to a trait that is affected by two or more gene loci in addition to one or more factors including, but not limited to, age, sex, habits, and environment. See, for example, Lander and Schork, 1994, Science 265: 2037. Such "complex" traits include, but are not limited to, susceptibilities to heart disease, hypertension, diabetes, obesity, cancer, and infection. Complex traits arise when the simple correspondence between genotype and phenotype breaks down, either because the same genotype can result in different phenotypes (due to the effect of chance, environment, or interaction with other genes) or different genotypes can result in the same phenotype.

In some embodiments, a complex trait is one in which there exists no genetic marker that shows perfect cosegregation with the trait due to incomplete penetrance, phenocopy, and/or nongenetic factors (e.g., age, sex, environment, and affect or other genes). Incomplete penetrance means that some individuals who inherit a predisposing allele may not manifest the disease. Phenocopy means that some individuals who inherit no predisposing allele may nonetheless get the disease as a result of environmental or random causes. Thus, the genotype at a given locus may affect the probability of disease, but not fully determine the outcome. The penetrance function $f(G)$, specifying the probability of disease for each genotype G, may also depend on nongenetic factors such as age, sex, environment, and other genes. See, for example, Easton et al., 1993, *Cancer Surv.* 18, p. 1995; Ford et al., 1994, *Lancet* 343, p. 692. In some embodiments a complex trait arises because any one of several genes may result in identical phenotypes (genetic heterogeneity). In cases where there is genetic heterogeneity, it may be difficult to determine whether two patients suffer from the same disease for different genetic reasons until the genes are mapped. Examples of complex traits that are diseases are discussed in Section 5.12, below.

In still other embodiments, a complex trait arises due to the phenomenon of polygenic inheritance. Polygenic inheritance arises when a trait requires the simultaneous presence of mutations in multiple genes. An example of polygenic inheritance in humans is one form of retinitis pigmentosa, which requires the presence of heterozygous mutations at the perpherin/RDS and ROM1 genes (Kajiwara et al., 1994, Science 264: 1604). It is believed that the proteins coded by RDS and ROM1 are thought to interact in the photoreceptor outer pigment disc membranes. Polygenic inheritance complicates genetic mapping, because no single locus is strictly required to produce a discrete trait or a high value of a quantitative trait.

In yet other embodiments, a complex trait arises due to a high frequency of disease-causing allele "D". A high frequency of disease-causing allele will cause difficulties in mapping even a simple trait if the disease-causing allele occurs at high frequency in the population. That is because the expected Mendelian inheritance pattern of disease will be confounded by the problem that multiple independent copies of D may be segregating in the pedigree and that some individuals may be homozygous for D, in which case one will not observe linkage between D and a specific allele at a nearby genetic marker, because either of the two homologous chromosomes could be passed to an affected offspring. Late-onset Alzheimer's disease provides one example of a high frequency disease-causing alleles. See, for example, Pericak-Vance et al., 1991, *Am J. Hum. Genet.* 48: 1034; and Corder et al., 1993, *Science* 261: 921.

5.12. Exemplary Diseases

Exemplary diseases include asthma, ataxia telangiectasia (Jaspers and Bootsma, 1982, *Proc. Natl. Acad. Sci. U.S.A.* 79: 2641), bipolar disorder, common cancers, common late-onset Alzheimer's disease, diabetes, heart disease, hereditary early-onset Alzheimer's disease (George-Hyslop et al., 1990, *Nature* 347: 194), hereditary nonpolyposis colon cancer, hypertension, infection, maturity-onset diabetes of the young (Barbosa et al., 1976, *Diabete Metab.* 2: 160), mellitus, migraine, nonalcoholic fatty liver (NAFL) (Younossi, et al., 2002, Hepatology 35, 746-752), nonalcoholic steatohepatitis (NASH) (James & Day, 1998, *J. Hepatol.* 29: 495-501), non-insulin-dependent diabetes mellitus, obesity, polycystic kidney disease (Reeders et al., 1987, *Human Genetics* 76: 348), psoriases, schizophrenia, steatohepatitis and xeroderma pigmentosum (De Weerd-Kastelein, *Nat. New Biol.* 238: 80). Genetic heterogeneity hampers genetic mapping, because a chromosomal region may cosegregate with a disease in some families but not in others.

5.13. Linkage Analysis

This section describes a number of standard quantitative trait locus (QTL) linkage analysis algorithms that can be used in various steps in the method disclosed in FIG. 2A and FIG. 2B. The primary aim of linkage analysis is to determine whether there exists pieces of the genome that are passed down through each of several families with multiple afflicted organisms in a pattern that is consistent with a particular inheritance model and that is unlikely to occur by chance alone. In other words, the purpose of these algorithms is to identify a loci (e.g., a QTL) for a phenotypic trait exhibited by one or more organisms 46. A QTL is a region of a genome of a species that is responsible for a percentage of variation in a phenotypic trait in the species under study. Linkage analyses can generally be divided into two classes: model-based linkage analysis (Section 5.13.1) and model-free linkage analysis (Section 5.13.2). Model-based linkage analysis assumes a model for the mode of inheritance whereas model-free linkage analysis does not assume a mode of inheritance. Model-free linkage analyses are also known as allele-sharing methods and non-parametric linkage methods. Model-based linkage analyses are also known as "maximum likelihood" and "lod score" methods. Either form of linkage analysis can be used in the various steps disclosed in FIG. 2A and FIG. 2B. For more information on model-based and model-free linkage analysis, see Olson et al., 1999, Statistics in Medicine 18, p. 2961-2981; Lander and Schork 1994, Science 265, p. 2037; and Elston, 1998, Genetic Epidemiology 15, p. 565.

The recombination fraction can be denoted by $\theta$ and is bounded between 0 and 0.5. If $\theta=0.5$ for two loci, then alleles at the two loci are transmitted independently with half of the gametes being recombinant, for the two loci, and half parental. In this case, the loci are unlinked. If $\theta<0.5$, then alleles are not transmitted independently, and the two loci are linked. The extreme scenario is when $\theta=0$, so that the two loci are completely linked, and there will be no recombination between the two loci during meiosis, i.e. all gametes are parental. Linkage analysis test whether a marker locus, of known location, is linked to a locus of unknown location, that influences the phenotype under study. As mentioned above, there are essentially two types of linkage analysis. The first of which (model-based linkage analysis) is most often used for dichotomous traits and requires assumptions for the disease model. These assumptions include the disease allele frequency and penetrance function. For most diseases of interest, particularly those of interest to public health, the true underlying model is complex and unknown, so that these procedures are not applicable. The other form of linkage analysis (model-free linkage analysis) makes use of allele-sharing. Allele-sharing methods rely on the idea that relatives with similar phenotypes should have similar genotypes at a marker locus if and only if the marker is linked to the locus of interest. Linkage analyses are able to localize the locus of interest to a specific region of a chromosome, but the scope of resolution is typically limited to no more than 1 cM or roughly 1000 kb, due to the limited number of informative meioses in the data.

Many known programs can be used to perform linkage analysis in accordance with this aspect of the invention. One such program is MapMaker/QTL, which is the companion program to MapMaker and is the original QTL mapping software. MapMaker/QTL analyzes F2 or backcross data using standard interval mapping. Another such program is QTL Cartographer, which performs single-marker regression, interval mapping (Lander and Botstein, Id.), multiple interval mapping and composite interval mapping (Zeng, 1993, PNAS 90: 10972-10976; and Zeng, 1994, Genetics 136: 1457-1468). QTL Cartographer permits analysis from F2 or backcross populations. QTL Cartographer is available from statgen.ncsu.edu/qtlcart/cartographer.html (North Carolina State University). Another program that can be used by processing step 114 is Qgene, which performs QTL mapping by either single-marker regression or interval regression (Martinez and Curnow 1994 Heredity 73:198-206). Using Qgene, eleven different population types (all derived from inbreeding) can be analyzed. Qgene is available from gene-.orgl. Yet another program is MapQTL, which conducts standard interval mapping (Lander and Botstein, Id.), multiple QTL mapping (MQM) (Jansen, 1993, Genetics 135: 205-211; Jansen, 1994, Genetics 138: 871-881), and nonparametric mapping (Kruskal-Wallis rank sum test). MapQTL can analyze a variety of pedigree types including outbred pedigrees (cross pollinators). MapQTL is available from Plant Research International, Plant Research International, P.O. Box 16, 6700 AA Wageningen, The Netherlands; plant-.wageningen-ur.nl/default.asp?section=products). Yet another program that may be used in some embodiments of processing step 210 is Map Manager QT, which is a QTL mapping program (Manly and Olson, 1999, Mamm Genome 10: 327-334). Map Manager QT conducts single-marker regression analysis, regression-based simple interval mapping (Haley and Knott, 1992, Heredity 69, 315-324), composite interval mapping (Zeng 1993, PNAS 90: 10972-10976), and permutation tests. A description of Map Manager QT is provided by the reference Manly and Olson, 1999, Overview of QTL mapping software and introduction to Map Manager QT, Mammalian Genome 10: 327-334. Yet another program that may be used to perform linkage analysis is MultiCross QTL, which maps QTL from crosses originating from inbred lines. MultiCross QTL uses a linear regression-model approach and handles different methods such as interval mapping, all-marker mapping, and multiple QTL mapping with cofactors. The program can handle a wide variety of simple mapping populations for inbred and outbred species. MultiCross QTL is available from Unité de Biometrie et Intelligence Artificielle, INRA, 31326 Castanet Tolosan, France.

Still another program that can be used to perform linkage analysis is QTL Café. The program can analyze most populations derived from pure line crosses such as F2 crosses, backcrosses, recombinant inbred lines, and doubled haploid lines. QTL Café incorporates a Java implementation of Haley & Knotts' flanking marker regression as well as Marker regression, and can handle multiple QTLs. The program allows three types of QTL analysis single marker ANOVA, marker regression (Kearsey and Hyne, 1994, Theor. Appl. Genet., 89: 698-702), and interval mapping by regression, (Haley and Knott, 1992, Heredity 69: 315-324). QTL Café is available from web.bham.ac.uk/g.g.seaton/.

Yet another program that can be used to perform linkage analysis is MAPL, which performs QTL analysis by either interval mapping (Hayashi and Ukai, 1994, Theor. Appl. Genet. 87:1021-1027) or analysis of variance. Different population types including F2, back-cross, recombinant inbreds derived from F2 or back-cross after a given generations of selfing can be analyzed. Automatic grouping and ordering of numerous markers by metric multidimensional scaling is possible. MAPL is available from the Institute of Statistical Genetics on Internet (ISGI), Yasuo, UKAI, peach.ab.a.u-tokyo.ac.jp/-ukai/.

Another program that can be used for linkage analysis is R/qtl. This program provides an interactive environment for mapping QTLs in experimental crosses. R/qtl makes uses of the hidden Markov model (HMM) technology for dealing with missing genotype data. Rlqtl has implemented many HMM algorithms, with allowance for the presence of genotyping errors, for backcrosses, intercrosses, and phase-known four-way crosses. R/qtl includes facilities for estimating genetic maps, identifying genotyping errors, and performing single-QTL genome scans and two-QTL, two-dimensional genome scans, by interval mapping with Haley-Knott regression, and multiple imputation. R/qtl is available from Karl W. Broman, Johns Hopkins University, biosun01.biostat.jhsph.edu/~kbroman/qtl/.

5.13.1. Model-Based Parametric Linkage Analysis

A QTL is identified by comparing genotypes of organisms in a group to a phenotype exhibited by the group using pedigree data. The genotype of each organism 46 at each marker in a plurality of markers in a genetic map produced by marker genotypic data 78 is compared to a given phenotype of each organism 46. The genetic map is created by placing genetic markers in genetic (linear) map order so that the relationships between markers are understood. The information gained from knowing the relationships between markers that is provided by a marker map provides the setting for addressing the relationship between QTL effect and QTL location.

In order to provide the necessary genotypic data for the QTL analysis, the genotype of each marker in the genetic marker map 78 is determined for each organism 46. Representative genotypic information includes, but is not limited to, single nucleotide polymorphisms, microsatellite markers, restriction fragment length polymorphisms, short tandem repeats, sequence length polymorphisms, and DNA methylation patterns.

Linkage analysis requires pedigree data 74 for each organism 46 in order to statistically model the segregation of markers. In some embodiments, populations under study are constructed from populations that originate from homozygous, inbred parental lines. The resulting $F_1$, lines will be heterozygous at all loci. From the $F_1$, population, crosses are made. Exemplary crosses include backcrosses and $F_2$ intercrosses. Thus, in some embodiments of the present invention, organisms 46 represent a population, such as an $F_2$ population, and pedigree data for the $F_2$ population is known. This pedigree data is used to compute logarithm of the odds (LOD) scores, as discussed in further detail below.

Linkage analyses use the genetic map derived from marker genotypic data 78 as the framework for location of QTL for any given quantitative trait. The intervals that are defined by ordered pairs of markers are searched in increments (for example, 2 cM), and statistical methods are used to test whether a QTL is likely to be present at the location within the interval. In one embodiment, linkage analysis statistically tests for a single QTL at each increment across the ordered markers in a genetic map. The results of the tests are expressed as lod scores, which compares the evaluation of the likelihood function under a null hypothesis (no QTL) with the alternative hypothesis (QTL at the testing position) for the purpose of locating probable QTL. More details on lod scores are found in Section 5.4, below, as well as in Lander and Schork, 1994, Science 265, p. 2037-2048. Interval mapping searches through the ordered genetic markers in a systematic, linear (one-dimensional) fashion, testing the same null hypothesis and using the same form of likelihood at each increment.

In some embodiments, linkage analysis comprises finding a model $M_1$, positing a specific location for a trait-causing gene, that is much more likely to have produced the observed data than a null hypothesis $M_0$, positing no linkage to a trait-causing gene in the region. The evidence for $M_1$ versus $M_0$ is measured by the likelihood ratio, LR=Prob (Data $M_1$)/ (Data $M_0$), or, equivalently, by the lod score, $Z=\log_{10}(LR)$. See, for example, Barnard, 1949, R. Stat. Soc. J. B11, p. 115; Haldane and Smith, 1947, Ann. Eugen. 14, p. 10; Chotoi, 1984, Ann. Hum. Genet. 48, p. 359; Morton, 1955, Am J. Hum. Genet. 8, p. 80.

The model $M_1$ is typically chosen from among a family of models $M(\Phi)$, where $\Phi$ is a parameter vector that might specify such information as the location of the trait causing locus, the allele frequencies at the trait and marker loci, the penetrance function, and the transmission frequencies from parent to child. In some embodiments, a model describes a transmission probability (the probability that a parental genotype transmits a particular allele or haplotype to an offspring), a penetrance function (the probability of a phenotype given a genotype), and an allele frequency (the distribution of relative frequencies of alleles in a population). Many of these parameters may already be estimated from prior studies (such as penetrance functions from prior segregation analysis or marker allele frequencies from population surveys). The remaining, unknown parameters are chosen to be the maximum likelihood estimate (ML) estimate, that is, the value $\Phi'$ that makes the data most likely to have occurred. See, for example, Edwards, 1992, *Likelihood*, John Hopkins University Press, Baltimore, Md., 1992. The null model $M_0$ corresponds to a specific null hypothesis about the parameters, $\Phi_0$.

For example, the model for a simple Mendelian recessive or dominant disease in cases where inbred lines crosses are used, is completely specified except for the recombination frequency θ between the disease gene and a marker and the allele frequencies; the null hypothesis of nonlinkage corresponds to θ=fifty percent recombination. The ML model $M(\Phi')$ is accepted (compared with M0) if the corresponding maximum lod score Z' is large, that is, exceeds a critical threshold T. However, to use this test in cases where inbred lines are not available (e.g., humans) marker and QTL allele frequencies are needed.

In one embodiment of the present invention, linkage analysis comprises QTL interval mapping in accordance with algorithms derived from those first proposed by Lander and Botstein, 1989, "Mapping mendelian factors underlying quantitative traits using RFLP linkage maps," Genetics 121: 185-199. The principle behind interval mapping is to test a model for the presence of a QTL at many positions between two mapped marker loci. The model is fit, and its goodness is tested using a technique such as the maximum likelihood method. Maximum likelihood theory assumes that when a QTL is located between two biallelic markers, the genotypes (i.e. AABB, AAbb, aaBB, aabb for doubled haploid progeny) each contain mixtures of quantitative trait locus (QTL) genotypes. Maximum likelihood involves searching for QTL parameters that give the best approximation for quantitative trait distributions that are observed for each marker class. Models are evaluated by computing the likelihood of the observed distributions with and without fitting a QTL effect.

In some embodiments of the present invention, linkage analysis is performed using the algorithm of Lander, as implemented in programs such as GeneHunter. See, for example, Kruglyak et al., 1996, Parametric and Nonparametric Linkage Analysis: A Unified Multipoint Approach, American Journal of Human Genetics 58:1347-1363, Kruglyak and Lander, 1998, Journal of Computational Biology 5:1-7; Kruglyak, 1996, American Journal of Human Genetics 58, 1347-1363. In such embodiments, unlimited markers may be used but pedigree size is constrained. In other embodiments, the MENDEL software package is used. (See bimas.dcrt.nih.gov/linkage/ltools.html). In such embodiments, the size of the pedigree can be unlimited but the number of markers that can be used is constrained. Those of skill in the art will appreciate that there are several other programs and algorithms that can be used in certain steps in the method disclosed in FIG. 2A and FIG. 2B and all such programs and algorithms are within the scope of the present invention.

In some embodiments of the present invention, linkage analysis is based on regression methodology and gives estimates of QTL position and effect that are similar to those given by the maximum likelihood method. Since the QTL genotypes are unknown in mapping based on regression methodology, genotypes are replaced by probabilities estimated using genotypes at the nearest flanking markers. See, e.g., Haley and Knott, 1992, "A simple regression method for mapping quantitative trait loci in line crosses using flanking markers," Heredity 69, 315-324.

5.13.2. Model-Free Linkage Analysis

Model-based linkage analysis (classical linkage analysis) calculates a lod score that represents the chance that a given loci in the genome is genetically linked to a trait, assuming a specific mode of inheritance for the trait. Namely the allele frequencies and penetrance values are included as parameters and are subsequently estimated. In one approach, particular risks for a genetically normal subject to be a phenocopy and for a genetically abnormal subject to be a non-penetrant carrier are assigned. However, when the trait exhibits non-mendelian segregation it can be difficult to obtain reliable estimates of penetrance values, including phenocopy risks, and the allele frequency of the disease mutation. Indeed it may be the case that different mutations at different loci have different kinds of effect on susceptibility, some major and some minor, some dominant and some recessive. If different modes of transmission are operative in different families, or if different loci interact in the same family, then no one transmission model may be appropriate. It is conceivable that if the transmission model for a linkage analysis is specified incorrectly the results produced from it will not be valid nor interpretable. As a result, a variety of methods have been developed to test for linkage without the need to specify values for the parameters defining the transmission model, and these methods are termed model-free linkage analyses (meaning that they can be applied without regard to the true transmission model).

Model-free linkage analyses (allele-sharing methods) are not based on constructing a model, but rather on rejecting a model. Specifically, one tries to prove that the inheritance pattern of a chromosomal region is not consistent with random Mendelian segregation by showing that affected relatives inherit identical copies of the region more often then expected by chance. Affected relatives should show excess allele sharing even in the presence of incomplete penetrance, phenocopy, genetic heterogeneity, and high-frequency disease alleles.

5.13.2.1. Identical by Descent-Affected Pedigree Member (IBD-APM) Anslysis

In one embodiment, nonparametric linkage analysis involves studying affected relatives 46 (FIG. 1) in a pedigree 74 to see how often a particular copy of a chromosomal region is shared identical-by descent (IBD), that is, is inherited from a common ancestor within the pedigree. The frequency of IBD sharing at a locus can then be compared with random expectation. An identity-by-descent affected-pedigree-member (IBD-APM) statistic can be defined as:

$$T(s) = \sum_{i,j} x_{ij}(s).$$

where $x_{ij}(s)$ is the number of copies shared IBD at position s along a chromosome, and where the sum is taken over all distinct pairs (ij) of affected relatives 46 in a pedigree 74. The results from multiple families can be combined in a weighted sum T(s). Assuming random segregation, T(s) tends to a normal distribution with a mean $\mu$ and a variance a that can be calculated on the basis of the kinship coefficients of the relatives compared. See, for example, Blackwelder and Elston, 1985, Genet. Epidemiol. 2, p. 85; Whittemore and Halpern, 1994, Biometrics 50, p. 118; Weeks and Lange, 1988, Am. J. Hum. Genet. 42, p. 315; and Elston, 1998, Genetic Epidemiology 15, p. 565. Deviation from random segregation is detected when the statistic $(T-\mu)/\sigma$ exceeds a critical threshold.

5.13.2.2. Affected Sib Pair Analysis

Affected sib pair analysis is one form of IBD-APM analysis (Section 5.13.2.1). For example, two sibs can show IBD sharing for zero, one, or two copies of any locus (with a 25%-50%-25% distribution expected under random segregation). If both parents are available, the data can be partitioned into separate IBD sharing for the maternal and paternal chromosome (zero or one copy, with a 50%-50% distribution expected under random segregation). In either case, excess allele sharing can be measured with a $\chi^2$ test. In the ASP approach, a large number of small pedigrees (affected siblings and their parents) are used. DNA samples are collected from each organism and genotyped using a large collection of markers (e.g., microsatellites, SNPs). Then a check for functional polymorphism is performed. See, for example, Suarez et al., 1978, Ann. Hum. Genet. 42, p. 87; Weitkamp, 1981, N. Engl. J. Med. 305, p. 1301; Knapp et al, 1994, Hum. Hered. 44, p. 37; Holmans, 1993, Am. J. Hum. Genet. 52, p. 362; Rich et al, 1991, Diabetologica 34, p. 350; Owerbach and Gabbay, 1994, Am. J. Hum. Genet. 54, p. 909; and Berrettini et al., Proc. Natl. Acad. Sci. USA 91, p. 5918. For more information on Sib pair analysis, see Hamer et al., 1993, Science 261, p. 321.

In some embodiments, ASP statistics that test whether affected siblings pairs have a mean proportion of marker genes identical-by-descent that is >0.50 were computed. See, for example, Blackwelder and Elston, 1985, Genet. Epidemiol. 2, p. 85. In some embodiments, such statistics are computed using the SIBPAL program of the SAGE package. See, for example, Tran et al. 1991, (SIB-PAL) Sib-pair linkage program (Elston, New Orleans), Version 2.5. These statistics are computed on all possible affected pairs. In some embodiments the number of degrees of freedom of the t test is set at the number of independent affected pairs (defined per sibship as the number of affected individuals minus 1) in the sample instead of the number of all possible pairs. See, for example, Suarez and Eerdewegh, 1984, Am. J. Med. Genet. 18, p. 135.

5.13.2.3. Identical by State-Affected Pedigree Member (IBS-APM) Analysis

In some instances, it is not possible to tell whether two relatives inherited a chromosomal region IBD, but only whether they have the same alleles at genetic markers in the region, that is, are identical by state (IBS). IBD can be inferred from IBS when a dense collection of highly polymorphic markers has been examined, but the early stages of genetic analysis can involve sparser maps with less informative markers so that IBD status can not be determined exactly. Various methods are available to handle situations in which IBD cannot be inferred from IBS. One method infers IBD sharing on the basis of the marker data (expected identity by descent affected-pedigree-member; IBD-APM). See, for example, Suarez et al., 1978, Ann. Hum. Genet. 42, p. 87; and Amos et al, 1990, Am J. Hum. Genet. 47, p. 842. Another method uses a statistic that is based explicitly on IBS sharing (an IBS-APM method). See, for example, Weeks and Lange, 1988, Am J. Hum. Genet. 42, p. 315; Lange, 1986, Am. J. Hum. Genet. 39, p. 148; Jeunemaitre et al., 1992, Cell 71, p. 169; and Pericak-Vance et al., 1991, Am. J. Hum. Genet 48, p. 1034.

In one embodiment the IBS-APM techniques of Weeks and Lange, 1988, Am J. Hum. Genet. 42, p. 315; and Weeks and Lange, 1992, Am. J. Hum. Genet. 50, p. 859 are used. Such techniques use marker information of affected individuals to test whether the affected persons within a pedigree are more similar to each other at the marker locus than would be expected by chance. In some embodiments, the marker similarity is measured in terms of identity by state. In some embodiments, the APM method uses a marker allele frequency weighting function, $f(p)$, where p is the allele frequency, and the APM test statistics are presented separately for each of three different weighting functions, $f(p)=1$, $f(p)=1/\sqrt{p}$, and $f(p)=1/p$. Whereas the second and third functions render the sharing of a rare allele among affected persons a more significant event, the first weighting function uses the allele frequencies only in calculation of the expected degree of marker allele sharing. The third function, $f(p)=1/p$, can lead (more frequently than the first two) to a non-normal distribution of the test statistic. The second function is a reasonable compromise for generating a normal distribution of the test statistic while incorporating an allele frequency function. In some instances, the APM test statistics are sensitive to marker locus and allele frequency misspecification. See, for example, Babron, et al, 1993, Genet. Epidemiol. 10, p. 389. In some embodiments, allele frequencies are estimated from the pedigree data using the method of Boehnke, 1991, Am J. Hum. Genet. 48, p. 22, or by studying alleles. See, also, for example, Berrettini et al, 1994, Proc. Natl. Acad. Sci. USA 91, p. 5918.

In some embodiments, the significance of the APM test statistics is calculated from the theoretical (normal) distribution of the statistic. In addition, numerous replicates (e.g., 10,000) of these data, assuming independent inheritance of marker alleles and disease (i.e., no linkage), are simulated to assess the probability of observing the actual results (or a more extreme statistic) by chance. This probability is the empirical P value. Each replicate is generated by simulating an unlinked marker segregating through the actual pedigrees. An APM statistic is generated by analyzing the simulated dat set exactly as the actual data set is analyzed. The rank of the observed statistic in the distribution of the simulated statistics determines the empirical P value.

5.13.2.4. Quantitative Traits

Model-free linkage analysis can also be applied to quantitative traits. An approach proposed by Haseman and Elston, 1972, Behav. Genet 2, p. 3, is based on the notion that the phenotypic similarity between two relatives should be correlated with the number of alleles shared at a trait-causing locus. Formally, one performs regression analysis of the squared difference $\Delta^2$ in a trait between two relatives and the number x of alleles shared IBD at a locus. The approach can be suitably generalized to other relatives (Blackwelder and Elston, 1982, Commun. Stat. Theor. Methods 11, p. 449) and multivariate phenotypes (Amos et al., 1986, Genet. Epidemiol. 3, p. 255). See also, Marsh et al., 1994, Science 264, p. 1152, and Morrison et al., 1994, Nature 367, p. 284.

5.14. Association Analysis

This section describes a number of association tests that can be used in various steps of the methods disclosed in Section 5.1. Association studies can be done with samples of pedigrees or samples of unrelated individuals. Further, association studies can be done for a dichotomous trait (e.g., disease) or a quantitative trait. See, for example, Nepom and Ehrlich, 1991, Annu. Rev. Immunol. 9, p. 493; Strittmatter and Roses, 1996, Annu. Rev. Neurosci. 19, p. 53; Vooberg et al., 1994, Lancet 343, p. 1535; Zoller et al., Lancet 343, p. 1536; Bennet et al., 1995, Nature Genet. 9, p. 284; Grant et al., 1996, Nature Genet. 14, p. 205; and Smith et al., 1997, Science 277, p. 959. As such, association studies test whether a disease and an allele show correlated occurrence across the population, whereas linkage studies (Section 5.13, above) determine whether there is correlated transmission within pedigrees.

Whereas linkage analysis involves the pattern of transmission of gametes from one generation to the next, association is a property of the population of gametes. Association exists between alleles at two loci if the frequency, with which they occur within the same gamete, is different from the product of the allele frequencies. If this association occurs between two linked loci, then utilizing the association will allow for fine localization, since the strength of association is in large part due to historical recombinations rather than recombination within a few generations of a family. In the simplest scenario, association arises when a mutation, which causes disease, occurs at a locus at some time, $t_o$. At that time, the disease mutation occurs on a specific genetic background composed of the alleles at all other loci; thus, the disease mutation is completely associated with the alleles of this background. As time progresses, recombination occurs between the disease locus and all other loci, causing the association to diminish. Loci that are closer to the disease locus will generally have higher levels of association, with association rapidly dropping off for markers further away. The reliance of association on evolutionary history can provide localization to a region as small as 50-75 kb. Association is also called linkage disequilibrium. Association (linkage disequilibrium) can exist between alleles at two loci without the loci being linked.

Two forms of association analysis are discussed in the sections below, population based association analysis and family based association analysis. More generally, those of skill in the art with appreciate that there are several different forms of association analysis, and all such forms of association analysis can be used at appropriate steps in the methods disclosed in Section 5.1, above.

In some embodiments, whole genome association studies are performed in accordance with the present invention. Two methods can be used to perform whole-genome association studies, the "direct-study" approach and the "indirect-study" approach. In the direct-study approach, all common functional variants of a given gene are cataloged and tested directly to determine whether there is an increased prevalence (association) of a particular functional variant in affected individuals within the coding region of the given gene. The "indirect-study" approach uses a very dense marker map (derived from marker genotype data 80 of FIG. 1, for example) that is arrayed across both coding and noncoding regions. A dense panel of polymorphisms (e.g., SNPs) from such a map can be tested in controls to identify associations that narrowly locate the neighborhood of a susceptibility or resistance gene. This strategy is based on the hypothesis that each sequence variant that causes disease must have arisen in a particular individual at some time in the past, so the specific alleles for polymorphisms (haplotype) in the neighborhood of the altered gene in that individual (organism 46, FIG. 1) can be inherited in all of his or her descendants. The presence of a recognizable ancestral haplotype therefore becomes an indicator of the disease-associated polymorphism. In actuality, some of the alleles will be in association while others will not due to recombination occurring between the mutation and other polymorphisms.

5.14.1. Population-Based (Model-Free) Association Analysis

In population-based (model-free) association studies, allele frequencies in afflicted organisms are contrasted with allele frequencies in control organisms in order to determine if there is an association between a particular allele and a trait. Population-based association studies for dichotomous traits are also referred to as case-control studies. A case-control study is based on the comparison of unrelated affected and unaffected individuals from a population. An allele A at a gene of interest is said to be associated with the phenotype if it occurs at significantly higher frequency among affected compared with control individuals. Statistical significance can be tested in a number a methods, including, but not limited to, logistic regression. Association studies are discussed in Lander, 1996, Science 274, 536; Lander and Schork, 1994, Science 265, 2037; Risch and Merikangas, 1996, Science 273, 1516; and Collins et al., 1997, Science 278, 1533.

As is true for case-control studies generally, confounding is a problem for inferring a causal relationship between a disease and a measured risk factor using population-based association analysis. One approach to deal with confounding is the matched case-control design, where individual controls are matched to cases on potential confounding factors (for example, age and sex) and the matched pairs are then examined individually for the risk factor to see if it occurs more frequently in the case than in its matched control. In some embodiments, cases and controls are ethnically comparable. In other words, homogeneous and randomly mating populations are used in the association analysis. In some embodiments, the family-based association studies described below are used to minimize the effects of confounding due to genetically heterogeneous populations. See, for example, Risch, 2000, Nature 405, p. 847.

5.14.2. Family-Based Association Analysis

Family-based association analysis is used in some embodiments of the invention. In some embodiments, each affected organism is matched with one or more unaffected siblings (see, for example, Curtis, 1997, Ann. Hum. Genet. 61, p. 319) or cousins (see, for example, Witte, et al., 1999, Am J. Epidemiol. 149, p. 693) and analytical techniques for matched case-control studies is used to estimate effects and to test a hypotheses. See, for example, Breslow and Day, 1989, Statistical methods in cancer research I, The analysis of case-control studies 32, Lyon: IARC Scientific Publications. The following subsections describe some forms of family-based association studies. Those of skill in the art will recognize that there are numerous forms of family-based association studies and all such methodologies can be used in appropriate steps in the methods disclosed in Section 5.1.

5.14.2.1. Haplotype Relative Risk Test

In some embodiments, the haplotype relative risk test is used. In the haplotype relative risk method, all marker alleles compared arise from the same person. The marker alleles that parents transmit to an affected offspring (case alleles) are compared with those that they do not transmit to such an offspring (control alleles). One can also compare transmitted and nontransmitted genotypes. Consider the 2n parents of n affected persons. This population can be classified into a fourfold table according to whether the transmitted allele is a marker allele (M) or some other allele $\overline{M}$ and according to whether the nontransmitted allele is similarly M or $\overline{M}$:

| Transmitted allele | Nontransmitted allele | | Total |
|---|---|---|---|
| | M | $\overline{M}$ | |
| M | a | b | a + b |
| $\overline{M}$ | c | d | c + d |
| | a + c | b + d | 2n = a + b + c + d |

To test for association, a determination is made as to whether the proportion of M alleles that are transmitted, a/(a+b), differs significantly from the proportion of M alleles that are nontransmitted, a/(a+c). One appropriate statistical test for this determination is comparison of $(b-c)^2/(b+c)$ to a chi-square distribution with one degree of freedom when the sample is large.

The row totals for the table above are the numbers of transmitted alleles that are M and $\overline{M}$, while the column totals are the numbers of nontransmitted alleles that are M and $\overline{M}$. These four totals can be put into a fourfold table that classifies the 4n parental alleles, rather than the 2n parents:

| Marker allele | Transmitted | Non-transmitted | Total |
|---|---|---|---|
| M | a + b | a + c | 2a + b + c |
| $\overline{M}$ | c + d | b + d | b + c + 2d |
| Total | 2n | 2n | 4n |

The haplotype relative risk ratio is defined as $(a+b)(c+d)/(a+c)(c+d)$. A chi-square distribution using one degree of freedom can be used t determine whether the haplotype relative risk ratio differs significantly from 1. The haplotype relative risk test does not assume that the transmitted and nontransmitted alleles are independent, utilized information only from the heterozygous $M\overline{M}$ parents, and does not have a control group. See, for example, Rudorfer, et al., 1984, Br. J. Clin. Pharmacol. 17, 433; Mueller and Young, 1997, *Emery's Elements of Medical Genetics*, Kalow ed., p. 169-175, Churchill Livingstone, Edinburgh; and Roses, 2000, Nature 405, p. 857, Elson, 1998, Genetic Epidemilogy, 15, p. 565.

5.14.2.2. Transamission Equilibrium Test

In some embodiments, the transmission equilibrium test (TDT) is used. TDT considers parents who are heterozygous for an allele and evaluates the frequency with which that allele is transmitted to affected offspring. By restriction to heterozygous parents, the TDT differs from other model-free tests for association between specific alleles of a polymorphic marker and a disease locus. The parameters of that locus, genotypes of sampled individuals, linkage phase, and recombination frequency are not specified, and the test is not limited to families informative for recombination. Nevertheless, by considering only heterozygous parents, the TDT is specific for association between linked loci.

TDT is a test of linkage and association that is valid in heterogeneous populations. It was originally proposed for data consisting of families ascertained due to the presence of a diseased child. The genetic data consists of the marker genotypes for the parents and child. The TDT is based on transmissions, to the diseased child, from heterozygous parents, or parents whose genotypes consist of different alleles. In particular, consider a biallelic marker with alleles $M_1$ and $M_2$. The TDT counts the number of times, $n_{12}$, that $M_1M_2$ parents transmit marker allele $M_1$ to the diseased child and the number of times, $n_{21}$, that $M_2$ is transmitted. If the marker is not linked to the disease locus, i.e. $\theta=0.5$, or if there is no association between $M_1$ and the disease mutation, then conditional on the number of heterozygous parents, and in the absence of segregation distortion, $n_{12}$ is distributed binomially: $B(n_{12}+n_{21}, 0.5)$. The null hypothesis of no linkage or no association can be tested with the statistic $$T_{TDT} = \frac{(n_{12} - n_{21})^2}{n_{12} + n_{21}}$$

with statistical significance level approximated using the $\chi 2$ distribution with one df or computed exactly with the binomial distribution. When transmissions from more than one diseased child per family are included in the TDT statistic, the test is valid only as a test of linkage.

Several extensions of the TDT test have been proposed and all such extensions are within the scope of the present invention. See, for example, Mortin and Collins, 1998, Proc. Natl. Acad. Sci. USA 95, p. 11389; Terwilliger, 1995, Am J Hum Genet 56, p. 777. See also, for example, Mueller and Young, 1997, *Emery's Elements of Medical Genetics*, Kalow ed., p. 169-175, Churchill Livingstone, Edinburgh; Zhao et al., 1998, Am. J. Hum. Genet. 63, p. 225; Roses, 2000, Nature 405, p. 857; Spielman et al., 1993, Am J. Hum. Genet. 52, p. 506; and Ewens and Spielman; Am. H. Hum. Genet. 57, p. 455.

5.14.2.3. Sibship-Based Test

In some embodiments, the sibship-based test is used. See, for example, Wiley, 1998, Cur. Pharmaceut. Des. 4, p. 417; Blackstock and Weir, 1999, Trends Biotechnol. 17, p. 121; Kozian and Kirschbaum, 1999, Trends Biotechnol. 17, p. 73; Rockett et al., Xenobiotica 29, p. 655; Roses, 1994, J. Neuropathol. Exp. Neurol 53, p. 429; and Roses, 2000, Nature 405, p. 857.

5.15. Methods for Identifying Cellular Constituents that Associate with a Trait In step 208 of Section 5.1, above, patterns of cellular constituent levels (e.g., gene expression levels, protein abundance levels, etc.) are identified that associate with the trait under study. This section describes a number of different methods by which step 208 of Section 5.1 can be carried out. Those of skill in the art will appreciate that there are a number of additional ways that step 208 can be carried out, and all such ways are included within the scope of the present invention.

5.15.1. Correlation Analysis

Correlation analysis can be used between the trait of interest and cellular constituent levels. An example of this approach is illustrated in Golub et al., 1999, *Science* 286: 531. Golub et al. developed a class predictor for patients that have acute lymphoblastic leukemia (ALL) versus patients that have acute myeloid leukemia (AML). Expression data for 6817 genes from 37 patients (27 ALL, 11 AML) was obtained. Next, the expression patterns for the 6817 genes in the 37 patients were examined using neighborhood analysis.

In neighborhood analysis, each cellular constituent is represented by an expression vector $v(g)=(e_1, e_2, \ldots, e_n)$ where $e_i$ denotes the expression level (or abundance) of cellular constituent g in the $i^{th}$ organism in a plurality of organisms. A class vector is represented by the idealized expression pattern (abundance) $c=(c_1, c_2, \ldots, c_n)$, where $c_i=+1$ or 0 according to whether the $i^{th}$ sample was taken from a patient that belongs to class 1 (e.g., ALL) or class 2 (e.g., AML). Correlation between c and v(g) is measured between a cellular constituent and a class distinction in a variety of ways. For example, the Pearson correlation coefficient or the Euclidean distance can be used. In Golub et al. a measure of correlation, P(g,c), that emphasizes the "signal-to-noise" ratio in using the cellular constituent as a predictor was used. The expressions $[\mu_1(g), \sigma_1(g)]$ and $[\mu_2(g), \sigma_2(g)]$ denote the means and standard deviations of the log of the expression levels (or abundances)

of cellular constituent g for the samples in class 1 (e.g., ALL) and class 2 (e.g., AML), respectively, and $P(g,c)=[\mu_1(g)-\mu_2(g)]/[\sigma_1(g)+\sigma_2(g)]$ reflects the difference between the classes relative to the standard deviation within the classes. Large values of $|P(g,c)|$ indicate a strong correlation between the cellular constituent level (e.g., gene expression) and the class distinction, while the sign of P(g,c) being positive or negative corresponds to g being more abundant in class 1 or class 2. Unlike a standard Pearson correlation coefficient, P(g,c) is not confined to the range [−1, +1]. Neighborhoods $N_1(c,r)$ and $N_2(c,r)$ of radius r around class 1 and class 2 are defined to be the sets of cellular constituents such that P(g,c)=r and P(g,c)=−r, respectively. An unusually large number of cellular constituents within the neighborhoods indicates that many cellular constituents have abundances (e.g., expression patterns) closely correlated with the class vector.

From the neighborhood analysis, a set of informative cellular constituents (a set of cellular constituents that discriminate between class 1 and class 2; a set of cellular constituents that discriminate the trait) can be chosen. In Golub et al., for example, the set of informative cellular constituents consists of the n/2 genes closest to a class vector high in class 1 [that is, P(g,c) as large as possible] and the n/2 genes closest to class 2 [that is, −P(g,c) as large as possible].

5.15.2. T-Test

Another method that can be used to identify cellular constituent levels (e.g. gene expression levels, protein abundance levels, etc.) that associate with the trait under study is the t-test. The t-test assesses whether the means of two groups are statistically different from each other. When the t-test is used, processing step 208 of Section 5.1, above, seeks to identify those cellular constituents that have significantly different mean abundances in the classes of organism 46. For example, in the case where the plurality of organisms 46 is divided into two groups, those that have been treated with a drug and those that have not, the t-test is used to find those cellular constituents that have a significantly different mean expression level in the organisms that were treated with a drug versus those organisms that were not treated with a drug. See, for example, Smith, 1991, Statistical Reasoning, Allyn and Bacon, Needham Heights, Mass., pp. 361-365. The t-test is represented by the following formula:

$$t = \frac{\overline{X}_T - \overline{X}_C}{\sqrt{\frac{\mathrm{var}_T}{n_T} + \frac{\mathrm{var}_C}{n_C}}}$$

where, the numerator is the numerator is the difference between the mean level of a given cellular constituent in a first group (T) and a second group (C); and $\mathrm{var}_T$ is the variance (square of the deviation) in the level of the given cellular constituent in group T;

$\mathrm{var}_C$ is the variance (square of the deviation) in the level of the given cellular constituent in group C;

$n_T$ is the number of organisms 46 in group T; and $n_C$ is the number of organisms 46 in group C.

The t-value will be positive if the first mean is larger than the second and negative if it is smaller. The significance of any t-value is determined by looking up the value in a table of significance to test whether the ratio is large enough to say that the difference between the groups is not likely to have been a chance finding. To test the significance, a risk level (called the alpha level) is set. In some embodiments of the present invention the alpha level is set at 0.05. This means that the five times out of a hundred there would be a statistically significant difference between the means even if there was none (i.e., by "chance"). In some embodiments, the alpha level is set at 0.025, 0.01 or 0.005. Further, to test significance, the number of degrees of freedom (df) for the test needs to be determined. In the t-test, the degrees of freedom is the sum of the persons in both groups (T and C) minus 2. Given the alpha level, the df, and the t-value, it is possible to look the t-value up in a standard table of significance (see, for example, Table m of Fisher and Yates, *Statistical Tables for Biological, Agricultural, and Medical Research*, Longman Group Ltd., London) to determine whether the t-value is large enough to be significant. In some embodiments, a cellular constituent is considered to discriminate between two groups of organisms 46 (e.g. a first group that is treated with a compound and a second group that is not treated with a compound) when t is 3 or greater, 4 or greater, 5 or greater, 6 or greater, or 7 or greater.

5.15.3. Paired T-Test

Another method that can be used to identify cellular constituent levels (e.g., gene expression levels, protein abundance levels, etc.) that associate with the trait under study is the paired t-test. The paired t-test assesses whether the means of two groups are statistically different from each other. The paired t-test is generally used when measurements are taken from the same organism 46 before and after some perturbation, such as injection of a drug. For example, the paired t-test can be used in embodiments of processing step 208 of Section 5.1 to determine the significance of a difference in blood pressure before and after administration of a compound that affects blood pressure. The paired t-test is represented by the following formula:

$$t = \frac{\overline{d}}{S_d / \sqrt{n}}$$

where, the numerator is the paired sample mean;

Sd is the paired sample deviation; and n is the number of pairs considered.

5.15.4. Other Parametric Statistical Tests

When statistics are calculated under the assumption that the data follow some common distribution, such as the normal distribution, they are termed parametric statistics. It follows that statistical tests based on these parametric statistics are called parametric statistical tests. Thus, when the data has a normal distribution, any number of well-known parametric statistical tests can be used in processing step 208 of Section 5.1. Such tests include, but are not limited to the t-tests described above, analysis of variance (ANOVA), repeated measures ANOVA, Pearson correlation, simple linear regression, nonlinear regression, multiple linear regression or multiple nonlinear regression. For example, regression can be used to see how two variables (two different cellular constituents) vary together.

5.15.5. Nonparametric Statiatical Tests

Tests that do not make assumptions about the population distribution are referred to as non-paramatric tests. In some embodiments of processing step 208 of Section 5.1, nonparametric tests are used. In some embodiments, a Wilcoxon signed-rank test, a Mann-Whitney test, a Kruskal-Wallis test, a Friedman test, a Spearman rank order correlation coefficient, a Kendall Tau analysis, or a nonparametric regression test is used.

5.16. Exemplary Sources of Pedigree Data

Mice. The methods of the present invention are applicable to any living organism in which genetic variation can be tracked. Therefore, by way of example, pedigree data 74 (FIG. 1) is obtained from experimental crosses or a human population in which genotyping information and relevant clinical trait information is provided. One such experimental design for a mouse model for complex human diseases is given in FIG. 6. In FIG. 6, there are two parental inbred lines that are crossed to obtain an $F_1$ generation. The $F_1$ generation is intercrossed to obtain an $F_2$ generation. At this point, the $F_2$ population is genotyped and physiologic phenotypes for each $F_2$ in the population are determined to yield genotype and pedigree data 74. These same determinations are made for the parents as well as a sampling of the $F_1$ population.

Zea mays. Data based on an experimental cross done in Zea mays are given in FIG. 7. This particular cross differs from the mouse system discussed in conjunction with FIG. 6 in that the $F_2$ generation was selfed to obtain an $F_3$ generation. Then pools of $F_3$ plants were derived from the same $F_2$ parent to obtain phenotype information (physiologic phenotypes as well as the gene expression phenotypes) while the genotype information came from the $F_2$ generation.

To perform QTL analysis using the cross identified in FIG. 7, the following assumptions are made. The trait for an $F_y$ plant is assumed to depend on the QTL genotype of the $F_y$: $y_{QQ} \sim f(\mu_1, \sigma_1^2)$, $y_{Qq} \sim f(\mu_2, \sigma_2^2)$, $y_{qq} \sim f(\mu_3, \sigma_3^2)$. For a putative QTL location, the probability of QQ, Pr(QQ), the probability of Qq, Pr(Qq), and the probability of qq, Pr(qq) are estimated using the genotypes at flanking markers, the marker map and the breeding design.

Due to the nature of biological variation, it is expected that genes, underlying genetic control for the abundance of mRNA transcripts, will interact in a synergistic fashion. There are numerous methods for the detection of such gene-gene interaction. One such method utilizes linkage information for each of two genes and assesses how this information correlates among individuals (see Cox et al., 1999, Loci on chromosomes 2 (NIDDM1) and 15 interact to increase susceptibility to diabetes in Mexican Americans, Nat Genet. 21 (2):213-215). For the $i^{th}$ of N $F_{2:3}$ observations, let $Y_{1i}$ be the likelihood for the presence of a QTL at location 1 given the marker data for the $i^{th}$ $F_2$ individual and the phenotype for their $F_3$ pool. Likewise, let $Y_{2i}$ be the corresponding information for the presence of a QTL at location 2. The correlation between the variables $Y_{1i}$ and $Y_{2i}$ is estimated as:

$$r_{12} = \frac{\sum_{i=1}^{N}(Y_{1i} - \overline{Y}_1)(Y_{2i} - \overline{Y}_2)}{\sqrt{(Y_{1i} - \overline{Y}_1)^2(Y_{2i} - \overline{Y}_2)^2}}$$

where $$\overline{Y}_1 = \frac{1}{N}\sum_{i=1}^{N} Y_{1i} \text{ and } \overline{Y}_2 = \frac{1}{N}\sum_{i=1}^{N} Y_{2i}$$

Statistical significance can be assessed using the t-distribution with N-2 degrees of freedom. The nominal P-value for the test was determined by the probability that a random variable from this distribution exceeds the absolute value of the following test statistic:

$$t = \frac{r_{12}}{\sqrt{(1 - r_{12}^2/(N-2))}}$$

Due to the large-scale testing necessary to assess all possible gene-gene interactions, multiple testing corrections are preferably applied. One such multiple testing correction method is the Bonferroni adjustment that adjusts nominal p-values by multiplying by the total number of tests performed.

Significant correlations between linkage information for two unlinked loci provide insight into their mechanism for interaction. In particular, loci with positive correlation indicate two genes are influencing transcript abundance of the specific mRNA in the same biological pathway or in interacting biological pathways. On the other hand, loci with negative correlation provide evidence of disease heterogeneity so that one gene influences variation in mRNA abundance in one set of observations while a separate gene influences variation in mRNA abundance in other observations. The strength of the evidence for gene-gene interaction is further assessed by studying the genotype distribution for the two loci tested. Due to the large number of positions tested, it is possible that the interaction could be due to correlated genotypes between the two loci. This can happen by chance despite the loci being unlinked. The genotype distributions for non-independence can be tested using Fisher's exact test. Gene-gene interactions that does not demonstrate non-independence can be considered stronger evidence for biological interaction.

Human populations. The present invention is not constrained to model systems, but can be applied directly to human populations. For example, pedigree and other genotype information for the Ceph family is publicly available (Center for Medical Genetics, Marshfield, Wis.), and lymphoblastoid cell lines from individuals in these families can be purchased from the Coriell Institute for Medical Research (Camden, N.J.) and used in the expression profiling experiments of the instant invention. The plant, mouse, and human populations discussed in this Section represent non-limiting examples of pedigree data 74 for use in the present invention.

5.17. $F_2$ Intercross

An $F_2$ intercross was constructed from C57BL/6J and DBA/2J strains of mice. Mice were on a rodent chow diet up to 12 months of age, and then switched to an atherogenic high-fat, high-cholesterol diet for another four months. See, for example, Drake et al., 2001, Physiol Genomics 5, 205-15, which is hereby incorporated by reference in its entirety. Parental and $F_2$ mice were sacrificed at sixteen months of age. At death the livers were immediately removed, flash-frozen in liquid nitrogen and stored at −80° C. Total cellular RNA was purified from 25 mg portions using an Rneasy Mini kit according to the manufacturer's instructions (Qiagen, Valencia, Calif.). Competitive hybridizations were performed by mixing fluorescently labeled cRNA (5 mg) from each of 111 $F_2$ liver samples, 5 DBA/2J liver samples, and 5 C57BL/6J liver samples, with the same amount of cRNA from a reference pool comprised of equal amounts of cRNA from each of the 111 liver samples profiled.

Liver tissues from the 111 $F_2$ mice constructed from two standard inbred strains of mice, C57BL/6J and DBA/2J, were profiled using a 25K mouse gene oligonucleotide microarray. The hybridizations were performed in duplicate using fluor reversal. The mouse microarray contained 23,574 non-control oligonucleotide probes for mouse genes and 2,186 control oligos. Full-length mouse sequences were extracted from Unigene clusters, build # 91 (Schuler et al., 1996, Science 274, 540-546), and combined with RefSeq mouse sequences from June 2001 (Pruitt and Maglott, 2001, Nucleic Acids Research 29, 137-140), and RIKEN full-length sequences, version fantom 1.01 (Kawai et al., 2001, Nature 409, 685-690, 2001). This collection of full-length sequences was clustered and one representative sequence per cluster was selected, resulting in 18,597 full-length mouse sequences. To complete the array, 3' ESTs were selected from Unigene clusters that did not cluster with any full-length sequence from Unigene, RefSeq, or RIKEN. To further down select ESTs, 3' ESTs that had significant homology to human genes were chosen, resulting in 4,977 3' mouse ESTs with human homology. To select a probe for each gene sequence, a series of filtering steps was used, taking into account repeat sequences, binding energies, base composition, distance from the 3' end, sequence complexity, and potential cross-hybridization interactions (Hughes et. al., 2001, Nat Biotechnol. 19, 342-347). For each gene, every potential 60-nucleotide sequence was examined and the 60-mer best satisfying the criteria was selected and printed on the microarray.

Array images were processed to obtain background noise, single channel intensity, and associated measurement error estimates using the techniques referenced in Hughes, 2000, Cell 102, 109-26. Expression changes between two samples were quantified as $\log_{10}$ (expression ratio) where the 'expression ratio' was taken to be the ratio between normalized, background-corrected intensity values for the two channels (red and green) for each spot on the array. An error model for the log ratio was applied to quantify the significance of expression changes between two samples. This error model is described in Roberts et al., 2000, Science 287, 873-880. This error model for the log ratio was applied to quantify the significance of expression changes between the two samples.

The expression values from these experiments were treated as quantitative traits and carried through a linkage analysis using evenly spaced markers across the autosomal chromosomes, to identify eQTL controlling for transcript abundances in this segregating population (FIG. 2A, step 218). For this QTL analysis, a complete linkage map (marker genotype data 78) for all chromosomes except the Y chromosome in mouse was constructed at an average density of 13 cM using microsatellite markers in the manner described by Drake et al. (J. Orthop. Res. 19, 511-517, 2001). Linkage maps were constructed and QTL analysis was performed using MapMaker QTL (Lincoln, S. E., Daly, M. J. & Lander, E. S., Whitehead Institute for Biomedical Research, Cambridge, Mass.) and QTL Cartographer (Basten, C. A., Weir, B. S. & Zeng, Z. B., Department of Statistics, North Carolina State University, Raleigh, N.C., 1999). Log of the odds ratio (LOD) scores were calculated at 2-cM intervals throughout the genome for each of the 23,574 genes represented on the mouse microarray. In addition to standard interval mapping techniques employed to detect loci affecting the gene expression traits of interest, additional analyses were performed to determine whether controlling for genetic background variation using markers outside a putative region of linkage and whether multiple traits considered simultaneously could increase evidence for linkage. Composite interval mapping ("CIM") techniques were employed so that markers unlinked with the test position were considered as cofactors in the statistical model for marker-trait association. Given multiple quantitative traits, CIM analysis can be extended to consider multiple traits simultaneously, potentially dramatically increasing the power to detect loci affecting the traits of interest. Joint CIM analysis was first described by Jian and Zeng (Genetics 140, 1111-27, 1995) and is currently implemented in the QTL Cartographer software.

5.18. EXAMPLES

The following sections describe specific examples of the methods of the present invention.

5.18.1. Melanocortin $MC_4$ Receptor

The melanocortin $MC_4$ receptor is widely distributed in virtually all the major brain regions including the cerebral cortex, hypothalamus, thalamus, brainstem, and spinal cord. See, Mountjoy et al., 1994, Mol. Endocrinol. 8, p. 1298; Mounjoy and Wild, 1998, Brain Res. Dev. Brain Res. 107, p. 309; Van der Kraan et al., 1999, Brain Res. Mol. Brain Res. 63, p. 276; and Cowley et al., 1999, Neuron 24, p. 155. Diverse lines of evidence implicate the melanocortin $MC_4$ receptor in regulating food intake and energy metabolism. The highest level of melanocortin $MC_4$ receptor expression is observed in the hypothalamus, especially in the paraventricular nucleus and in the dorsal motor nucleus of the vagus in the caudal brainstem (Mounjoy et al., 1994, Mol. Endocrinol. 8, p. 1298). Such a distribution pattern correlates with the brain sites displaying high sensitivity to melanocortin-regulated feeding behavior (Kim et al., 2000, Diabetes 49, p. 177; Williams et al., 2000, Endocrinology 141, p. 1332). Evidence indicating that the $MC_4$ receptor plays a role in regulating body weight includes that observation that (i) Mc4R−/− mice are obese, (ii) melanocortin $MC_4$ receptor agonist inhibit food intake, and (iii) obese humans have been identified with mutations in the melanocortin $MC_4$ receptor gene.

The characterization of a variety of rodent obesity models with altered melanocartin signaling suggests that melanocortins can play a significant role in regulating body weight in humans. This suggests that agonists of melanocortin action would provide an effective anti-obesity therapy. However, the development of an $MC_4$ receptor agonist is hampered by the fact that $MC_4$ receptor activity is localized in brain tissue. Thus, direct assessment of $MC_4$ receptor activity requires direct assessment of $MC_4$ receptor activity in the brain. This example provides details on how the methods of the present invention were used to identify a panel of genes whose expression in blood cells serves as a surrogate for the direct assessment of $MC_4$ receptor activity in brain tissue.

Steps 202-206. Sprague Dawley rats were either dosed with an $MC_4$ receptor agonist or a drug-free vehicle. The dosing was based on known efficacy of the $MC_4$ receptor agonist that had been previously determined using wild-type versus $MC_4$ receptor knock out mice. The rats were either fed regular chow "lean" or an atherogenic high-fat, high-cholesterol diet to induce obesity (diet induced obesity, "DIO"). Thus, there were four classes of mice:

lean diet/drug-free vehicle
lean diet/$MC_4$ receptor agonist
DIO-type diet/drug-free vehicle
DIO-type diet/$MC_4$ receptor agonist For each experiment six rats each were dosed with either an MC4R agonist or vehicle by oral galvage. The selective MC4R agonist used were L-386003 or L-000178243. Both compounds were given at 30 mpk that was determined as being biologically active in wild type but not MC4R/MC3R knockout mice. The length of exposure was six hours. Thus, in this example, the perturbation selected in step 202 of FIG. 2A is exposure of rats to a $MC_4$ receptor agonist.

Step 204. Whole blood was collected from the Sprague Dawley rats after they had been treated with $MC_4$ receptor agonist for six hours. Specifically, 8.0 ml of blood was collected from each rat by decapitation for fast blood flow to avoid clotting. The RNA was isolated using the protocol provided on pages 64-68 of the Rneasy Midi/Maxi Handbook, June 2001, Qiagen, Valencia, Calif. Briefly, the blood was mixed with five volumes of erythrocyte lysis buffer (Qiagen, catalog number 79217) and then incubated for ten to fifteen minutes on ice. Each mixture was vortexed briefly twice during this incubation. Then, each mixture was centrifuged at 400×g for ten minutes at 4° C. The supernatent was completely removed and discarded and each leukocyte pellet was saved. Sixteen ml of erythrocyte lysis buffer (Qiagen, Valencia, Calif., catalog number 79217) was added to each cell pellet and cells were resuspended by brief vortexing. Each mixture was centrifuged at 400×g for ten minutes at 4° C. and the supernatent was removed and discarded. Each cell pellet was warmed to 20-25° C. and resuspended in 2-4 ml of buffer RLT (Qiagen). The cells were homogenized using a conventional rotor-stator homogenizer for at least 45 seconds at maximum speed until the samples were uniformly homogenous. Alternatively, the samples were vortexed for 10 seconds, and the lysate was passed five to ten times through an 18-20 gauge needle fitted to an Rnase-free syringe. Then, 1 volume (2.0 ml to 4.0 ml) of seventy percent ethanol was added to each homogenized lysate, and mixed thoroughly.

Each sample, including any precipitate, was applied to an Rneasy midi column packed in a 15 ml centrifuge tube (Qiagen, Valencia, Calif.). Each tube was closed and centrifuged for five minutes at 3000-5000×g. The flow-through was discarded.

Buffer RW1 (Qiagen, Valencia, Calif.) was pipetted into each RNeasy column and each column was centrifuged for five minutes at 3000-5000×g to wash. Then DNase I stock solution (Rneasy Midi/Maxi Handbook, June 2001, p. 91, Qiagen, Valencia, Calif.) was added to buffer RDD (Qiagen) to form a DNase I incubation mix. The DNase I incubation mix was added directly onto each RNeasy silica-gel membrane, and incubated at 20-30° C. for fifteen minutes. Then, buffer RW1 (Qiagen) was pipetted into each RNeasy column and incubated at 20-30° C. for fifteen minutes. Each mixture was then centrifuged for five minutes at 3000-5000×g and the flow-through was discarded. See the Rneasy Midi/Maxi Handbook, June 2001, p. 91-92, Qiagen, Valencia, Calif.

Four ml of buffer RW1 (Qiagen) was added to each RNeasy column. Each centrifuge tube was closed and centrifuged for five minutes at 3000-5000×g to wash each column. Flow-through was discarded. Then 2.5 ml of buffer RPE (Qiagen) was added to each RNeasy column. Each centrifuge tube was closed and centrifuged for two minutes at 3000-5000×g to wash each column. Flow-through was discarded. Then, another 2.5 ml of buffer RPE (Qiagen) was added to each RNeasy column. Each centrifuge tube was closed and centrifuged for two minutes at 3000-5000×g to wash each column. Flow-through was discarded.

To elute, each RNeasy column was transferred to a new 15 ml collection tube (Qiagen). RNase-free water was pipetted directly onto each RNeasy silica-gel membrane within each tube and each tube was allowed to stand for one minute. Each tube was then centrifuged for three minutes at 3000-5000 g. Typical yields were 25-40 µg of whole RNA was isolated per 8 ml of blood collected from each rat.

Five micrograms of total RNA from each sample was amplified into cRNA by an in vitro transcription procedure with oligo-dT primer. For details on methods by which MRNA can be used to derive cRNA see, for example, Griffiths et al., 1999, *An Introduction to Genetic Analysis*, W.H. Freeman and Company, New York, 7th Edition, Chapter 40. cRNA was labeled with Cy3 or Cy5 dyes using a two-step process with allylamine-derivatized nucleotides and N-hydroxy succinimide esters of Cy3 or Cy5 (CyDye, Amersham Pharmacia Biotech). The labeled cRNAs were fragmented to an average size of approximately 50 to 100 nucleotides before hybridization. Competitive hybridizations were performed by mixing fluorescently labeled cRNA from each of the blood samples with the same amount of cRNA from a reference pool. Array images were processed as described in Hughes, et al., 2000, Cell 102, p. 109, to obtain background noise, single channel intensity, and associated measurement error estimates. Expression changes between two samples (single versus pool) were quantified as $\log_{10}$ (expression ratio) where the 'expression ratio' was taken to be the ratio between normalized, background-corrected intensity values for the two channels (red and green) for each spot on the array. An error model for the log ratio was applied as described by Roberts et al., 2000, Science 287, p. 873, to quantify the significance of expression changes between two samples.

Step 208. Table 2 describes the various microarray experiments that were conducted in order to determine which rat genes are differentially expressed in the presence of the $MC_4$ receptor agonist.

TABLE 2

Microarray experiment definitions

| Single | Pool | Element in FIG. 8 | Appearance of genetic signature |
|---|---|---|---|
| DIO/L-386003 | DIO/vehicle | 802 | Yes |
| DIO/vehicle | DIO/vehicle | 804 | No |
| DIO/vehicle | DIO/vehicle | 806 | No |
| Lean/L-386003 | Lean/vehicle | 808 | Yes |
| Lean/vehicle | Lean/vehicle | 810 | No |
| DIO/vehicle | DIO/vehicle | 812 | No |
| DIO/L-386003 | DIO/vehicle | 814 | Yes |
| DIO/vehicle | DIO/vehicle | 816 | No |
| DIO/L-178243 | DIO/vehicle | 818 | Yes |
| Lean/untreated | Lean/untreated | 820 | No |

As summarized in Table 8, several different types of experiments were performed. For example, consider the case in which the singles were DIO/drug and the pool was DIO/vehicle. In each of those microarray experiments, cRNA from a single diet induced obesity rat that had been exposed to the $MC_4$ receptor agonist was labeled with either Cy3 or Cy5 dye. Then, cRNA from a plurality of diet induced obesity rats that had been exposed to vehicle (i.e., were not exposed to the $MC_4$ receptor agonist) was labeled with the alternate die. Both the single and pooled cRNA were competitively hybridized to the microarray and the relative expression of 23,574 genes on the microarray was measured.

A total of 23,574 genes were measured. Differential expression was observed in every case in which a rat that had been exposed to the $MC_4$ receptor agonist was used as a single, regardless of which diet the rat was on (Table 2, FIG. 8). The 601 genes that were measured in the experiments summarized in Table 2 were subjected to one dimensional agglomerative hierarchical clustering. In microarray experiments in which a rat that had been exposed to the $MC_4$ receptor agonist was used as a single, the clustering resulted in gene clusters that included genes that were up-regulated in response to the $MC_4$ receptor agonist and gene clusters that were down-regulated in response to the $MC_4$ receptor agonist. In microarray experiments in which a rat that had been exposed to vehicle was used as a single, the one-dimensional agglomerative clustering failed to achieve clusters that include genes that were significantly up-regulated or down-regulated in response to the vehicle. Advantageously, any of the gene clusters that include significantly up-regulated or down-regulated genes that are identified in FIG. 8 can be used as a surrogate for accessing the activity of the $MC_4$ receptor in the brain. The techniques used in this example, can be used to identify gene expression changes that are common amongst the chemical classes of compound. Further the gene expression changes illustrated in FIG. 8 are characteristic of altered biological activity of the target protein. Although the surrogate tissue in this example is blood cells, in other embodiments of this example, the surrogate tissue can be white adipose tissue.

5.18.2. Insulin

This example combines genetic information with expression information to establish a signature for variation of insulin levels with expression patterns in liver tissue. This example shows that, although insulin is expressed in the pancreas, the hormone induces a significant genetic signature in the liver. This genetic signature can be used to monitor liver expression.

Steps 202-206. In this example, the perturbation that is selected for study is insulin expression in the liver. Thus, in this example, the perturbation is in fact a complex trait.

An $F_2$ intercross was constructed from C57BL/6J and DBA/2J strains of mice. More details on this cross are described in Drake et al., 2001, Physiol Genomics 5, p. 205. Insulin levels in the blood were measured in the $F_2$ mice. Parental and F2 mice were sacrificed. At death the livers were immediately removed, flash-frozen in liquid nitrogen and stored at −80° C. Total cellular RNA was purified from 25 mg portions of the liver from each F2 mice using an Rneasy Mini kit according to the manufacturer's instructions (Qiagen, Valencia, Calif.).

Competitive hybridizations were performed by mixing fluorescently labeled cRNA (5 mg) from each $F_2$ liver sample with the same amount of cRNA from a reference pool comprised of equal amounts of cRNA from each of the liver samples profiled. An in-house custom designed chip representing 23,574 genes was used as the microarray. Array images were processed as described in Hughes, et al., 2000, Cell 102, p. 109, to obtain background noise, single channel intensity, and associated measurement error estimates. Expression changes between two samples (single versus pool) were quantified as $\log_{10}$ (expression ratio) where the 'expression ratio' was taken to be the ratio between normalized, background-corrected intensity values for the two channels (red and green) for each spot on the array. An error model for the log ratio was applied as described by Roberts et al., 2000, Science 287, p. 873, to quantify the significance of expression changes between two samples.

Steps 208-216. Those genes in the pancreas that were able to discriminate blood insulin levels in the liver were identified using the microarray expression data (Section 5.1, step 208). These genes were then clustered using the methods described in step 210 of Section 5.1. This clustering is illustrated in FIG. 9. The cluster of genes illustrated in FIG. 9 is able to discriminate between the high and low insulin levels, even though the insulin gene is not transcribed in the liver. In other words, gene expression levels in the liver are affected by insulin levels, where the insulin was transcribed in the pancreas.

Step 218. In this example, the target gene in the primary tissue is known and, at this point, a signature (a set of genes whose expression in the liver discriminate insulin level in the pancreas) that is associated with the activity of this gene has been identified. Nevertheless, the example can be can extended to show the additional steps described in Section 5.1. The genes represented in the cluster illustrated in FIG. 9, in addition to genes correlated to the expression of the genes illustrated in FIG. 9 are used in a genetic analysis. That is, a whole genome genetic analysis is performed for each gene illustrated in FIG. 9, in addition to those genes correlated to the expression of the genes in FIG. 9. In this example, the whole genome study is a mode-based linkage analysis that uses a high density mouse marker map and the pedigree data from the F2 cross.

Steps 222-236. The linkage studies in step 218 show a significant hot spot defined by an 8 cM window on chromosome 19, a region that contains the insulin gene. There are more than 900 genes that are moderately linked to this chromosome 19 locus, which is almost 10-fold more genes than would be expected by chance. Of the 125 well-annotated genes linked to the chromosome 19 region, a majority have been associated with insulin levels in the literature. Representative genes that moderately link to the chromosome 19 locus are given in Table 3.

TABLE 3

A sample of the over 900 genes that link to the Insulin locus

| Gene symbol | Gene name |
| --- | --- |
| Igfbp2 | insulin-like growth factor binding protein |
| Itga6 | integrin alpha 6 |
| Hmgcs2 | 3-hydroxy-3-methylglutryl-coenzyme A synthase 2 |
| Ptprd | protein tyrosine phosphatase, receptor type D |
| Hmgcl | 3-hydroxy-3-methylglutaryl-coenzyme A lyase |
| Pex14 | peroxisomal biogensis factor 14 |
| Abcb4 | ATP-binding cassette, sub-family B, member 4 |
| Itgax | integrin alpha X |
| Ptpre | protein tyrosine phosphatase, receptor type E |
| Adam10 | A disintegrin and metalloprotease domain 10 |
| Itgb2 | integrin beta 2 |
| Aldh3a2 | aldehyde dehydrogenase family 3, subfamily A2 |
| Itgb5 | integrin beta 5 |
| Itgp | integrin-associated protein |
| Gabbr1 | gamma-aminobutyric acid (GABA-B) receptor 1 |
| Ppara | peroxisome proliferator activated |
| Ptpn18 | protein tyrosine phosphatase, non-receptor type |
| Pdgfrb | platelet derived growth factor receptor, beta polypeptide |

If there is no a priori knowledge that the insulin gene was one of the targets in this region, the steps performed in this example would have at least provided a loci (e.g., QTL) that is associated with the expression levels associated with the insulin levels. As illustrated in FIG. 10, the genes linking to the insulin locus are physically located on other chromosomes, but are under control of the insulin locus, to some degree.

The example above provides a method of anchoring a gene to a 8 cM region of the genome. In the example, the gene is known. However, if the gene is not known, further work is necessary to determine which of the genes is the target of the perturbation that was initially selected. In this example, the perturbation is the level of insulin genes in the pancreas. Genes in the 8 cM region can be assessed to determine if their expression levels can explain the other QTL co-localizing to its physical location. On this basis, genes can be excluded.

Furthermore, the techniques outlined in Section 5.1 (steps 222-236) can be used to help refine the list of possible candidate genes.

5.19. Pleiotropy Test

In some embodiments, a test for pleiotropy is performed. The pleiotropy test determines whether an eQTL and a cQTL are statistically indistinguishable QTL. In considering a test for pleiotropy in accordance with the present invention, let $Y_1$ and $Y_2$ represent quantitative trait random variables, with QTL $Q_1$ and $Q_2$ at positions $p_1$ and $p_2$, respectively. It is of interest to determine whether $p_1=p_2$, indicating a pleiotropic effect at the QTL for traits $Y_1$ and $Y_2$. Jiang and Zeng, 1995, Genetics 140, 1111, devised statistical tests to assess whether the positions are equal. Since the positions under consideration usually will be relatively close together on a given chromosome (e.g., within 20 cM), it is expected that $Y_1$ and $Y_2$ will be correlated, and so the most basic model for these traits under the control of a single, common QTL is formed as:

$$\begin{pmatrix} y_1 \\ y_2 \end{pmatrix} = \begin{pmatrix} \mu_1 \\ \mu_2 \end{pmatrix} + \begin{pmatrix} \beta_1 \\ \beta_2 \end{pmatrix} Q + \begin{pmatrix} \varepsilon_1 \\ \varepsilon_2 \end{pmatrix},$$

where Q is a categorical random variable indicating the genotypes at the position of interest, and $$\begin{pmatrix} \varepsilon_1 \\ \varepsilon_2 \end{pmatrix}$$

is distributed as a bivariate normal random variable with mean $$\begin{pmatrix} 0 \\ 0 \end{pmatrix}$$

and covariance matrix $$\begin{pmatrix} \sigma_1^2 & \sigma_1 \sigma_2 \\ \sigma_2 \sigma_1 & \sigma_2^2 \end{pmatrix}.$$

The case where $p_1=P_2$ represents the null hypothesis of pleiotropy. The aim is to test this null against a more general alternative hypothesis that indicates $p_1 \neq p_2$. The alternative hypotheses of interest can be captured by the following model:

$$\begin{pmatrix} y_1 \\ y_2 \end{pmatrix} = \begin{pmatrix} \mu_1 \\ \mu_2 \end{pmatrix} + \begin{pmatrix} \beta_1 & \beta_2 \\ \beta_3 & \beta_4 \end{pmatrix} \begin{pmatrix} Q_1 \\ Q_2 \end{pmatrix} + \begin{pmatrix} \varepsilon_1 \\ \varepsilon_2 \end{pmatrix},$$

where the $\epsilon_i$ are distributed as for the pleiotropy model. The null hypothesis can be compared against any of a series of alternative hypotheses. The likelihoods for the two competing models (null hypothesis and alternative hypothesis) are easily formed, and maximum likelihood methods are then employed to estimate the model parameters ($\mu_i$, $\beta_j$, and $\sigma_k$). With the maximum likelihood estimates in hand, the likelihood ratio test statistic can be formed to directly test the null hypothesis against the alternative.

There are several alternative hypotheses that can be tested in this setting including:

$$H_A: \beta_1 \neq 0, \beta_4 \neq 0, \beta_2 = 0, \beta_3 = 0,$$

indicating closely linked QTL with no pleiotropic effects, $$H_A: \beta_1 \neq 0, \beta_4 \neq 0, \beta_2 \neq 0, \beta_3 = 0,$$

indicating closely linked QTL with pleiotropic effects at the first position, $$H_A: \beta_1 \neq 0, \beta_4 \neq 0, \beta_2 = 0, \beta_3 \neq 0,$$

indicating closely linked QTL with pleiotropic effects at the second position, and $$H_A: \beta_1 \neq 0, \beta_4 \neq 0, \beta_2 \neq 0, \beta_3 \neq 0,$$

indicating closely linked QTL with pleiotropic effects at both positions. Other null hypotheses and corresponding alternative hypotheses naturally follow from the general models presented here.

6. References Cited

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1. These program modules may be stored on a CD-ROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of identifying a set of cellular constituents in a secondary tissue of a species that serves as a surrogate marker for an activity of a target gene that affects a trait of interest, which said target gene is expressed in a primary tissue of said species, the method comprising:
    (a) constructing a classifier using abundance levels, each abundance level being of a respective cellular constituent in a plurality of cellular constituents measured in said secondary tissue in a portion of a population of said species, to derive an ordered set of cellular constituents, wherein
    said portion of the population comprises a first subgroup and a second subgroup that have distinct phenotypes, respectively, for the trait;

respective abundance levels of each cellular constituent in said plurality of cellular constituents discriminate between said first subgroup and said second subgroup; and (b) classifying said population of said species into a plurality of subtypes using said classifier, wherein said classifying is based on abundance levels of said ordered set of cellular constituents for each organism in said population; and (c) identifying one or more cellular constituents that can discriminate members of said population between a first subtype in said plurality of subtypes and a second subtype in said plurality of subtypes, thereby identifying said one or more cellular constituents as said set of cellular constituents, wherein said constructing, classifying, and identifying steps are performed on a suitably programmed computer.

2. The method of claim 1 wherein said trait of interest is a clinical trait that does not exhibit classic Mendelian inheritance.

3. The method of claim 2 wherein said clinical trait is an amount of the gene product of the target gene that is in the blood of said population of species.

4. The method of claim 1 wherein said trait of interest is a complex disease.

5. The method of claim 4 wherein said complex disease is asthma, ataxia telangiectasia, bipolar disorder, cancer, common late-onset Alzheimer's disease, diabetes, heart disease, hereditary early-onset Alzheimer's disease, hereditary nonpolyposis colon cancer, hypertension, infection, maturity-onset diabetes of the young, mellitus, migraine, nonalcoholic fatty liver, nonalcoholic steatohepatitis, non-insulin-dependent diabetes mellitus, obesity, polycystic kidney disease, psoriases, schizophrenia, or xeroderma pigmentosum.

6. The method of claim 1 wherein said first subgroup is exposed to a perturbation that affects said trait prior to said constructing step (a) and said second subgroup is not exposed to said perturbation.

7. The method of claim 6 wherein said perturbation is environmental.

8. The method of claim 6 wherein said perturbation is exposure to a compound, exposure to an allergen, exposure to pain, exposure to a hot temperature, exposure to a cold temperature, a diet, sleep deprivation, isolation, or an exercise regimen.

9. The method of claim 6 wherein said perturbation is genetic.

10. The method of claim 6 wherein said perturbation is a gene knockout, exposure to an inhibitor of a gene product, N-ethyl-N-nitrosourea mutagenesis, or siRNA knockdown of a gene.

11. The method of claim 1 wherein said plurality of cellular constituents is mRNA, cRNA or cDNA and each said abundance level is obtained by measuring a transcriptional state of all or a portion of said first plurality of cellular constituents in said secondary tissue.

12. The method of claim 1 wherein said plurality of cellular constituents is proteins and each said abundance level is obtained by measuring a translational state of all or a portion of said first plurality of cellular constituents in said secondary tissue.

13. The method of claim 1 wherein variance in abundance levels of a cellular constituent in said plurality of cellular constituents between said first subgroup and said second subgroup is determined by a correlation analysis, a t-test, a paired t-test, an analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

14. The method of claim 1 wherein
said first subgroup does not exhibit said trait and said second subgroup exhibits said trait; and
said constructing said classifier step (a) comprises determining those cellular constituents whose abundance levels in said secondary tissue discriminate said first subgroup from said second subgroup.

15. The method of claim 14 wherein determining those cellular constituents whose abundance levels in said secondary tissue discriminate between said first subgroup and said second subgroup is determined by performing a correlation analysis, a t-test, a paired t-test, an analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

16. The method of claim 1 wherein said trait of interest is a clinical trait that does not exhibit classic Mendelian, inheritance and said first subgroup and said second subgroup exhibit variance with respect to said clinical trait.

17. The method of claim 16 wherein determining those cellular constituents whose abundance levels in said secondary tissue discriminate said first subgroup and said second subgroup is determined by performing a correlation analysis, an analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test.

18. The method of claim 1, wherein said constructing said classifier step (a) comprises:

(i) constructing a plurality of cellular constituent vectors, wherein
each cellular constituent vector in said plurality of cellular constituent vectors represents a cellular constituent in said plurality of cellular constituents, and
each cellular constituent vector in said plurality of cellular constituent vectors comprises a plurality of cellular constituents levels, wherein each cellular constituent level in said plurality of cellular constituent levels is a level of the cellular constituent in the secondary tissue of a different organism in the population;

(ii) clustering said plurality of cellular constituents vectors to form a cellular constituent vector cluster; and (iii) identifying the order of cellular constituents in said cellular constituent vector cluster.

19. The method of claim 18 wherein said classifying step (b) and said identifying step (c) comprise (A) constructing a respective phenotypic vector for each organism in all or a portion of said population, each phenotypic vector comprising a plurality of measured cellular constituents levels for said organism arranged in an order that is determined by said cellular constituent vector cluster;

(B) clustering said phenotypic vectors to form a first phenotypic cluster and a second phenotypic cluster; and (C) identifying a group of cellular constituents represented in said respective phenotypic vectors that discriminates between said first phenotypic cluster and said second phenotypic cluster.

20. The method of claim 1 wherein said constructing step (a) comprises classifying said population into a plurality of phenotypic groups based on one or more phenotypes measured for a plurality of members of said population, said plurality of phenotypic groups comprising said first subgroup and said second subgroup wherein said first subgroup represents a first phenotypic extreme with respect to a phenotype in said one or more phenotypes and said second subgroup represents a second phenotypic extreme with respect to a phenotype in said one or more phenotypes.

21. The method of claim 20 wherein
a plurality of phenotypic vectors are created, each phenotypic vector in said plurality of phenotypic vectors corresponding to a member of said population, each said phenotypic vector comprising said one or more phenotypes measured for the corresponding member of said population; and
said classifying comprises clustering said phenotypic vectors into said plurality of phenotypic groups.

22. The method of claim 20 wherein said first phenotypic extreme or said second phenotypic extreme is a top or a lowest fortieth percentile of said population with respect to said phenotype.

23. The method of claim 20 wherein said first phenotypic extreme or said second phenotypic extreme is a top or a lowest twentieth percentile of said population with respect to said phenotype.

24. The method of claim 1 wherein each respective cellular constituent in said plurality of cellular constituents is assigned a metric based on an ability for said respective cellular constituent to discriminate between said first subgroup and said second subgroup and wherein said plurality of cellular constituents is reduced to a reduced set of cellular constituents or principal components using a reducing algorithm that uses the respective metric of each cellular constituent in said plurality of cellular constituents and wherein said classifier is based on said reduced set.

25. The method of claim 1, wherein a plurality of expression vectors are created, each expression vector in said plurality of expression vectors representing a cellular constituent in said plurality of cellular constituents and each expression vector in said plurality of expression vectors comprising respective abundance levels from said first subgroup and said second subgroup, said constructing said classifier step (a) comprising:
clustering said plurality of expression vectors in order to form a plurality of expression vector subgroups and wherein said classifier is based on an expression vector subgroup in said plurality of expression vector subgroups.

26. The method of claim 1 wherein
each respective cellular constituent in said plurality of cellular constituents is assigned a respective metric based on an ability for said respective cellular constituent to discriminate between said first subgroup and said second subgroup, and
said classifier is a neural network that is trained by each said cellular constituent in said plurality of cellular constituents and the respective metric assigned to each said cellular constituent in said plurality of cellular constituents.

27. The method of claim 24 wherein each respective cellular constituent or principal component in said reduced set is assigned a respective metric based on an ability for said respective cellular constituent or principal component to discriminate between said first subgroup and said second subgroup; and said classifier is a neural network that is trained by each said cellular constituent or principal component in said reduced set and the respective metric assigned to each said cellular constituent or principal component in said reduced set.

28. The method of claim 25 wherein
each respective cellular constituent in said expression vector subgroup is assigned a respective metric based on an ability for said respective cellular constituent to discriminate between said first subgroup and said second subgroup; and
said classifier is a neural network that is trained by each said cellular constituent in said expression vector subgroup and the respective metric assigned to each said cellular constituent in said expression vector subgroup.

29. The method of claim 1 wherein each respective cellular constituent in said plurality of cellular constituents is assigned a respective metric based on an ability for said respective cellular constituent to discriminate between said first subgroup and said second subgroup, and said classifying step (b) comprises classifying all or a portion of said population into said plurality of subtypes using Bayesian decision theory in which each said cellular constituent in said plurality of cellular constituents and the respective metric assigned to each said cellular constituent in said plurality of cellular constituents serves as a priori information.

30. The method of claim 24 wherein each respective cellular constituent or principal component in said reduced set is assigned a respective metric based on an ability for said respective cellular constituent or principal component to discriminate between said first subgroup and said second subgroup, and said classifying step (b) comprises classifying said population into said plurality of subtypes using Bayesian decision theory in which each said cellular constituent or principal component in said reduced set and the respective metric assigned to each said cellular constituent or principal component in said reduced set serves as a priori information.

31. The method of claim 25 wherein each respective cellular constituent in said expression vector subgroup is assigned a respective metric based on an ability for said respective cellular constituent to discriminate between said first subgroup and said second subgroup, and said classifying step (b) comprises classifying said population into said plurality of subtypes using Bayesian decision theory in which each said cellular constituent in said expression vector subgroup and the respective metric assigned to each said cellular constituent in said expression vector subgroup serves as a priori information.

32. The method of claim 1 wherein each respective cellular constituent in said second plurality of cellular constituents is assigned a respective metric based on an ability for said respective cellular constituent to discriminate between said first subgroup and said second subgroup, and said classifying step (b) comprises classifying said population into said plurality of subtypes using linear discriminate analysis, a linear programming algorithm, a support vector machine, or a simple decision tree.

33. The method of claim 24 wherein each respective cellular constituent or principal component in said reduced set is assigned a respective metric based on an ability for said respective cellular constituent or principal component to discriminate between said first subgroup and said second subgroup, and said classifying step (b) comprises classifying said population into said plurality of subtypes using linear discriminate analysis, a linear programming algorithm, a support vector machine, or a simple decision tree.

34. The method of claim 25 wherein each respective cellular constituent in said expression vector subgroup is assigned a respective metric based on an ability for said respective cellular constituent to discriminate between said first subgroup and said second subgroup, and said classifying step (b) comprises classifying said population into said plurality of subtypes using linear discriminate analysis, a linear programming algorithm, a support vector machine.

35. The method of claim 1 wherein each respective cellular constituent in said expression vector subgroup is assigned a respective metric based on an ability for said respective cellular constituent to discriminate between said first subgroup and said second subgroup, and said classifying step (b) comprises classifying said population into said plurality of subtypes using a simple decision tree.

36. The method of claim 1 wherein an identity of the target gene in the primary tissue of said species is not known, the method further comprising:
- (i) performing quantitative genetic analysis, for each cellular constituent in all or a portion of the cellular constituents identified in step (c), using an abundance statistic for the cellular constituent as a quantitative trait in the quantitative genetic analysis, the abundance statistic comprising a measurement of the level of said cellular constituent in the secondary tissue of each organism in one of said plurality of subtypes, thereby identifying a hot spot chromosomal region of the genome of said species that links to one or more cellular constituents in said species;
- (ii) identifying a plurality of genes that are in said hot spot chromosomal region;
- (iii) for each gene in said plurality of genes in said hot spot region, performing quantitative genetic analysis using an abundance level of said gene or gene product as a quantitative trait; and
- (iv) ranking each gene identified in said hot spot based on the quantitative genetic analyses performed in step (iii) to form a ranked list of genes.

37. The method of claim 36 wherein said measurement of the level of said cellular constituent in the secondary tissue of each organism in said one of said plurality of subtypes that is used in step (i) to form said abundance statistic is a measurement of the translational state of said cellular constituent.

38. The method of claim 36 wherein said measurement of the level of said cellular constituent in the secondary tissue of each organism in said one of said plurality of subtypes that is used in step (i) to form said abundance statistic is a measurement of the activity or post-translational modification of said cellular constituent.

39. The method of claim 36 wherein each quantitative genetic analysis performed in step (i) comprises model-based linkage analysis.

40. The method of claim 36 wherein each quantitative genetic analysis performed in step (i) comprises model-free linkage analysis.

41. The method of claim 36 wherein each quantitative genetic analysis performed in step (i) comprises association analysis.

42. The method of claim 36 wherein said measurement of the level of said cellular constituent in the secondary tissue of each organism in said one of said plurality of subtypes is a measurement of the activity of the gene or post-translational modification of the gene.

43. The method of claim 36 wherein each said quantitative genetic analysis performed in step (iii) comprises:
- (A) testing for linkage or association between a position in the genome of said species and the quantitative trait, wherein the quantitative trait is a measurement of the level of the gene corresponding to the quantitative genetic analysis in each organism in said;
- (B) advancing to another position in the genome; and
- (C) repeating steps (A) and (B) until an end of the genome is reached.

44. The method of claim 43 wherein said measurement of the level of said gene in each organism in said one of said plurality of subtypes is a measurement of the transcriptional state of the gene.

45. The method of claim 43 wherein said measurement of the level of said gene in each organism in said one of said plurality of subtypes is a measurement of the translational state of the gene.

46. The method of claim 36 wherein said method further comprises using a plurality of genes in said ranked list of genes in a multivariate analysis to determine whether said genes are genetically interacting.

47. The method of claim 46 wherein said set of genetic markers comprise single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, or simple sequence repeats for each organism in said one of said plurality of subtypes.

48. The method of claim 1 wherein said species is human, rat or mouse.

49. The method of claim 1 wherein said population comprises an $F_2$ population, an $F_t$ population, an $F_{2:3}$ population or a Design III population.

50. A computer program product for use in conjunction with a computer system, the computer program product comprising a computer readable storage medium and a computer program mechanism embedded therein, the computer program mechanism comprising:
- a classification module for identifying a set of cellular constituents in a secondary tissue of a species that serves as a surrogate marker for an activity of a target gene that affects a trait of interest, which said target gene is expressed in a primary tissue of said species; the classification module comprising:
  - (a) executable instructions for constructing a classifier using abundance levels, each abundance level being of a respective cellular constituent in a plurality of cellular constituents measured in said secondary tissue in a portion of a population of said species, to derive an ordered set of cellular constituents, wherein said portion of the population comprises a first subgroup and a second subgroup that have distinct phenotypes, respectively, for the trait;
    respective abundance levels of each cellular constituent in said plurality of cellular constituents discriminate between said first subgroup and said second subgroup;
  - (b) executable instructions for classifying said population of said species into a plurality of subtypes using said classifier, wherein said classifying is based on abundance levels of said ordered set of cellular constituents for each organism in said population; and
  - (c) executable instructions for identifying one or more cellular constituents that can discriminate members of said population between a first subtype in said plurality of subtypes and a second subtype in said plurality of subtypes, thereby identifying said one or more cellular constituents as said set of cellular constituents.

51. A computer system for identifying a set of cellular constituents in a secondary tissue of a species that serves as a surrogate marker for an activity of a target gene expressed in a primary tissue of said species, the computer system comprising:
a central processing unit;
a memory, coupled to the central processing unit, the memory storing a classification module, the classification module comprising:
(a) executable instructions for constructing a classifier using abundance levels, each abundance level being of a respective cellular constituent in a plurality of cellular constituents measured in said secondary tissue in a portion of a population of said species, to derive an ordered set of cellular constituents, wherein said portion of the population comprises a first subgroup and a second subgroup that have distinct phenotypes, respectively, for the trait;
respective abundance levels of each cellular constituent in said plurality of cellular constituents discriminate between said first subgroup and said second subgroup;
(b) executable instructions for classifying said population of said species into a plurality of subtypes using said classifier, wherein said classifying is based on abundance levels of said ordered set of cellular constituents for each organism in said population; and
(c) executable instructions for identifying one or more cellular constituents that can discriminate members of said population between a first subtype in said plurality of subtypes and a second subtype in said plurality of subtypes, thereby identifying said one or more cellular constituents as said set of cellular constituents.

52. The computer program product of claim 50 wherein said first subgroup is exposed to a perturbation that affects said trait prior to said constructing step (a) and said second subgroup is not exposed to said perturbation.

53. The computer program product of claim 50 wherein said plurality of cellular constituents is mRNA, cRNA or cDNA and each said abundance level is obtained by measuring a transcriptional state of all or a portion of said first plurality of cellular constituents in said secondary tissue.

54. The computer program product of claim 50, wherein said constructing said classifier step (a) comprises:
(i) constructing a plurality of cellular constituent vectors, wherein
each cellular constituent vector in said plurality of cellular constituent vectors represents a cellular constituent in said plurality of cellular constituents, and
each cellular constituent vector in said plurality of cellular constituent vectors comprises a plurality of cellular constituents levels, wherein each cellular constituent level in said plurality of cellular constituent levels is a level of the cellular constituent in the secondary tissue of a different organism in the population;
(ii) clustering said plurality of cellular constituents vectors to form a cellular constituent vector cluster; and
(iii) identifying the order of cellular constituents in said cellular constituent vector cluster.

55. The computer program product of claim 50 wherein said classifying step (b) and said identifying step (c) comprise:
(A) constructing a respective phenotypic vector for each organism in all or a portion of said population, each phenotypic vector comprising a plurality of measured cellular constituents levels for said organism arranged in an order that is determined by said cellular constituent vector cluster;
(B) clustering said phenotypic vectors to form a first phenotypic cluster and a second phenotypic cluster; and
(C) identifying a group of cellular constituents represented in said respective phenotypic vectors that discriminates between said first phenotypic cluster and said second phenotypic cluster.

56. The computer program product of claim 50 wherein an identity of the target gene in the primary tissue of said species is not known, the method further comprising:
(i) performing quantitative genetic analysis, for each cellular constituent in all or a portion of the cellular constituents identified in step (c) using an abundance statistic for the cellular constituent as a quantitative trait in the quantitative genetic analysis, the abundance statistic comprising a measurement of the level of said cellular constituent in the secondary tissue of each organism in one of said plurality of subtypes, thereby identifying a hot spot chromosomal region of the genome of said species that links to one or more cellular constituents in said species;
(ii) identifying a plurality of genes that are in said hot spot chromosomal region;
(iii) for each gene in said plurality of genes in said hot spot region, performing quantitative genetic analysis using an abundance level of said gene or gene product as a quantitative trait; and
(iv) ranking each gene identified in said hot spot based on the quantitative genetic analyses performed in step (iii) to form a ranked list of genes.

57. The computer program product of claim 56 wherein each quantitative genetic analysis performed in step (i) comprises association analysis.

58. The computer program product of claim 56 wherein each said quantitative genetic analysis performed in step (iii) comprises:
(A) testing for linkage or association between a position in the genome of said species and the quantitative trait, wherein the quantitative trait is a measurement of the level of the gene corresponding to the quantitative genetic analysis in each organism in said one of said plurality of subtypes;
(B) advancing to another position in the genome; and
(C) repeating steps (A) and (B) until an end of the genome is reached.

59. The method of claim 58 wherein said measurement of the level of said gene in each organism in said one of said plurality of subtypes is a measurement of the transcriptional state of the gene.

60. The computer system of claim 51 wherein said first subgroup is exposed to a perturbation that affects said trait prior to said constructing step (a) and said second subgroup is not exposed to said perturbation.

61. The computer system of claim 51 wherein said plurality of cellular constituents is mRNA, cRNA or cDNA and each said abundance level is obtained by measuring a transcriptional state of all or a portion of said plurality of cellular constituents in said secondary tissue.

62. The computer system of claim 51, wherein said constructing said classifier step (a) comprises:
(i) constructing a plurality of cellular constituent vectors, wherein each cellular constituent vector in said plurality of cellular constituent vectors represents a cellular constituent in said plurality of cellular constituents, and each cellular constituent vector in said plurality of cellular constituent vectors comprises a plurality of cellular constituents levels, wherein each cellular constituent level in said plurality of cellular constituent levels is a level of the cellular constituent in the secondary tissue of a different organism in the population;

(ii) clustering said plurality of cellular constituents vectors to form a cellular constituent vector cluster; and (iii) identifying the order of cellular constituents in said cellular constituent vector cluster.

63. The computer system of claim 51 wherein said classifying step (b) and said identifying step (c) comprise (A) constructing a respective phenotypic vector for each organism in all or a portion of said population, each phenotypic vector comprising a plurality of measured cellular constituents levels for said organism arranged in an order that is determined by said cellular constituent vector cluster;

(B) clustering said phenotypic vectors to form a first phenotypic cluster and a second phenotypic cluster; and (C) identifying a group of cellular constituents represented in said respective phenotypic vectors that discriminates between said first phenotypic cluster and said second phenotypic cluster.

64. The computer program product of claim 50 wherein an identity of the target gene in the primary tissue of said species is not known, the method further comprising:

(i) performing quantitative genetic analysis, for each cellular constituent in all or a portion of the cellular constituents identified in step (c), using an abundance statistic for the cellular constituent as a quantitative trait in the quantitative genetic analysis, the abundance statistic comprising a measurement of the level of said cellular constituent in the secondary tissue of each organism in one of said plurality of subtypes, thereby identifying a hot spot chromosomal region of the genome of said species that links to one or more cellular constituents in said species;

(ii) identifying a plurality of genes that are in said hot spot chromosomal region;

(iii) for each gene in said plurality of genes in said hot spot region, performing quantitative genetic analysis using an abundance level of said gene or gene product as a quantitative trait; and (iv) ranking each gene identified in said hot spot based on the quantitative genetic analyses performed in step (iii) to form a ranked list of genes.

65. The computer program product of claim 64 wherein each quantitative genetic analysis performed in step (i) comprises association analysis.

66. The computer program product of claim 64 wherein each said quantitative genetic analysis performed in step (iii) comprises:

(A) testing for linkage or association between a position in the genome of said species and the quantitative trait, wherein the quantitative trait is a measurement of the level of the gene corresponding to the quantitative genetic analysis in each organism in said one of said plurality of subtypes;

(B) advancing to another position in the genome; and (C) repeating steps (A) and (B) until an end of the genome is reached.

67. The method of claim 66 wherein said measurement of the level of said gene in each organism in said one of said plurality of subtypes is a measurement of the transcriptional state of the gene.

* * * * *